United States Patent
Chevalier et al.

(10) Patent No.: US 12,094,607 B2
(45) Date of Patent: Sep. 17, 2024

(54) SYSTEMS AND METHODS TO IDENTIFY PERSONS AND/OR IDENTIFY AND QUANTIFY PAIN, FATIGUE, MOOD, AND INTENT WITH PROTECTION OF PRIVACY

(71) Applicant: Atlas5D, Inc., Cambridge, MA (US)

(72) Inventors: Timothy W. Chevalier, Cambridge, MA (US); Zebadiah M. Kimmel, Cambridge, MA (US); Jonathan S. Varsanik, Cambridge, MA (US)

(73) Assignee: Atlas5D, Inc., Lincoln, MA (US)

( * ) Notice: Subject to any disclaimer, the term of this patent is extended or adjusted under 35 U.S.C. 154(b) by 803 days.

(21) Appl. No.: 17/185,883

(22) Filed: Feb. 25, 2021

(65) Prior Publication Data
US 2021/0183516 A1    Jun. 17, 2021

Related U.S. Application Data

(63) Continuation of application No. 15/666,514, filed on Aug. 1, 2017, now Pat. No. 11,017,901.
(Continued)

(51) Int. Cl.
*G06N 20/00*    (2019.01)
*G16H 10/60*    (2018.01)
(Continued)

(52) U.S. Cl.
CPC ............. *G16H 50/20* (2018.01); *G16H 10/60* (2018.01); *G16H 30/20* (2018.01); *G16H 30/40* (2018.01);
(Continued)

(58) Field of Classification Search
None
See application file for complete search history.

(56) References Cited

U.S. PATENT DOCUMENTS

| 4,406,544 A | 9/1983 | Takada et al. |
| 5,742,521 A | 4/1998 | Ellenby et al. |

(Continued)

FOREIGN PATENT DOCUMENTS

| JP | 2005-242759 A | 9/2005 |
| JP | 2010-211655 A | 9/2010 |

(Continued)

OTHER PUBLICATIONS

Popa, et al., Assessment of Customers' Level of Interest, 2012 19th IEEE International Conference on Image Processing, 2012, pp. 41-44 (Year: 2012).*

(Continued)

*Primary Examiner* — Wilbert L Starks
(74) *Attorney, Agent, or Firm* — Choate, Hall & Stewart LLP; Michael D. Schmitt

(57) ABSTRACT

The disclosed technology enables, among other things, the identification of persons and the characterization of mental perceptions (e.g., pain, fatigue, mood) and/or intent (e.g., to perform an action) for medical, safety, home care, and other purposes. Of significance are applications that require long-term patient monitoring, such as tracking disease progression (e.g., multiple sclerosis), or monitoring treatment or rehabilitation efficacy. Therefore, longitudinal data must be acquired over time for the person's identity and other characteristics (e.g., pain level, usage of a cane). However, conventional methods of person identification (e.g., photography) acquire unnecessary personal information, resulting in privacy concerns. The disclosed technology allows measurements to be performed while protecting privacy and functions with partial or incomplete measurements, making it robust to real-world (noisy, uncontrolled) settings, such as in a person's home (whether living alone or with others).

26 Claims, 28 Drawing Sheets

Related U.S. Application Data

(60) Provisional application No. 62/438,229, filed on Dec. 22, 2016, provisional application No. 62/370,083, filed on Aug. 2, 2016.

(51) Int. Cl.

| | | |
|---|---|---|
| *G16H 30/20* | (2018.01) | |
| *G16H 30/40* | (2018.01) | |
| *G16H 40/63* | (2018.01) | |
| *G16H 40/67* | (2018.01) | |
| *G16H 50/20* | (2018.01) | |
| *G16H 50/30* | (2018.01) | |

(52) U.S. Cl.
CPC ............ *G16H 40/63* (2018.01); *G16H 40/67* (2018.01); *G16H 50/30* (2018.01); *G01N 2800/304* (2013.01); *G01N 2800/52* (2013.01); *G06N 20/00* (2019.01)

(56) References Cited

U.S. PATENT DOCUMENTS

| | | |
|---|---|---|
| 7,397,931 B2 | 7/2008 | Imagawa et al. |
| 7,440,590 B1 | 10/2008 | Hassebrook et al. |
| 8,269,834 B2 | 9/2012 | Albertson et al. |
| 8,613,666 B2 | 12/2013 | Esaki et al. |
| 8,639,020 B1 | 1/2014 | Kutliroff et al. |
| 8,644,556 B2 | 2/2014 | Zhou et al. |
| 8,787,663 B2 | 7/2014 | Litvak et al. |
| 8,792,722 B2 | 7/2014 | Liu et al. |
| 8,902,198 B1 | 12/2014 | Karakotsios et al. |
| 8,902,607 B1 | 12/2014 | Chang et al. |
| 9,037,354 B2 | 5/2015 | Mondragon et al. |
| 9,075,444 B2 | 7/2015 | Noda et al. |
| 9,141,184 B2 | 9/2015 | Uchikoshi et al. |
| 9,189,886 B2 | 11/2015 | Black et al. |
| 9,323,982 B2 | 4/2016 | Kim et al. |
| 9,341,464 B2 | 5/2016 | Kimmel |
| 9,349,039 B2 | 5/2016 | Hanzawa et al. |
| 9,361,696 B2 | 6/2016 | Allezard et al. |
| 9,393,695 B2 | 7/2016 | Scott et al. |
| 9,520,072 B2 | 12/2016 | Sun et al. |
| 9,524,554 B2 | 12/2016 | Plagge et al. |
| 9,600,993 B2 | 3/2017 | Kimmel |
| 9,737,239 B2 | 8/2017 | Kimmel |
| 2003/0209893 A1 | 11/2003 | Breed et al. |
| 2003/0231788 A1 | 12/2003 | Yukhin et al. |
| 2004/0083142 A1 | 4/2004 | Kozzinn |
| 2005/0094879 A1 | 5/2005 | Harville |
| 2006/0252541 A1 | 11/2006 | Zalewski et al. |
| 2007/0229850 A1 | 10/2007 | Herber |
| 2009/0103780 A1 | 4/2009 | Nishihara et al. |
| 2009/0244309 A1 | 10/2009 | Maison et al. |
| 2010/0007717 A1 | 1/2010 | Spektor et al. |
| 2010/0049095 A1 | 2/2010 | Bunn et al. |
| 2010/0172567 A1 | 7/2010 | Prokoski |
| 2010/0191541 A1 | 7/2010 | Prokoski |
| 2010/0226533 A1 | 9/2010 | Bharath et al. |
| 2011/0052006 A1 | 3/2011 | Gurman et al. |
| 2011/0193939 A1 | 8/2011 | Vassigh et al. |
| 2011/0205337 A1 | 8/2011 | Ganapathi et al. |
| 2011/0206273 A1 | 8/2011 | Plagemann et al. |
| 2011/0211044 A1 | 9/2011 | Shpunt et al. |
| 2011/0211754 A1 | 9/2011 | Litvak et al. |
| 2011/0288964 A1 | 11/2011 | Linder et al. |
| 2011/0298801 A1 | 12/2011 | Wexler et al. |
| 2012/0046101 A1 | 2/2012 | Marks et al. |
| 2012/0076361 A1 | 3/2012 | Fujiyoshi |
| 2012/0146903 A1 | 6/2012 | Arihara et al. |
| 2012/0159290 A1 | 6/2012 | Pulsipher et al. |
| 2012/0229634 A1 | 9/2012 | Laett et al. |
| 2012/0257814 A1 | 10/2012 | Kohli et al. |
| 2012/0269384 A1 | 10/2012 | Jones et al. |
| 2012/0314046 A1 | 12/2012 | Zhuang et al. |
| 2012/0326959 A1 | 12/2012 | Murthi et al. |
| 2013/0048722 A1 | 2/2013 | Davis et al. |
| 2013/0088426 A1 | 4/2013 | Shigeta et al. |
| 2013/0163879 A1 | 6/2013 | Katz et al. |
| 2013/0182898 A1 | 7/2013 | Maeda et al. |
| 2013/0315475 A1 | 11/2013 | Song et al. |
| 2014/0163330 A1 | 6/2014 | Horseman |
| 2014/0241571 A1 | 8/2014 | Bilet et al. |
| 2014/0243686 A1 | 8/2014 | Kimmel |
| 2014/0279740 A1 | 9/2014 | Wernevi et al. |
| 2014/0298379 A1 | 10/2014 | Singh |
| 2014/0299775 A1 | 10/2014 | Kimmel |
| 2014/0300907 A1 | 10/2014 | Kimmel |
| 2015/0000025 A1 | 1/2015 | clements |
| 2015/0213702 A1 | 7/2015 | Kimmel |
| 2015/0310629 A1 | 10/2015 | Utsunomiya et al. |
| 2015/0325004 A1 | 11/2015 | Utsunomiya et al. |
| 2016/0247017 A1 | 8/2016 | Sareen et al. |
| 2016/0266607 A1 | 9/2016 | Varsanik et al. |
| 2016/0267652 A1 | 9/2016 | Kimmel et al. |
| 2016/0331277 A1 | 11/2016 | Kimmel |

FOREIGN PATENT DOCUMENTS

| | | |
|---|---|---|
| JP | 2012-115570 A | 6/2012 |
| JP | 2016-082552 A | 5/2016 |
| WO | WO-01/001354 A1 | 1/2001 |
| WO | WO-2013/058985 A1 | 4/2013 |
| WO | WO-2013/066601 A1 | 5/2013 |
| WO | WO-2014/112632 A1 | 7/2014 |
| WO | WO-2018/026838 A1 | 2/2018 |

OTHER PUBLICATIONS

Barros, et al., Multimodal Emotional State Recognition Using Sequence-Dependent Deep Hierarchical Features, Neural Networks, vol. 72, 2015, pp. 140-151 (Year: 2015).*

Andersson, V. and Araujo, R., Person Identification Using Anthropometric and Gait Data from Kinect Sensor, Proceedings of the AAAI Conference on Artificial Intelligence, 29(1):425-431 (2015).

Bertuletti, J. et al., Measurement of the inter-foot distance using a Time-of-Flight proximity sensor, 1-3 (2016).

Chen, C. et al., A Joint Estimation of Head and Body Orientation Cues in Surveillance Video, Idiap Research Institute, 8 pages (2011).

Environmental Protection Agency, Energy Star Program Requirements for Computers: Version 5.0, pp. 1-27 (2008).

International Search Report, PCT/US2017/044936, Systems and Methods to Identify Persons and/or Identify and Quantify Pain, Fatigue, Mood, and Intent With Protection of Privacy, Filed Aug. 1, 2017, ISA/US, 3 pages, Oct. 12, 2017.

Lee, M. W. and Nevatia, R., Human Pose Tracking in Monocular Sequence Using Multilevel Structured Models. IEEE Transactions on Pattern Analysis and Machine Intelligence, 31(1):27-38 (2009).

Moll, J., Person Re-Identification using RGB-Depth Cameras, Doctoral Thesis, pp. 1-142 (2015).

Munsell, B.C. et al., Person Identification Using Full-Body Motion and Anthropometric Biometrics from Kinect Videos, European Conference on Computer Vision, 91-100 (2012).

Sinha, A. et al., Kinect based People Identification System using Fusion of Clustering and Classification, International Conference on Computer Vision Theory and Applications, 3:171-179 (2014).

Sinha, A., et al., Pose Based Person Identification Using Kinect, IEEE International Conference on Systems, Man, and Cybernetics, 497-503 (2013).

Stone. E.E. and Skubic, M., Evaluation of an Inexpensive Depth Camera for Passive In-Home Fall Risk Assessment, 2011 5th International Conference on Pervasive Computing Technologies for Healthcare (PervasiveHealth) and Workshops, pp. 71-77 (2011).

Usabiaga, J. et al., Recognizing Simple Human Actions Using 3D Head Movement, Computational Intelligence, 23:484-496 (2007).

Written Opinion, PCT/US2017/044936, Systems and Methods to Identify Persons and/or Identify and Quantify Pain, Fatigue, Mood,

(56) References Cited

OTHER PUBLICATIONS and Intent With Protection of Privacy, Filed Aug. 1, 2017, ISA/US, 9 pages, Oct. 12, 2017.

* cited by examiner

Figure 5C

| Category | Examples of Static Features (not exhaustive) |
|---|---|
| • Body | • Height<br>• Shoulder-to-shoulder width at level of deltoid muscles<br>• 3D shape, 2D image, length, or width of body or parts, including:<br>    • Upper or lower arm (or both)<br>    • Upper or lower leg (or both)<br>    • Hand or foot<br>    • Head, neck, or torso<br>• Ratio between any two of the following:<br>    • Torso surface area<br>    • Torso volume<br>    • Length of head<br>    • Length of torso<br>    • Limb circumference |
| • Head | • Volume of:<br>    • Head<br>    • Nose<br>• Circumference of:<br>    • Head<br>    • Orbital socket<br>• Width of:<br>    • Head silhouette (viewed from front, side, or back)<br>    • Mouth<br>    • Chin<br>• Degree of curvature of:<br>    • Top or back of head<br>    • Chin<br>• Distance between any two of the following:<br>    • Glabella<br>    • Nasal bridge<br>    • Tip of nose<br>    • Philtrum<br>    • Pogonion<br>    • Pupil of eye<br>    • Ear external auditory canal<br>    • Ear pinna<br>    • Top of head<br>    • Environmental object (e.g., ground, furniture, wall) |
| • General | • Mathematical quantity/derivation of body portion or worn/held object<br>    • Eigenimage or eigenface<br>    • SIFT (scale-invariant feature transform)<br>    • HOG (histogram of oriented gradients).<br>    • Pixel mask or pixel count or voxel volume<br>    • Centroid, convex hull, or 3D mesh<br>    • Color, reflectance, texture, or pattern<br>    • Convolution<br>    • Weights of a neural network |

Figure 5D

| Category | Examples of Dynamic Features (not exhaustive) |
|---|---|
| • Body | • Rate of turn of body<br>• Walking speed (averaged over, e.g., several seconds)<br>• Maximum distance between the two feet during a stride<br>• Maximum angle of rotation at shoulder joint during a stride<br>• Difference of stride length between right leg and left leg<br>• Presence or absence of wheelchair<br>• Presence or absence of assistive device, such as a cane<br>• Presence or absence of a clothing color or reflectance<br>• Height of shoes (e.g., high heels)<br>• Angle of tilt or sway of body relative to ground<br>• Angle of bend between torso and legs<br>• Degree of spinal curvature<br>• Body temperature (e.g., during illness)<br>• Proximity to, or distance from, local furniture or wall<br>• Distance of body from sensor |
| • Head | • Orientation of head relative to torso<br>• Orientation of head relative to sensor<br>• Angle of gaze relative to sensor<br>• Presence or absence of glasses<br>• Presence of absence of hat or helmet<br>• Volume of hair |
| • General | • Rate of change of an angle, or of a distance, or of another feature<br>   • Pertaining to a single body portion<br>   • Between two body portions<br>   • Between a body portion and an environmental object<br>   • Between a body portion and a worn/held object<br>   • Between a worn/held object and an environmental object<br>• Differences between the weights/outputs of two neural networks, or of the same neural network at different points in time |

| Static feature | Value range |
|---|---|
| • Height | • 180-200 cm |
| • Head circumference | • 58-60 cm |
| Dynamic feature | Value range |
| • Avg. walking speed | • 0.5-1 meter/sec |
| • Presence of glasses | • Yes |

| Person identity |
|---|
| • Bob |
| Bodyprint-score |
| • 0.95 |

590

| Static feature | Value range |
|---|---|
| • Height | • 170-180 cm |
| • Ear-to-eye distance | • 14-16 cm |
| Dynamic feature | Value range |
| • Avg. walking speed | • 1-2 meter/sec |

| Person identity |
|---|
| • Clara |
| Bodyprint-score |
| • 0.80 |

Probabilities shown above are illustrative only.

N/A = not available

Figure 10

| Features | Relationships | Conclusions |
|---|---|---|
| • Head location | • Walking occurs when head translation > 0.1<br>• Footfalls occur at acceleration minima<br>• Stride length equals inter-footfall distance | • Is walking (D)<br>• Length of stride (Q) |
| • Posture<br>• Hand location | • Is seated, not ambulating<br>• Hand chest-to-head oscillation ≥ 5/min | • Is dining (D) |
| • Walk speed<br>• Spine angle | • Walk speed below a given threshold, and<br>• Spine angle above a given threshold | • Is fatigued (D) |
| • Walk speed<br>• Spine angle | • Compare current walk speed and spine angle to historical averages for this person | • Fatigue level is 4 out of 10 (Q) |
| • Time walking | • Time walking dropped a standard deviation | • Is depressed (D) |
| • Cane usage | • Cane usage doubled from prior week | • Is in pain (D) |
| • Posture<br>• Hand location<br>• Chin angle | • Time-to-stand is 3x higher than average<br>• Right hand stays near (clutches) abdomen<br>• Spike in frequency of downward gaze | • Pain level is 6 out of 10 (Q) |
| • Proximity<br>• Volume<br>• Location | • Stood near large object (disposal bin)<br>• Sudden volume decrease (took off pack)<br>• Quickly departed scene | • Possibly left dangerous object (D) |
| • Walk speed<br>• Gaze<br>• Chin angle | • Walk speed drops from normal to zero<br>• Gaze swivels back-and-forth<br>• Chin angle rises upward (sniffing) | • Possibly found warning sound or smell (D) |
| • Posture<br>• Gross activity<br>• Gaze | • Is seated, not ambulating<br>• Almost no movement in past ten mins<br>• Gaze directed downward for past ten mins | • Is sleeping at desk (D) |
| • Posture<br>• Hand location | • Speed of sit-to-stand up 5% over 10 days<br>• Height of arm raise up 10% over 10 days | • Illness recovery is 15% (Q) |
| • 3D body morphology | • Convolutions, weights, and/or other mathematical descriptors (e.g., neural net) | • Has hostile intent (D) |
| • 3D facial morphology | • Convolutions, weights, and/or other mathematical descriptors (e.g., neural net) | • Is surprised or scared (Q) |

D = detection    Q = quantification

SYSTEMS AND METHODS TO IDENTIFY PERSONS AND/OR IDENTIFY AND QUANTIFY PAIN, FATIGUE, MOOD, AND INTENT WITH PROTECTION OF PRIVACY

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

PRIORITY APPLICATIONS

This application is a continuation of U.S. patent application Ser. No. 15/666,514, filed Aug. 1, 2017, which claims the benefit of U.S. Provisional Patent Application Ser. No. 62/370,083 filed on Aug. 2, 2016, and U.S. Provisional Patent Application Ser. No. 62/438,229, filed on Dec. 22, 2016, the contents of which are hereby incorporated by reference herein in their entirety.

FIELD OF THE INVENTION

This invention relates generally to systems and methods to identify persons using sensor-based data and/or to characterize mental perceptions (e.g., pain, fatigue, mood) and/or intent (e.g., to perform an action) using measurements of a human body (e.g., of physical attributes and motion), all while protecting the privacy of said persons.

BACKGROUND OF THE INVENTION

The challenge of identifying persons from photographs, real-time images, and many other types of sensor-based data is relevant to a variety of industries and applications. For example, the problem is ubiquitous in the security industry where persons may need to be screened for access to controlled areas, or labeled as a threat based on prior contact.

Many current identification methods rely on facial or fingerprint recognition to provide a unique identification of a person. These methods may enable accurate identification within a certain range of operational parameters or conditions but are dramatically degraded or non-functional outside their fairly strict set of operating conditions. For example, facial recognition is not robust to variation in lighting (e.g., low-light or total darkness). The accuracy of facial recognition typically degrades with increasing distance from camera to subject (e.g., there is insufficient resolution to discern facial attributes). Furthermore, if a person is facing away from the camera, facial recognition fails altogether. Similarly, proximity-based biometric techniques, such as fingerprint recognition and retinal scans, become impossible in applications that require the identification of persons from more than a few centimeters away.

Many current identification methods work properly only when a person adopts a narrow location, position, or stance. For example, acquiring a fingerprint requires that a specific finger be placed directly adjacent to a specific sensor. For example, face-recognition login systems for laptops require that the face be within a pre-specified close range of the computer camera. As a result, many current identification methods struggle to identify a person when that person is moving about the environment normally, i.e., not deliberately presenting himself/herself to a sensor.

Privacy concerns are particularly daunting for some methods of person identification. For example, methods that rely on the visual data of a person's face or body may expose information beyond what is needed specifically for person identification, such as what clothing is worn, or what material is read or viewed. Attempts to obfuscate or hide visual images by known methods may still be susceptible to "reverse engineering", whereby visual images are mathematically reconstructed.

Occlusion and field-of-view impose further limits on some methods of person identification. For example, methods that rely on gait (walking pattern) or silhouette (outline) of a person may depend on the availability of a specific field-of-view (e.g., a non-occluded field-of-view), a specific person orientation (e.g., relative to the sensor), or the availability of a specific feature (e.g., attribute or property). When any of these prerequisites are unavailable or fail to uniquely identify a specific person, such methods are prone to failure, especially in uncontrolled (e.g., untidy or transitory) environments such as a person's home. Person identification based on motion (e.g., gait) presents additional challenges because physical measurements of motion can be subtle and difficult to accomplish in a real-world setting.

Present-day methods to characterize the motion of an individual often draw upon either one-dimensional data streams (e.g., an infrared beam which is "broken" when someone crosses it); two-dimensional data streams (e.g., webcam photos or videos); or three-dimensional data streams (e.g., depth images, in which each pixel of the image corresponds to the real-world distance from the sensor to some portion of an object in the field-of-view). In these various data streams, so-called "features"—that is, computational characteristics of interest—may be identified, such as anatomic landmarks on a person's face. We refer herein to features that are relatively constant as "static" (e.g., eye-to-eye distance) and to features that change appreciably over time as "dynamic" (e.g., angle of eye-gaze relative to sensor).

Present-day methods to characterize motion often rely on tracking the spatial location of static features, such as those obtained by facial recognition. However, in many cases, these methods are insufficient for the characterization of complex motion. Examples of complex motion include ambulation (e.g., walking speed, stride length, or postural angle from vertical) and synchronized activity (e.g., eating, sitting, or gesticulating at another person).

Because complex motion evolves over time, and may consist of several different stages or sub-parts, its characterization requires data acquisition over time. However, acquiring data for complex motion over a duration of time presents many additional challenges. For example, the acquired datasets may become so sizable that they are difficult to store or transmit. For example, an extended duration of data acquisition may be perceived as invasive of privacy by users, especially if the sensor is placed at home, or must be worn.

In addition, current approaches to acquiring data about human motion are subject to drawbacks. Wearable sensors suffer from low signal-to-noise, limited modalities (e.g., types of data that can be acquired), and the need for users to wear, remember, and recharge them. For example, a wrist-worn wearable sensor cannot detect the angle of a user's spine relative to horizontal. Fixed instrumentation (e.g., high-speed cameras, sensor-embedded walking mats, and body-motion suits) suffers from the drawbacks of high cost, large size, inconvenience, and the inability to operate in uncontrolled or obstructed environments. For example, it is difficult and inconvenient to place a sensor-embedded walking mat of any considerable size in a person's home.

Therefore, person-identification methods are needed which are robust to uncontrolled environments, effective at a distance, and protective of personal privacy.

In addition to identifying a person, the ability to further identify and characterize the mental perceptions or intentions of a person has applications in, for example, healthcare (e.g., disease detection and progression), security (e.g., theft and sabotage), and industrial (e.g., safety and productivity) settings. However, many of these properties are impervious to direct measurement using existing technologies.

The healthcare industry needs an objective measure of fatigue. The ability to quantify fatigue permits gauging the severity and progression of a wide variety of diseases (e.g., multiple sclerosis, depression, cancer, and many other maladies), especially during a passage of time. Currently, the only way to estimate a level of fatigue is through patient reports, such as interviews or questionnaires ("How tired do you feel today on a scale of 1 to 5?"). The qualitative impressions furnished by such reports are labor-intensive to obtain; virtually impossible to compare and contrast across different patients; and are subject to perception bias, recall bias, and various types of manipulation, conscious or otherwise. An objective measure of fatigue would be transformative for the monitoring and treatment of many illnesses by providing reliable and consistent metrics throughout diagnosis, evaluation, and treatment.

The healthcare industry also needs an objective measure of pain, for reasons similar to those described above for fatigue. In particular, the ability to track pain permits gauging the need for, and dosage of, pain medications. Many pain medications, because they are addictive, are associated with abuse and fraud. Tracking accurate levels of real-world pain, particularly in response to drug administration, would allow such abuse and fraud to be detected and countered.

The security, military, factory, and retail industries would all benefit from the ability to identify and quantify (e.g., detect) intent. Some examples (out of myriad possibilities) include the ability to automatically sense that a person may be observing an area, in unusual detail, or in an unusual way, as if in preparation for a future attack; or that a person has abandoned a suspicious item, such as a backpack; or that a person has surreptitiously swapped an item, such as a prohibited tool, with another person; or that a person has suddenly noticed a warning signal, such as an odor or a sound, that could indicate a danger in a factory; or that a person has become attentive to a particular object, such as a retail display.

To access the benefits described above, methods and systems are needed that can detect and/or quantify mental perception and intent via sensor data, in a reliable, precise, convenient, and non-invasive manner in real-world settings.

SUMMARY OF THE INVENTION

Disclosed herein are methods and systems to identify persons and/or characterize their mental perceptions and intent via sensor measurements of physical body features and/or motion. The disclosed technology can accurately identify persons without exposing private information (e.g., the person's visual appearance, state of dress, what he/she is reading or watching on TV, etc.), allowing the preservation of personal privacy. Compared to previous approaches, the disclosed technology can more accurately identify persons using multiple physical attributes or motions (e.g., height or walking speed). This approach removes the dependency and associated disadvantages of relying on any single physical attribute, especially an attribute which might change over time or become obstructed from view by the sensor. In contrast, previous approaches require that measurements be performed under more limited physical constraints, and they rely on a smaller set of physical attributes (e.g., facial recognition typically fails when the subject is not facing the camera and only utilizes static facial features).

Moreover, the disclosed technology can utilize partial or incomplete measurements of one or more physical attributes, making it more robust to real-world (noisy, uncontrolled) settings. For example, the disclosed technology may identify a person when they are facing the disclosed technology; or when they are facing away from the disclosed technology; or when they are partially occluded (by furniture, say) in relation to the disclosed technology. For example, the disclosed technology may describe a measurement of fatigue that remains consistent if the person is visible to the disclosed technology frequently at some times, but sporadically at other times; or if the person's face is sometimes occluded and at other times unoccluded.

The disclosed technology can be used to identify and quantify mental perceptions (pain, fatigue, mood) and intent (e.g., to perform an action) by characterizing the movement, activity, and/or behavior of a person via sensor measurements of the person's body. Mental perceptions and intentions are largely impervious to existing technologies. In the approach disclosed herein, these properties may nonetheless be detected and quantified indirectly, proxied via measurements of a person's physical posture and movement. Among other advancements, the disclosed technology establishes a capability to acquire novel movement-related biomarkers of disease.

The physical measurements disclosed herein may be either "direct" (that is, an immediate result of a sensor's interaction with the person's body); or "indirect" (that is, derived from other measurements, which may in turn be direct or indirect). The sensor data, from which the physical measurements are obtained, may be either real-time or stored, and may be collected whether or not the line-of-sight between the sensor and the person is empty or occluded. These measurements need not be contiguous, adjacent, complete, consistent, or sequential, and may be calculated retroactively as well as prospectively.

The disclosed technology, in certain embodiments, includes a method of identifying representations of one or more persons-of-interest from sensor data containing representations of a surrounding environment with persons therein, the method comprising: (a) receiving, by a processor of a computing device, sensor data (e.g., depth data) from one or more frames, wherein the sensor data comprises representations of persons and representations of the surrounding environment, wherein the representations of persons comprise representations of the one or more persons-of-interest; (b) segmenting, by the processor, the sensor data into distinct representations of each of the persons in the sensor data, such that each representation of a person within the sensor data is associated with a respective segmentation of the sensor data, thereby distinguishing representations of each of the persons from representations of the surrounding environment in the sensor data; (c) isolating, by the processor, one or more body portions from each segmentation of the sensor data; (d) determining, by the processor, for each segmentation of the sensor data, a measure for each of one or more features associated with the respective representation of the person based on the one or more isolated body portions of the respective segmentation of the sensor data;

(e) determining, by the processor, for each segmentation of the sensor data, whether a combination of the determined measure(s) of the one or more features associated with the respective representation of the person correspond (e.g., within a confidence threshold if applicable) to a bodyprint of one of the one or more persons-of-interest, thereby identifying the respective segmentation of the sensor data as a person-of-interest; and (f) storing, by the processor, the segmentation of data associated with the respective representation of the person that corresponds to the bodyprint of the one of the one or more persons-of-interest such that said segmentation of data is associated with an identity of the corresponding person-of-interest.

In certain embodiments, segmenting, by the processor, the sensor data into distinct representations of each of the persons in the sensor data comprises performing a machine learning and/or pattern recognition technique (e.g., a Convolutional Neural Network, Random Forest, Support Vector Machine, naïve Bayesian machine, and/or clustering technique) (e.g., either explicitly or implicitly).

In certain embodiments, isolating, by the processor, the one or more body portions from each segmentation of the sensor data comprises performing a machine learning and/or pattern recognition technique (e.g., a Convolutional Neural Network, Random Forest, Support Vector Machine, naïve Bayesian machine, and/or clustering technique) (e.g., either explicitly or implicitly).

In certain embodiments, each of the one or more persons-of-interest are registered for identification.

In certain embodiments, identifying the respective segmentation is based on the output of a classifier.

In certain embodiments, identifying the respective segmentation is based on a rule or a category or a heuristic (e.g., a mathematical calculation such as a dot-product, or a cutoff threshold such as a height).

In certain embodiments, the method includes storing, for each of the one or more persons-of-interest, by the processor in a memory device, an identity and a bodyprint (e.g., only the bodyprints of persons-of-interest are stored in memory; bodyprints of persons that are not persons-of-interest are not stored in memory), wherein each bodyprint comprises a set of features combined with a range of measures for each of those features which together are specific to a respective person-of-interest within the one or more persons-of-interest, and each identity is associated with a bodyprint.

In certain embodiments, the method includes comparing, by the processor, the determined measure(s) of the respective one or more features and measure(s) from a corresponding subset of the set of features of each bodyprint to determine whether the determined measure(s) of the respective one or more features are within the range of measures for the corresponding subset of features of a bodyprint.

In certain embodiments, no greater than one person, no greater than two people, no greater than three people, no greater than four people, no greater than five people, no greater than six people, no greater than ten people, no greater than twenty-five people, no greater than fifty people, no greater than one-hundred people are registered for identification.

In certain embodiments, facial features are omitted from the sensor data.

In certain embodiments, all visual data is omitted from the sensor data.

In certain embodiments, at least one of the persons is identified as "other."

In certain embodiments, isolating one or more body portions comprises determining, by the processor, which body portions in each segmentation of sensor data to isolate based on at least one property selected from the group consisting of a nature of the data set, a type of the sensor, an amount of non-occluded (i.e., "visible") data available for the person, availability of representations of body portions within the segmentation of sensor data, availability of bodyprints for persons-of-interest, and a library of features available for calculation.

In certain embodiments, the one or more body portions may differ from person-to-person within a frame.

In certain embodiments, the one or more measures comprise one or more members selected from the group consisting of: an area, a volume, a circumference, a closed curve, an unclosed curve, a length, a spatial location, an angle, an image (which may be 2D), a morphology/shape (which may be 3D), an intensity, a filtered output, a set of numerical weights, a mathematical scaling, a mathematical transformation, a mathematical convolution, a generalized mathematical operation, or a rate of change of any of the preceding.

In certain embodiments, the method includes, for each person, selecting a subset from a set of one or more candidate features (e.g., based on a library of features and available sensor data) for which measures are to be determined for each person in a frame.

In certain embodiments, at least one of the one or more features is unavailable or non-computable in any given frame or series of frames.

In certain embodiments, each of the one or more features is calculated based on one or more frames.

In certain embodiments, the one or more frames comprise a plurality of contiguous or non-contiguous frames.

In certain embodiments, the one or more features comprise one or more static features.

In certain embodiments, the one or more static features comprise one or more members selected from the group consisting of: person height; shoulder-to-shoulder width; length or width of upper arm, lower arm, upper leg, lower leg, hand, foot, head, neck or torso; ratio between any two of: torso surface area, torso volume, length of head, length of torso, limb circumference; volume of head or nose; circumference of head or orbital socket; width of head silhouette, mouth, or chin; degree of curvature of top or back of head or chin; and distance between any two of: *glabella*, nasal bridge, tip of nose, philtrum, pogonion, pupil of eye, ear external auditory canal, ear pinna, top of head, the ground, image (which may be 2D) of a body portion, morphology/shape (which may be 3D) of a body portion, eigenimage, eigenface, scale-invariant feature transform, histogram of oriented gradients, pixel mask, pixel count, voxel volume, centroid, convex hull, 3D mesh, color, reflectance, texture, pattern, convolution.

In certain embodiments, the one or more static features comprise one or more members selected from the group consisting of: weights and/or outputs of a neural network, including Convolutional Neural Network; weights and/or outputs of a neural network at different points in time, including a Convolutional Neural Network; weights and/or outputs of a Random Forest; weights and/or outputs of a Support Vector Machine; weights and/or outputs of a naïve Bayesian machine; clustering, including K-means clustering; supervised learning; unsupervised learning.

In certain embodiments, each feature is calculated based on measurements of attributes of a single body portion, or the relationship between measurements of attributes of different body portions, or the relationship between measurements of the attributes of one or more body portions and measurements of the environment.

In certain embodiments, the attributes of the single body portion comprise one or more members selected from the group consisting of: person height; length or width of upper arm, lower arm, upper leg, lower leg, hand, foot, head, neck, or torso; volume of head or nose; circumference of head or orbital socket; width of head silhouette, mouth, or chin; degree of curvature of top or back of head or chin.

In certain embodiments, the relationship between measurements of attributes of different body portions comprises a ratio between any two of: torso surface area, torso volume, length of head, length of torso, limb circumference; distance between any two of: *glabella*, nasal bridge, tip of nose, philtrum, pogonion, pupil of eye, ear external auditory canal, ear pinna, top of head, the ground.

In certain embodiments, the one or more features comprise one or more dynamic features.

In certain embodiments, the one or more dynamic features comprise one or more members selected from the group consisting of: rate of turn of body; walking speed (instantaneous or average); maximum distance between the two feet during a stride; maximum angle of rotation at shoulder joint during a stride; difference of stride length between right leg and left leg; presence or absence of wheelchair; presence of absence of assistive device, such as a cane; presence or absence of a clothing color or reflectance; height of shoes (e.g., high heels); angle of tilt or sway of body relative to ground; angle of bend between torso and legs; degree of spinal curvature; body temperature (e.g., during illness); proximity to, or distance from, local furniture or wall; distance of body from sensor; orientation of head relative to torso; orientation of head relative to sensor; angle of gaze relative to sensor; presence or absence of glasses; presence or absence of hat or helmet; and volume of hair.

In certain embodiments, the one or more dynamic features comprise one or more members selected from the group consisting of: weights and/or outputs of a neural network, including Convolutional Neural Network; weights and/or outputs of a neural network at different points in time, including a Convolutional Neural Network; weights and/or outputs of a Random Forest; weights and/or outputs of a Support Vector Machine; weights and/or outputs of a naïve Bayesian machine; clustering, including K-means clustering; supervised learning; unsupervised learning.

In certain embodiments, each of the one or more dynamic features is calculated based on at least one of 1) to 3) as follows: 1) the variation of attributes of a single body portion over time, space, or other measurement unit of interest (e.g., head turn, hand raise, body temperature, shape or size of a body portion, or orientation of a body joint relative to the sensor), 2) the variation of the relationship between features of different body portions over time, space, or other measurement unit of interest (e.g., overall body orientation relative to the sensor), and 3) the variation of the environment or its relationship to different body segments of the person over time, space, or other measurement unit of interest (e.g., frequency of the person in proximity to a particular chair in the room or distance of the person to the sensor).

In certain embodiments, the identity is a rule-in identification (e.g., "this person is probably Bob").

In certain embodiments, the identity is a rule-out aka "other" identification (e.g., "this person is probably not Bob").

In certain embodiments, the one or more features are captured from a different frame or set of frames in the sensor data than the one or more features used to identify another person.

In certain embodiments, for each person, the identity is determined based on a set of features, and on a range of measures for each of those features, which combined are highly specific to a particular person (e.g., within the set of persons whose bodyprints are known to the system).

In certain embodiments, for each person, the identity is determined based at least in part on a fidelity and/or predictive power of the one or more features used to perform that identification (e.g., how well the feature can be measured; confidence in measurement of the feature; specificity of that feature to a single person).

In certain embodiments, the one or more features vary over time based on at least one member selected from the group consisting of: an available scene, the sensor, the sensor data, the library of known bodyprints, and the library of known and computable features.

In certain embodiments, the one or more features and/or bodyprints are automatically calculated by a machine learning and/or pattern recognition technique (e.g., a Convolutional Neural Network, Random Forest, Support Vector Machine, naïve Bayesian machine, and/or clustering technique).

In certain embodiments, the one or more features and/or bodyprints are provided as a priori or a posteriori information by an external agent, such as manual tagging.

In certain embodiments, the one or more features and/or bodyprints can be updated or modified over time.

In certain embodiments, the method includes acquiring, by a sensor (e.g., placed in a room of a building, such as a person's home), sensor data (corresponding to a given field-of-view), wherein the sensor data comprises a plurality of frames and each frame is represented as a two-dimensional spatial map of pixels (e.g., a matrix), with an intensity value of each pixel corresponding to a projected distance from the sensor (i.e., the horizontal distance between a first vertical plane passing through the sensor and a second vertical plane passing through an object in the scene).

In certain embodiments, the method includes prioritizing, by the processor, the one or more features, wherein said prioritizing comprises aggregating features across at least one member selected from the group consisting of different sensors, different times, different bodyprints, and different spatial locations.

In certain embodiments, the one or more features differ from person-to-person within the same scene.

In certain embodiments, the one or more features have different assignations from frame-to-frame even for the same person.

In certain embodiments, the sensor data comprises data acquired by at least one of time-of-flight light detection and ranging, or by projecting at least one energy pattern onto the scene and measuring the pattern's deformation.

In certain embodiments, the sensor data comprises data acquired using light (e.g., electromagnetic radiation) or sound (e.g., acoustic data).

In certain embodiments, the sensor data comprises at least one data type selected from the group consisting of: raw sensor data, values derived from raw sensor data (e.g., skeleton data, in which the joints of a person's skeleton are estimated, and pixel-label data, in which each pixel of a data-collection is assigned to either zero or one person), and trajectory data (e.g., the changing location of a person over time).

In certain embodiments, each of the one or more frames corresponds to a "snapshot" consisting of one or more data streams comprising data acquired either preceding, or at, a particular moment in time.

In certain embodiments, the one or more frames comprise at least one of multiple frames taken by a single sensor at multiple points in time, or of multiple frames taken by multiple sensors at the same or at different points in time.

In certain embodiments, the method includes determining, by the processor, a confidence score for each person identified.

In certain embodiments, the method includes discarding, by the processor, a subset of the sensor data associated with a person (e.g., an "other" person).

In certain embodiments, the identity comprises an unknown identification.

In certain embodiments, the method includes adjusting, by the processor, the one or more features to ensure that all features are temporally and/or spatially collocated (in an effort to 'align' observations).

In certain embodiments, at least one of the one or more features is offset-corrected, latency-corrected, or spatially collocated, in order to adjust for timing delays or biases in the sensors or in calculation methodologies.

In certain embodiments, the fidelity of a feature depends on at least one member selected from the group consisting of the composition of the scene (i.e., the field-of-view and the objects within it), the type of sensor being utilized, and the type of data being acquired.

In certain embodiments, identifying is performed while the person is moving about naturally (e.g., walking, turning, performing an activity).

In certain embodiments, identifying is performed in real-time or close to real-time.

In certain embodiments, identifying is performed after a delay, or equivalently, at a time substantially different than the time at which data acquisition occurred.

In certain embodiments, identifying is performed retrospectively (i.e., "rewinding" through previously-acquired data).

In certain embodiments, the person is located at a distance greater than 0.1 meter, greater than 0.5 meter, greater than 1 meter, greater than 2 meters, greater than 5 meters, from the sensor.

The disclosed technology, in certain embodiments, includes a system for identifying representations of one or more persons-of-interest from sensor data containing representations of a surrounding environment with persons therein, the system comprising: a processor; and a memory storing instructions thereon, wherein the instructions, when executed by the processor, cause the processor to: segment sensor data (e.g., depth data) from one or more frames into distinct representations of each of the persons in the sensor data, such that each representation of a person within the sensor data is associated with a respective segmentation of the sensor data, thereby distinguishing the representations of each of the persons from representations of the surrounding environment in the sensor data, wherein the sensor data comprises representations of persons and representations of the surrounding environment, wherein the representations of persons comprise representations of the one or more persons-of-interest; isolate one or more body portions from each segmentation of the sensor data; determine, for each segmentation of the sensor data, a measure for each of one or more features associated with the respective representation of the person based on the one or more isolated body portions of the respective segmentation of the sensor data; determine, for each segmentation of the sensor data, whether a combination of the determined measure(s) of the one or more features associated with the respective representation of the person correspond (e.g., within a confidence threshold if applicable) to a bodyprint of one of the one or more persons-of-interest, thereby identifying the respective segmentation of the sensor data as a person-of-interest; and store the segmentation of data associated with the respective representation of the person that corresponds to the bodyprint of the one of the one or more persons-of-interest such that said segmentation of data is associated with an identity of the corresponding person-of-interest.

In certain embodiments, the instructions, when executed by the processor, cause the processor to perform a machine learning and/or pattern recognition technique (e.g., a Convolutional Neural Network, Random Forest, Support Vector Machine, naïve Bayesian machine, and/or clustering technique) (e.g., either explicitly or implicitly) to segment the sensor data into distinct representations of each of the persons in the sensor data.

In certain embodiments, the instructions, when executed by the processor, cause the processor to perform a machine learning and/or pattern recognition technique (e.g., a Convolutional Neural Network, Random Forest, Support Vector Machine, naïve Bayesian machine, and/or clustering technique) (e.g., either explicitly or implicitly) to isolate the one or more body portions from each segmentation of the sensor data.

In certain embodiments, each of the one or more persons-of-interest are registered for identification.

In certain embodiments, identifying the respective segmentation is based on the output of a classifier.

In certain embodiments, identifying the respective segmentation is based on a rule or a category or a heuristic (e.g., a mathematical calculation such as a dot-product, or a cutoff threshold such as a height).

In certain embodiments, the instructions, when executed by the processor, cause the processor to store, for each of the one or more persons-of-interest, in a memory device, an identity and a bodyprint (e.g., only the bodyprints of persons-of-interest are stored in memory; bodyprints of persons that are not persons-of-interest are not stored in memory), wherein each bodyprint comprises a set of features combined with a range of measures for each of those features which together are specific to a respective person-of-interest within the one or more persons-of-interest, and each identity is associated with a bodyprint.

In certain embodiments, the instructions, when executed by the processor, cause the processor to compare the determined measure(s) of the respective one or more features and measures(s) from a corresponding subset of the set of features of each bodyprint to determine whether the determined measure(s) of the respective one or more features are within the range of measures for the corresponding subset of features of a bodyprint.

In certain embodiments, no greater than one person, no greater than two people, no greater than three people, no greater than four people, no greater than five people, no greater than six people, no greater than ten people, no greater than twenty-five people, no greater than fifty people, no greater than one-hundred people are registered for identification.

In certain embodiments, facial features are omitted from the sensor data.

In certain embodiments, all visual data is omitted from the sensor data.

In certain embodiments, at least one of the persons is identified as "other."

In certain embodiments, the instructions, when executed by the processor, cause the processor to determine which body portions in each segmentation of sensor data to isolate based on at least one property selected from the group consisting of: a nature of the data set, a type of the sensor, an amount of non-occluded (i.e., "visible") data available for the person, availability of representations of body portions within the segmentation of sensor data, availability of body-prints for persons-of-interest, and a library of features available for calculation.

In certain embodiments, the one or more body portions that are isolated may differ from person-to-person within a frame.

In certain embodiments, each of the one or more measure(s) of the one or more features comprise one or more members selected from the group consisting of: an area, a volume, a circumference, a closed curve, an unclosed curve, a length, a spatial location, an angle, an image (which may be 2D), a morphology/shape (which may be 3D), an intensity, a filtered output, a set of numerical weights, a mathematical scaling, a mathematical transformation, a mathematical convolution, a generalized mathematical operation, or a rate of change of any of the preceding.

In certain embodiments, the instructions, when executed by the processor, cause the processor to, for each person, determine which features (e.g., based on a library of features and available sensor data) can and should be calculated for each person in a frame.

In certain embodiments, at least one of the one or more features is unavailable or non-computable in any given frame or series of frames.

In certain embodiments, each of the one or more features is calculated based on one or more frames.

In certain embodiments, the one or more frames comprise a plurality of contiguous or non-contiguous frames.

In certain embodiments, the one or more features comprise one or more static features.

In certain embodiments, the one or more static features comprise one or more members selected from the group consisting of: person height; shoulder-to-shoulder width; length or width of upper arm, lower arm, upper leg, lower leg, hand, foot, head, neck or torso; ratio between any two of: torso surface area, torso volume, length of head, length of torso, limb circumference; volume of head or nose; circumference of head or orbital socket; width of head silhouette, mouth, or chin; degree of curvature of top or back of head or chin; and distance between any two of: glabella, nasal bridge, tip of nose, philtrum, pogonion, pupil of eye, ear external auditory canal, ear pinna, top of head, the ground, image (which may be 2D) of a body portion, morphology/shape (which may be 3D) of a body portion, eigenimage, eigenface, scale-invariant feature transform, histogram of oriented gradients, pixel mask, pixel count, voxel volume, centroid, convex hull, 3D mesh, color, reflectance, texture, pattern, convolution.

In certain embodiments, the one or more static features comprise one or more members selected from the group consisting of: weights and/or outputs of a neural network, including Convolutional Neural Network; weights and/or outputs of a neural network at different points in time, including a Convolutional Neural Network; weights and/or outputs of a Random Forest; weights and/or outputs of a Support Vector Machine; weights and/or outputs of a naïve Bayesian machine; clustering, including K-means clustering; supervised learning; unsupervised learning.

In certain embodiments, each of the one or more features is calculated based on measurements of attributes of a single body portion, or the relationship between measurements of attributes of different body portions, or the relationship between measurements of the attributes of one or more body portions and measurements of the environment.

In certain embodiments, attributes of the single body portion comprise one or more members selected from the group consisting of: person height; length or width of upper arm, lower arm, upper leg, lower leg, hand, foot, head, neck, or torso; volume of head or nose; circumference of head or orbital socket; width of head silhouette, mouth, or chin; degree of curvature of top or back of head or chin.

In certain embodiments, the relationship between measurements of attributes of different body portions comprises a ratio between any two of: torso surface area, torso volume, length of head, length of torso, limb circumference; distance between any two of: glabella, nasal bridge, tip of nose, philtrum, pogonion, pupil of eye, ear external auditory canal, ear pinna, top of head, the ground.

In certain embodiments, the one or more features comprise one or more dynamic features.

In certain embodiments, the one or more dynamic features comprise one or more members selected from the group consisting of: rate of turn of body; walking speed (instantaneous or average); maximum distance between the two feet during a stride; maximum angle of rotation at shoulder joint during a stride; difference of stride length between right leg and left leg; presence or absence of wheelchair; presence of absence of assistive device, such as a cane; presence or absence of a clothing color or reflectance; height of shoes (e.g., high heels); angle of tilt or sway of body relative to ground; angle of bend between torso and legs; degree of spinal curvature; body temperature (e.g., during illness); proximity to, or distance from, local furniture or wall; distance of body from sensor; orientation of head relative to torso; orientation of head relative to sensor; angle of gaze relative to sensor; presence or absence of glasses; presence or absence of hat or helmet; and volume of hair.

In certain embodiments, the one or more dynamic features comprise one or more members selected from the group consisting of: weights and/or outputs of a neural network, including Convolutional Neural Network; weights and/or outputs of a neural network at different points in time, including a Convolutional Neural Network; weights and/or outputs of a Random Forest; weights and/or outputs of a Support Vector Machine; weights and/or outputs of a naïve Bayesian machine; clustering, including K-means clustering; supervised learning; unsupervised learning.

In certain embodiments, each of the one or more dynamic features is calculated based on at least one of 1) to 3) as follows: 1) the variation of attributes of a single body portion over time, space, or other measurement unit of interest (e.g., head turn, hand raise, body temperature, shape or size of a body portion, or orientation of a body joint relative to the sensor), 2) the variation of the relationship between features of different body portions over time, space, or other measurement unit of interest (e.g., overall body orientation relative to the sensor), and 3) the variation of the environment or its relationship to different body segments of the person over time, space, or other measurement unit of interest (e.g., frequency of the person in proximity to a particular chair in the room or distance of the person to the sensor).

In certain embodiments, the identity is a rule-in identification (e.g., "this person is probably Bob").

In certain embodiments, the identity is a rule-out aka "other" identification (e.g., "this person is probably not Bob").

In certain embodiments, the one or more features are captured from a different frame or set of frames in the sensor data than the one or more features used to identify another person.

In certain embodiments, for each person, the identity is determined based on a set of features, and on a range of measures for each of those features, which combined are highly specific to a particular person (e.g., within the set of persons whose bodyprints are known to the system).

In certain embodiments, the identity is determined based at least in part on a fidelity and/or predictive power of the one or more features used to perform that identification (e.g., how well the feature can be measured; confidence in measurement of the feature; specificity of that feature to a single person).

In certain embodiments, the one or more features vary over time based on at least one member selected from the group consisting of: an available scene, the sensor, the sensor data, the library of known bodyprints, and the library of known and computable features.

In certain embodiments, the one or more features and/or bodyprints are automatically calculated by a machine learning or pattern recognition technique (e.g., a Convolutional Neural Network, Random Forest, Support Vector Machine, naïve Bayesian machine, and/or clustering technique).

In certain embodiments, the one or more features and/or bodyprints are provided as a priori or a posteriori information by an external agent, such as manual tagging.

In certain embodiments, the one or more features and/or bodyprints can be updated or modified over time.

In certain embodiments, the sensor data is acquired by a sensor (e.g., placed in a room of a building, such as a person's home), wherein the sensor data comprises a plurality of frames and each frame is represented as a two-dimensional spatial map of pixels (e.g., a matrix), with an intensity value of each pixel corresponding to a projected distance from the sensor (i.e., the horizontal distance between a first vertical plane passing through the sensor and a second vertical plane passing through an object in the scene).

In certain embodiments, the instructions, when executed by the processor, cause the processor to prioritize the one or more features, thereby aggregating features across at least one member selected from the group consisting of different sensors, different times, different bodyprints, and different spatial locations.

In certain embodiments, the one or more features differ from person-to-person within the same scene.

In certain embodiments, the one or more features have different assignments from frame-to-frame even for the same person.

In certain embodiments, the sensor data comprises data acquired by at least one of time-of-flight light detection and ranging, or by projecting at least one energy pattern onto the scene and measuring the pattern's deformation.

In certain embodiments, the sensor data comprises data acquired using light (e.g., electromagnetic radiation) or sound (e.g., acoustic data).

In certain embodiments, the sensor data comprises at least one data type selected from the group consisting of: raw sensor data, values derived from raw sensor data (e.g., skeleton data, in which the joints of a person's skeleton are estimated, and pixel-label data, in which each pixel of a data-collection is assigned to either zero or one person), or trajectory data (e.g., the changing location of a person over time).

In certain embodiments, each of the one or more frames corresponds to a "snapshot" consisting of one or more data streams comprising data acquired either preceding, or at, a particular moment in time.

In certain embodiments, the one or more frames comprise at least one of multiple frames taken by a single sensor at multiple points in time, or of multiple frames taken by multiple sensors at the same or at different points in time.

In certain embodiments, the instructions, when executed by the processor, cause the processor to determine a confidence score for each person identified.

In certain embodiments, the instructions, when executed by the processor, cause the processor to discard a subset of the sensor data associated with a person (e.g., an "other" person).

In certain embodiments, the identity comprises an unknown identification.

In certain embodiments, the instructions, when executed by the processor, cause the processor to adjust the one or more features to ensure that all features are temporally and/or spatially collocated (in an effort to 'align' observations).

In certain embodiments, at least one of the one or more features is offset-corrected, latency-corrected, or spatially collocated, in order to adjust for timing delays or biases in the sensors or in calculation methodologies.

In certain embodiments, the fidelity of a feature depends on at least one member selected from the group consisting of the composition of the scene (i.e., the field-of-view and the objects within it), the type of sensor being utilized, and the type of data being acquired.

In certain embodiments, identifying the respective segmentation is performed while the person is moving about naturally (e.g., walking, turning, performing an activity).

In certain embodiments, identifying the respective segmentation is performed in real-time or close to real-time.

In certain embodiments, identifying the respective segmentation is performed after a delay, or equivalently, at a time substantially different than the time at which data acquisition occurred.

In certain embodiments, identifying the respective segmentation is performed retrospectively (i.e., "rewinding" through previously-acquired data).

In certain embodiments, the person is located at a distance greater than 0.1 meter, greater than 0.5 meter, greater than 1 meter, greater than 2 meters, greater than 5 meters, from the sensor.

In certain embodiments, the system further comprises an infrared time-of-flight sensor for acquiring the sensor data.

In certain embodiments, the system further comprises a display and a housing for the processor and memory.

The disclosed technology, in certain embodiments, includes a method of real-time or near-real-time identification of one of a discrete set of pre-registered human individuals in a sensor field based at least in part (or exclusively) on depth data (e.g., one or more depth maps [e.g., a time series of depth maps] obtained by one or more sensors, e.g., one or more in-room sensors) (e.g., without the use of images that, if viewed or analyzed in isolation without prior registration, would provide a positive identification of the individual, e.g., without the use of photographic still or video images, thereby protecting personal privacy of the individual), the method comprising: quantifying, by a processor of a computing device, each of a plurality of features characteristic of a human detected within the sensor field (e.g., wherein the plurality of features comprises at least one static feature (e.g., height, leg length, shoulder-to-shoulder width, the weights and/or outputs of a machine learning and/or pattern recognition technique [e.g., a Convolutional Neural Network, Random Forest, Support Vector Machine, naïve Bayesian machine, and/or clustering technique]) and/or at least one dynamic feature (e.g., angle-of-gaze, walking speed, head silhouette width, the weights and/or outputs of a machine learning and/or pattern recognition technique [e.g., a Convolutional Neural Network, Random Forest, Support Vector Machine, naïve Bayesian machine, and/or clustering technique])) based at least in part on the depth data obtained by the one or more sensors; quantifying, by the processor, one or more bodyprints (i.e., a classification quantity) based on the quantified plurality of features for the human detected within the sensor field; and positively identifying, by the processor, in real-time or near-real-time, the human detected within the sensor field from among a set of pre-registered human individuals based at least in part on the one or more bodyprints.

In certain embodiments, the method includes determining an activity in which the positively identified individual is engaged (e.g., walking, bending over, falling down, turning, running, walking behind an object) based at least in part on the one or more bodyprints.

In certain embodiments, positively identifying the human is performed exclusively on depth data.

In certain embodiments, the depth data comprises one or more depth maps (e.g., a time series of depth maps) obtained by one or more sensors (e.g., one or more in-room sensors).

In certain embodiments, the depth data does not comprise visual images (e.g., photographs) (e.g., that, if viewed or analyzed in isolation without prior registration, would provide a positive identification of the individual).

In certain embodiments, positively identifying the human is accomplished without the use of photographic still or video images, thereby protecting personal privacy of the individual.

In certain embodiments, the plurality of features comprises at least one static feature (e.g., height, leg length, shoulder-to-shoulder width, the weights and/or outputs of a machine learning and/or pattern recognition technique [e.g., a Convolutional Neural Network, Random Forest, Support Vector Machine, naïve Bayesian machine, and/or clustering technique]) and/or at least one dynamic feature (e.g., angle-of-gaze, walking speed, head silhouette width, the weights and/or outputs of a machine learning and/or pattern recognition technique [e.g., a Convolutional Neural Network, Random Forest, Support Vector Machine, naïve Bayesian machine, and/or clustering technique]).

In certain embodiments, the set of pre-registered human individuals comprises no greater than one-hundred, no greater than fifty, no greater than twenty-five, no greater than ten, no greater than six, no greater than five, no greater than four, no greater than three, no greater than two, or no greater than one human individuals.

In certain embodiments, the human is positively identified with at least 80%, at least 90%, at least 95%, or at least 99% confidence.

In certain embodiments, the method includes displaying, by the processor, a name (e.g., nickname, first name, graphical icon, etc.) of the positively identified human detected within the sensor field and, optionally, displaying a graphical indication of the determined activity in which the positively identified individual is engaged (e.g., with at least 80%, at least 90%, at least 95%, or at least 99% confidence).

The disclosed technology, in certain embodiments, includes a method of identifying and/or quantifying at least one of pain, fatigue, mood, and intent of a person via physical measurements of the person, the method comprising: receiving, by a processor of a computing device, a data set (e.g., directly from one or more sensors or from storage) comprising sensor data acquired by a sensor (e.g., actively [e.g., the one or more sensors is engaged in acquiring data] and/or passively [e.g., the data are loaded from a file]); characterizing, by the processor, at least one member selected from the group consisting of movement, activity, and behavior of the person based on the data set, wherein said characterizing comprises: segmenting (e.g., distinguishing) one or more persons represented within the data set, from each other and from environmental objects represented within the data set (e.g., furniture), calculating at least one feature of at least one of the one or more segmented persons, and determining a conclusion based on correlating the at least one feature with a relationship; and outputting, by the processor, the conclusion.

In certain embodiments, segmenting the one or more persons represented within the data set comprises performing a machine learning and/or pattern recognition technique (e.g., a Convolutional Neural Network, Random Forest, Support Vector Machine, naïve Bayesian machine, and/or clustering technique) (e.g., either explicitly or implicitly).

In certain embodiments, the relationship is a learned relationship.

In certain embodiments, the at least one feature comprises physical measurements that are direct measurements (e.g., an immediate result of a sensor's interaction with the person's body).

In certain embodiments, the at least one feature comprises physical measurements that are indirect measurements (e.g., derived from other measurements, which may in turn be direct or indirect).

In certain embodiments, the conclusion is based on incomplete measurements (e.g., non-contiguous, non-adjacent, inconsistent, non-sequential measurements).

In certain embodiments, the at least one feature is based on measurements in the data set that are at least one of non-contiguous, non-adjacent, incomplete, inconsistent, non-sequential.

In certain embodiments, the conclusion is based on the consolidation of several different types and combinations of features.

In certain embodiments, the sensor data in the data set are acquired directly from a sensor (e.g., are raw data) and/or have undergone additional processing.

In certain embodiments, the data set comprises one or more frames.

In certain embodiments, each frame of the one or more frames corresponds to a snapshot of one or more data streams, comprising data acquired either preceding, or at, a particular moment in time.

In certain embodiments, the one or more frames are captured by a single sensor at multiple points in time and/or captured by multiple sensors.

In certain embodiments, the data set is acquired in substantially real-time (e.g., from a "live" data-feed), is acquired in batched mode (e.g., store-and-serve), or is acquired from data previously stored in a database.

In certain embodiments, the method includes discarding types of data determined to be non-private (e.g., that endanger the privacy of persons in an application of interest) (e.g., color image data, such as photographs).

In certain embodiments, the method includes pre-processing, by the processor, the data set for subsequent analysis, wherein pre-processing comprises one or more steps selected from the group consisting of filtering (e.g., denoising, averaging, and/or removing or repairing pieces of data that do not fit some quality criteria, such as consistent amounts of time between sequential data points), conditioning, cleaning, and normalizing the data set.

In certain embodiments, the method includes pre-processing, by the processor, the data set for subsequent analysis, wherein pre-processing is performed on raw data from the data set or calculated features.

In certain embodiments, segmenting is performed without any information as to the identity of the segmented person.

In certain embodiments, the method includes, after segmenting, determining a label for each of the one or more persons segmented in order to associate calculated features with a specific individual.

In certain embodiments, the at least one feature comprises at least one member selected from the group consisting of: limb length, foot size, head shape, height, body proportion, body volume, voice frequency spectrum, voice volume, stride length, location within a field-of-view, and speed of arm raise.

In certain embodiments, the method includes automatically calculating, by the processor, the at least one feature using a machine learning and/or pattern recognition technique (e.g., a Convolutional Neural Network, Random Forest, Support Vector Machine, naïve Bayesian machine, and/or clustering technique).

In certain embodiments, calculating at least one feature is suspended based on at least one of the availability of the specific features and relevance for the output conclusion.

In certain embodiments, determining, by the processor, the desired characteristic of movement, activity, or behavior based on the data set comprises, before segmenting, pre-processing, by the processor, the data set for subsequent analysis.

In certain embodiments, the relationship is pre-determined.

In certain embodiments, the learned relationship is based on a ground truth.

The disclosed technology, in certain embodiments, includes a system for identifying and/or quantifying at least one of pain, fatigue, mood, and intent of a person via physical measurements of the person, the system comprising: a sensor for acquiring data corresponding to the person; a processor; and a memory having instructions stored thereon, wherein the instructions, when executed by the processor, cause the processor to: receive a data set (e.g., directly from one or more sensors or from storage) comprising sensor data acquired by a sensor (e.g., actively (e.g., the one or more sensors is engaged in acquiring data) and/or passively (e.g., the data are loaded from a file)); characterize at least one of movement, activity, and behavior of the person based on the data set, by: segmenting (e.g., distinguishing) one or more persons represented within the data set, from each other and from environmental objects represented within the data set (e.g., furniture), calculating at least one feature of at least one of the one or more segmented persons, and determining a conclusion of the person based on correlating the at least one feature with a relationship; and output the conclusion.

In certain embodiments, segmenting the one or more persons represented within the data set comprises performing a machine learning and/or pattern recognition technique (e.g., a Convolutional Neural Network, Random Forest, Support Vector Machine, naïve Bayesian machine, and/or clustering technique) (e.g., either explicitly or implicitly).

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 5A through 5E illustrate examples of features and/or bodyprints, according to illustrative embodiments;

FIG. 10 lists examples of relationships between measured features and determined conclusions;

Figure 1A:
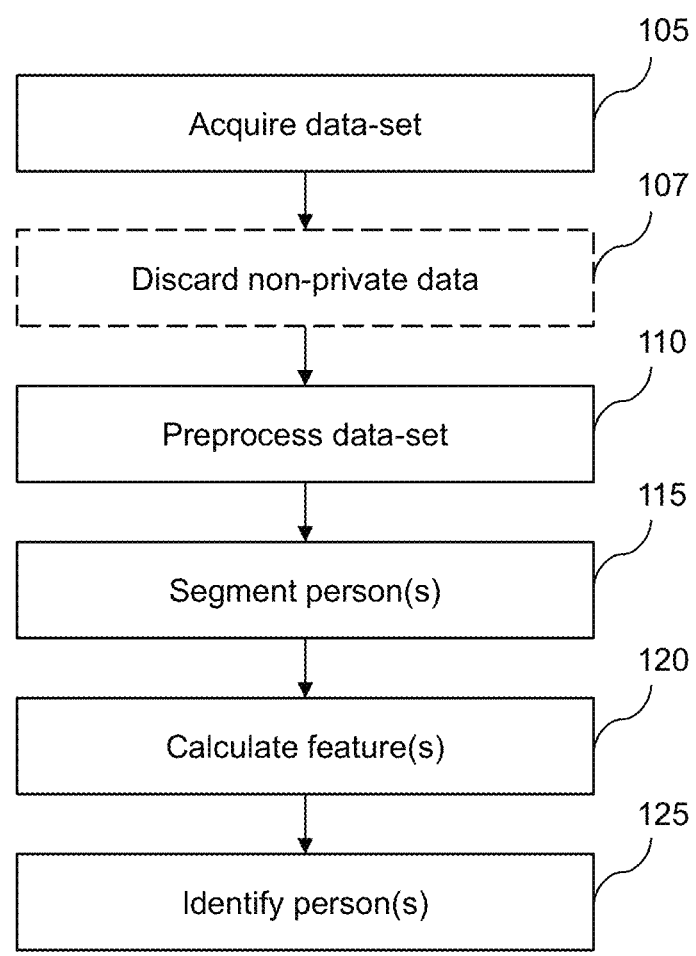
FIGS. 1A through 1D are high-level block diagrams illustrating methods of identifying a person and/or identifying and quantifying pain, fatigue, mood, or intent, in accordance with some embodiments of the present invention.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

In this application, unless otherwise clear from context, (i) the term "a" may be understood to mean "at least one"; (ii)

the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art.

Activity: As used herein, "activity" indicates coordination of movement in the context of an environment. Examples of "activity" include using a cane to ambulate, using a phone to hold a conversation, and sitting for some determinate period of time.

Attribute: As used herein, "attribute" refers to the real-world value of some property of a person or an object. An attribute is the "ground truth" or "reality" of something in the real world. Examples of physical attributes include the (real) volume of a person's head, the (real) circumference of a person's upper arm, and the (real) color of a person's hair (as wavelengths of visual light). Examples of mental or intentional attributes include the (real) level of a person's fatigue or pain, the (real) intent of a person as to whether or not to carry out a contemplated action, and the (real) degree of alarm felt by a subject in relation to a sensed danger.

Behavior: As used herein, "behavior" indicates progress, via movement and/or activity, toward a goal. Examples of "behavior" include eating a meal, looking up in surprise at a loud sound, sleeping at a desk during work hours, and gesticulating in anger. The terms "activity" and "behavior" overlap and will occasionally be used interchangeably herein.

Bodyprint: As used herein, a "bodyprint" is 1) a set of features, combined with 2) a range of measures for each of those features, which together are highly specific to a particular person (within the set of persons whose "bodyprints" are known to the system), and for which the degree of specificity may optionally be quantified by a 3) so-called "bodyprint-score". A "bodyprint" is the present inventive system's analogue to a person's "fingerprint".

Camera: As used herein, "camera" refers to any sensor that may gather information about the environment, especially (though not limited to) electromagnetic measurements, such as visible or infrared light. "Camera", as used herein, is thus a general-purpose term referring to a type of sensor, and does not refer specifically to, nor is limited to, visual-light devices.

Conclusion: As used herein, "conclusion" refers to an appraisal of a person's pain, fatigue, mood, and/or intent and/or a characterization of a person's movement, behavior, and/or activity. A conclusion may be determined based on correlating "features" of the person (and/or the person's environment) with a "relationship" (either pre-determined or learned). For example, a conclusion might be, "Bob is in greater pain than last week." For example, a conclusion might be, "Bob is in 20% greater pain than last week." For example, a conclusion might be, "An unknown person in the field-of-view is leaving behind a suspicious object."

A conclusion may additionally comprise quantified calculations related to a person's movement, activity, or behavior. For example, in determining that a person's intent includes walking briskly, the conclusion output may state the calculated walking speed of the person. As an additional example, in determining a person's mood, the conclusion output may state a qualitative mood as well as the person's stride length and/or duration and frequency of eating in order for a monitor to further characterize the person's mood.

Data set: As used herein, "data set" refers to a collection of one or more frames. The one or more frames may have been obtained at substantially different times. Types of data within a data set may include but are not limited to: raw sensor data (e.g., color image data from a digital camera), calculated sensor data streams (e.g., skeleton data calculated from depth data), or a wide variety of calculated data types such as body silhouette, walking speed, stride length, joint orientations, and/or other such metrics which may have spatiotemporal dependencies, as described further herein. A data set may be collected via a single sensor or via multiple sensors which may be placed at varying observation points and which may or may not be synchronized in time.

Data stream: As used herein, "data stream" refers to a sequence of digitally encoded signals originating from a sensor. Examples of data streams include: one-dimensional data streams (e.g., the signal from an infrared beam that is "broken" when someone crosses it); two-dimensional data streams (e.g., webcam photos or videos); and three-dimensional data streams (e.g., depth images, in which each pixel of the image corresponds to the real-world distance from the sensor to some portion of an object in the field-of-view).

Depth data: As used herein, "depth data" refers to information about the spatial positions of objects in space relative to a known coordinate system. In some embodiments, depth data are acquired using time-of-flight light detection and ranging (LIDAR). In other embodiments, depth data are acquired by projecting a pattern onto the scene and measuring its deformation. In other embodiments, depth data are acquired by a variety of methods including light (electromagnetic radiation), sound (acoustic), or additional modalities. Depth data may be represented in a manner similar to 2D image data, wherein the intensity value of each pixel in the 2D so-called "depth map" contains a measurement of distance from a common reference plane—e.g., a vertical plane established by the sensor itself—to a point or plane in space corresponding to a given object. There are many ways to acquire, calculate, or otherwise generate depth data for a field-of-view, as described in U.S. Pat. No. 9,341,464, entitled "Method and Apparatus for Sizing and Fitting an Individual for Apparel, Accessories, or Prosthetics" and filed Oct. 2, 2012, which is hereby incorporated by reference in its entirety.

Dynamic feature: As used herein, "dynamic feature" refers to a feature that varies with time over a time period of interest (e.g., over seconds, minutes, or hours). Dynamic features are measured using time-varying data. A dynamic feature may be determined or measured from a single frame, or from multiple frames which may or may not be contiguous in time or space. As with static measures, the measured value (or measure) of a dynamic feature may differ from its actual real-world value because of measurement limitations. Examples of dynamic features include: location of an object in a room, orientation of a person's body relative to a sensor, ambient temperature, instantaneous walking speed, average walking speed (calculated over an arbitrary duration of time), and stride length.

Feature: The term "feature", as used herein, refers to a representative characteristic or metric that can be used to identify a person and/or to measure something about a person.

In some instances, the term "feature", as used herein, may refer to a calculation or other determination of a real-world attribute or of a combination of real-world attributes. Each such feature may be calculated directly from raw data; from calculations on raw data; and/or from calculations on other features, in any weighting or combination. (In real life, measurements acquired of objects are necessarily an approximation of the "ground truth" attributes, because of noise, errors, and other sources of degradation. For example, the measured volume of a person's head may be erroneous due to occluding headwear or resolution limits of the sensor. For example, the measured color of a person's hair may vary due to impinging ambient light.)

In some instances, the term "feature", as used herein, may refer to any measureable property of the person(s), of the surrounding environment, of the sensor data (raw or processed), and/or of other features. Each such feature may optionally be calculated over time, over space, over some other measurement unit (such as angle, or pixel-count), or over any combination thereof. For example, a feature may be a quantity or property of a person that is physically measurable (e.g., height of a person in meters). For example, a feature may be a quantity or property of a person that is derived in turn from other properties or features (e.g., a mathematical eigenimage of a face, also known as an eigenface; or the count of pixels that comprise the head in a set of pixel-label data, which term is defined below). Additional examples of features (not exhaustive) include: shoulder-to-shoulder width, head size, head morphology (shape), nose morphology, eye-to-eye distance, eye-to-ear distance, walking speed (instantaneous or average), stride length, SIFT (scale-invariant feature transform) of a body portion, and HOG (histogram of oriented gradients) of a body portion.

Some features may be readily comprehensible to humans, corresponding to intuitively apprehensible human-scale attributes, such as a person's height. Other features may be less intuitive to humans, corresponding to purely mathematical representations, such as the numerical output of an abstract algorithm. Other features may be combinations thereof. Features may change over time, for example, with varying input data or with varying calculation methods. For example, a calculated eigenface—which is a mathematical construct based on the principal components of the image of a face—may, to a human's vision, not resemble a known face, or any face. For example, a Convolutional Neural Network (CNN) may calculate features corresponding to mathematical operations that are independent of an intuitive human interpretation.

Some aspects of feature determination may be undertaken a priori (i.e., in advance of the series of steps described in FIGS. 1A through 1D). For example, the general outline and structure of a machine learning construct, such as a CNN, may be determined a priori. Other aspects of feature determination may be undertaken a posteriori (i.e., during or after the series of steps described in FIGS. 1A through 1D). For example, the specific weights and distributions of calculations within a machine learning construct, such as a CNN, may be determined a posteriori.

Frame: As used herein, "frame" refers to a collection of data acquired at or near, or corresponding to, a particular moment in time. For example, the data may be depth data describing the distances to objects in the field-of-view; or the data may be skeleton data identifying the locations of a human's joints (such as heads or hands) in 3D space; or the data may be pixel-label data which labels pixels corresponding to the body surfaces of humans in the field-of-view. Other data types are also possible. Detailed descriptions of representative data types are provided in International Application No. PCT/US2012/058534, entitled "Method and Apparatus for Detecting Deterioration of Health Status" and filed Oct. 3, 2012, and International Application No. PCT/US2012/060041, entitled "Method and Apparatus for Monitoring Individuals While Protecting Their Privacy" and filed Oct. 12, 2012, each of which is hereby incorporated by reference in its entirety.

Each frame may contain one, or more than one, data type and contain data from one, or more than one, data stream. To help protect the privacy of a person to be identified, any or all of the data types acquired within a frame may not require visible light. Each frame of data may be associated with a timestamp to identify the time that the data was acquired, so as to enable precise calculations of rates of change and to combine data acquired across multiple sensors. (If multiple sensors are in use simultaneously, it may be necessary to synchronize the timestamp mechanisms to ensure that frames are reported in the correct time order.)

Identify/ing person(s): As used herein, "identify person(s)" or "identifying person(s)" refers to distinguishing one specific person-of-interest out of a larger group of persons: for example, identifying that one person in a room is "Bob". Identification may be positive or negative. "Positive" identification means ruling in a person: for example, "this person is Bob". "Negative" identification means ruling out a person: for example, "this person is someone other than Bob". Identification may be probabilistic: for example, "this person is probably Bob", or "this person is probably someone other than Bob".

Identity: As used herein, "identity" refers to one of a set of pre-determined labels (or categories) into which a person may be classified (or categorized). A label placed upon a person can map to that person's identity in real life. Examples of identities include "Bob," "Patient Number 10," and "other" (equivalent to "a person who is unknown to this system").

Image data: As used herein, "image data" refers to information about the image of a scene, which may be in, for example, visual wavelengths or in other wavelengths of the electromagnetic spectrum. As used herein, "color image data" refers to gathering a visual image of a scene, using color wavelengths, similar to the way in which a standard digital camera gathers a visual image.

Intent: As used herein, "intent" indicates the underlying goal or motivation of a person. Examples of "intent" include intent to take a medication, intent to wear safety gear, intent to check out a warning sight or smell, intent to steal an object from a store, intent to do harm to someone, intent to sneak something into a restricted area, and intent to scout a location then leave behind a harmful device.

Learned relationship: As used herein, a "learned relationship" is a relationship that is determined during data analysis. In certain embodiments, a relationship is learned through methods of machine learning. For example, the relationship of measured features such as "the person's average arm height was lower than usual by ten percent during three of the past five weeks" and "the person indicated on a survey that the person felt more depressed than usual during those same three weeks" to the conclusion "with high confidence, a decrease of average arm height by ten percent indicates a worsening of depressive mood" is learned. A learned relationship may be abstract or mathematical, regardless of comprehensibility to a human; for example, the numerical weights of a CNN may comprise a learned relationship. There is overlap between learned and pre-determined relationships: in particular, a learned relationship, once established, may subsequently be employed as a pre-determined relationship.

Machine-readable medium, computer-readable medium: As used herein, the terms "machine-readable medium" or "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Movement, motion: As used herein, "movement" or "motion" indicates a change in the physical positioning of a body or part of a body. Examples of movement include the act of walking, raising an arm, bending, sitting, and standing. Measures of movement include walking speed, stride length, and speed of raising an arm. Movement or measures of movement can be used as proxies for mental perception or intent. The terms "movement" and "motion" are used interchangeably.

Person: As generally used herein, "person" refers to the representation of a human being in a data set. In some instances, a representation of a person is specifically referenced for clarity to refer to a specific human being.

Person identification with privacy: As used herein, "person identification with privacy" refers to identifying a person while revealing minimal information about that person other than the identification. In some embodiments, protection of privacy may not be needed, in which case embodiments of the present invention may also be used for the general identification of persons (without regard to privacy).

Pixel-label data: As used herein, "pixel-label data" consists of labeling components of a collection of data, such that each labeled component corresponds to a point of interest (e.g., a point that is located on the surface of a human body). For example, in a depth map, the pixels which correspond to the body shape of "Person A" may be labeled "A". For example, pixel-label data may be determined from, or for, separately-acquired depth and/or image data. There are many ways to acquire, calculate, or otherwise generate pixel-label data for a field-of-view, as described in U.S. Pat. No. 9,341,464, which is hereby incorporated by reference in its entirety.

Portion of the body, body portion: As used herein, "portion of the body" or "body portion" refers to all of a person, or a section of a person, or a spatial location in or on a person. Any person may be broken down into portions. For example, a portion of a person may correspond to a body shape, or to a body section—such as a head, shoulder, arm, or leg—or to a smaller anatomic part of the body, such as a joint, skin surface, or skin curve.

Pre-determined relationship: As used herein, a "pre-determined relationship" is a relationship that is defined in advance of data analysis. For example, the relationship of measured features "the person's hand moved from chest height to mouth height ten times within the past sixty seconds" to the conclusion "the person is now eating" is pre-determined. For example, the relationship of measured features "the person's posture declined ten percent this week compared to last week" to the conclusion "the person is more fatigued this week than last week" is pre-determined.

Protecting personal privacy: As used herein, "protecting personal privacy" refers to preventing the acquisition and/or dissemination of embarrassing, undignified, or even merely idiomatic information about a person, e.g., photographs of that person or of what that person is reading or viewing. Protecting personal privacy may refer to preventing the acquisition and/or dissemination of information which a person does not wish to reveal to a monitor (e.g., to an entity familiar or unfamiliar with the person, which may be charged with observing the person, or which may wish to observe the person for other reasons).

Relationship: As used herein, "relationship" refers to an association between one or more features and/or their measures over time and a movement, activity, or behavior. Further, each movement, activity, and behavior (or combination thereof) can act as a proxy for pain, fatigue, mood, or intent. Thus, a conclusion regarding a person's mental perception or intention can be determined by correlating the one or more features to a relationship. A relationship may be pre-determined or learned.

Scene: As used herein, "scene" refers to the physical scene comprising (potentially) some persons interspersed with objects, such as furniture, that are within the field-of-view (FOV) of a sensor.

Segmentation: As used herein, "segmentation" (e.g., segmentation of sensor data) refers to distinguishing a person from other people, objects, or the environment (e.g., segmenting sensor data into a representation of the person). In certain embodiments, segmentation is undertaken to decide that a collection of pixels in a depth map (or any other representation of data) corresponds to a single person and not to, say, a piece of furniture, or to two (or more) different persons. In certain embodiments, "segmentation" refers to applying a machine learning and/or pattern recognition technique (e.g., a Convolutional Neural Network, Random Forest, Support Vector Machine, naïve Bayesian machine, and/or clustering technique) to distinguish a person, e.g., in sensor data. For example, segmentation may explicitly generate a boundary or outline representation corresponding to the person; or segmentation may implicitly identify a region or subset of data corresponding to the person, without explicitly producing a boundary or outline; or segmentation may implicitly conclude that one or more features obtained from one or more data frames are sufficient to decide that the person is present in those data frames, without identifying or marking any specific data within those data frames as corresponding to the person.

Sensor: As used herein, "sensor" refers to the device used to record measurements of the scene. Examples of sensors include, but are not limited to time-of-flight (ToF) sensors, cameras, bolometers, acoustic transducers, LIDAR, and any other sensor modality used to capture static or dynamic data streams of persons or of the environment. The sensor can be, for example, a one-dimensional, two-dimensional, or three-dimensional sensor. Examples of one-dimensional data include: microphones, thermometers, light sensors, and distance sensors. Examples of two-dimensional data include: photographs, videos, infrared imagery, thermal imagery, and others. Examples of three-dimensional data include: depth maps and point clouds.

Sensor-based data: As used herein, "sensor-based data" refers to data that are acquired from any sensor to measure any aspect of a person or of the surrounding environment. Examples of sensor-based data include images (visual, infrared), temperatures (bolometer), and acoustics (ultrasound). The sensor-based data are used to generate "features"—i.e., measurements—of the scene being observed. As described herein, features may be static or dynamic. A static feature changes only slowly, or never, over some time period of interest (e.g., days-to-weeks: an example is a person's height). A dynamic feature changes appreciably over some time period of interest (e.g., minutes-to-hours: an example is a person's walking speed).

Skeleton data: As used herein, "skeleton data" describes data consisting of the approximate locations in space of joints, or of other ambiguous and/or diffuse anatomic structures. For example, skeleton data may be determined from, or for, separately-acquired depth and/or image data. There are many ways to acquire, calculate, or otherwise generate skeleton data for a field-of-view, as described in U.S. Pat. No. 9,341,464, which is hereby incorporated by reference in its entirety.

Snapshot: As used herein, "snapshot" refers to a single frame of one or more data streams acquired either preceding, or at, a particular moment in time.

Static feature: As used herein, "static feature" refers to a feature that varies with time only slowly, or not at all, over a time period of interest (e.g., over seconds, minutes, or hours). In engineering parlance, an adjective synonymous with the preceding definition is "quasistatic". Which level of variance shall be deemed as "slow" is arbitrary and application-dependent and may be defined in absolute terms (e.g., as a fixed number) or in relative terms (e.g., as a standard deviation, or as a ratio of a measurement to an average of repeated measurements). A static feature may be determined or measured from a single frame (contemporaneous set) of data, or from multiple frames which may or may not be contiguous in time or space. As described above, the measured value (or measure) of a static feature may differ from its actual real-world value due to, for example, fluctuations or noise in the sensor measurements, or limitations in the field-of-view (FOV) of the sensor. Multiple frames may be aggregated to improve the measured precision or signal-to-noise of a static feature. Examples of static features include: height, shoulder-to-shoulder width, and head volume.

DETAILED DESCRIPTION OF THE INVENTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, and/or the description of any concepts in the Background section, is not an admission that the publication or concept serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

To identify a person—while protecting that same person's privacy—may at first glance seem a misnomer or a paradox. However, in some embodiments, a goal of the present invention is to identify a person without exposing private information such as the person's visual appearance, state of dress, what he/she is reading or watching on TV, etc. Furthermore, in certain embodiments, the goal is not to identify everyone in the universe—but rather, only a small set of people such as the people in a household. The disclosed technology enables the identification of these individuals even when they are moving around and distant from the sensor, and even when multiple individuals are present at the same time.

The disclosed technology enables, among other things, the ability to identify and track persons for medical, safety, and/or home care purposes. Of particular significance are applications that require long-term patient monitoring, such as tracking the progression of degenerative diseases (e.g., multiple sclerosis), or monitoring the efficacy of treatment or rehabilitation. Such purposes require that the identity of a person be determined so that longitudinal data can be attached to that person (e.g., a patient) over time.

Research settings, such as a laboratory, are controlled—in other words, someone such as a clinician or a scientist can dictate the precise placement of furniture and devices, the exact activities of people (including operators and research subjects), and so forth. In contrast, real-world settings, such as a person's home, are uncontrolled—in other words, an outside party has little or no control over device placement, human activity, and so forth. This means that a person-identification solution destined for use in the real world must be robust to identifying persons even in uncontrolled environments, where events may occur and objects may change without advance notice, while satisfying the requirement that the person-identification solution can autonomously adapt.

Examples of changes pertaining to a person include: choice of clothing worn today; weight gain or loss; recent haircut; wearing glasses or not; posture and gaze; spoken and physical interactions with other persons. Examples of changes pertaining to a local environment include: sensor location or relocation; lights on or off; new furniture; house construction. The disclosed technology is designed to handle a wide variety of environments, both controlled (e.g., laboratory) and uncontrolled (e.g., real world), including (for example) accommodation of the changes just described.

The disclosed technology accomplishes these goals, in certain embodiments, while improving accuracy, rather than diminishing accuracy, as the person to be identified moves around in various ways. In certain embodiments, the disclosed technology may reduce the margin of error in person identification by obviating dependency upon a single feature or attribute. For example, facial recognition typically requires an up-close image of the full face, and therefore fails when the subject is not facing the camera. For example, gait recognition typically requires an unobstructed view of a specific walking path, and therefore fails when the subject is stationary or off the path.

Some present-day person-identification solutions combine multiple methods of solo identification (such as face, voice, and handprint) in an attempt to improve cumulative accuracy. In contrast, the disclosed technology, in certain embodiments, employs features that may not (each on their own) act as means of solo identification, yet when combined, provide even higher accuracy and more-robust operation in uncontrolled environments. In this way, the disclosed technology, in certain embodiments, also provides relative robustness to deficiencies in data acquisition from any one sensor type or from any one sensor placement, thus providing a larger range of operating conditions over any single sensor modality.

Moreover, solutions for medical applications must address privacy concerns. For example, persons may be opposed to the placement of video cameras or similar devices into their homes that could show their state of dress or undress, what they are reading, etc. The disclosed technology, in certain embodiments, may avoid the use of photography—thus maintaining user privacy and robustness to sensor artefacts (e.g., robustness to changes in accuracy at different distances from the sensor) and reducing or eliminating the need to place multiple sensors or sensors of different modalities, at various locations, including locations that are sensitive to privacy.

The systems and methods described herein relate to identifying one or more persons based on data gathered from one or more sensors and/or characterizing movement, activity, and behavior using direct and/or indirect measurements from data acquired by one or more sensors, in order to detect and/or quantify pain, fatigue, mood, and intent.

The data from the sensors may be incomplete, or may be noisy, or may be heterogeneous in type and precision, or may vary over time. The data from each sensor in any particular moment in time, or at any particular location in space, may in and of themselves be insufficient to perform a correct identification of each person and/or may in and of themselves be insufficient to characterize movement, activity, or behavior of an individual.

In some embodiments, methods and systems of the present invention aggregate disparate and fragmented data from the sensor(s), over space and/or time, then employ the combined data to calculate one or more static and/or dynamic features of each person so as to perform correct identification of each person. Of note, the features used for person identification may be different from person to person even within the same scene, depending on what features are actually available (which in turn depend on occlusion of the person by environmental objects, the orientation of the person relative to the sensor, etc.), as described further herein.

In some embodiments, the disclosed technology provides the ability to infer or otherwise characterize a movement or behavior from a single, combination of several, or combination of several different groups of opportunistically gathered measurements. The combination or sets of combinations of these measurements may be consolidated to achieve confidence in the characterization of the movement, activity, or behavior in question.

In contrast to many present-day methods, the systems and methods described herein do not require that a single measurement, or any fixed combination of measurements, be used to infer the movement, activity, or behavior of interest. Instead, the consolidation of several different types and combinations of measurements, opportunistically gathered, can be used to infer the movement, activity, or behavior of interest. This facility is important to accommodate noisy, real-world, or other uncontrolled settings.

Examples (not exhaustive) of measuring movement, activity, or behavior follow. For example, to measure the stride length of a person when the legs are occluded from view, the system may calculate stride length indirectly via measurements of the start-and-stop position of the head over time (i.e., the bob of the head with movement). For example, to detect eating activity when the mouth is too distant for shape recognition, the system may rely upon detection of repeated movement of a hand from chest height to chin height (hand oscillation). For example, to detect stand-to-sit movement when the waist is obscured by clothing, the system may rely indirectly upon measurement of head height.

Examples (not exhaustive) of detecting and/or measuring pain, fatigue, mood, or intent follow. For example, to quantify a person's level of fatigue, the system may measure the number of steps taken over a fixed period of time; or the slump of the shoulders; or the downward angle of the chin; or the amount of time spent sitting; or the amount of time taken to rise from a sitting position; or a change in walking speed; or posture; or spine angle from vertical; or a combination of some or all of these features. For example, to detect a person's intent to sneak into a restricted area, the system may measure components of the person's gait; or walking trajectory; or direction of gaze; or posture; or aspects of facial features; or a combination of some or all of these features. For example, to quantify a change in hip pain, the system may measure time spent walking; or time spent using a cane, or walking speed; or a combination of some or all of these features. For example, to quantify a change in mood, the system may measure hand velocity; or arm height; or posture; or tilt of head; or velocity of overall movement; or aspects of facial features; or Fourier analysis of verbal utterances; or a combination of some or all of these features. For example, to detect a person's intent to walk to a particular place, the system may measure changes in the angle of both upper and lower body to face a destination, even before there are changes in walking speed or initiation of walking from a stationary state. For example, to measure a person's intent to leave, say, a backpack at a location, the system may measure starting to unbundle the backpack from the body while standing in the location. In each of these examples, a mental perception or intention is detected and/or quantified via physical measurements of the body.

By opportunistically drawing upon a variety of data streams and measurements, whether real-time or stored, the disclosed technology provides for measurements of motion when direct observation or measurement of a particular quantity of interest is not available (by inferring the particular quantity of interest from proxies or derived values). An inference may be calculated based upon whatever features are available from time-to-time, and the available features may vary from frame-to-frame of data. The validity of a measurement may be adjudicated by combining opportunistically gathered pieces of data until a confidence threshold is met.

In certain embodiments, the components of a measurement are specified: for example, which features, how many features, and what minimum or maximum time-period of data acquisition. The disclosed technology can be used for retroactive calculation of a quantity of interest, so long as the needed data have been acquired. Features need not be contiguous or sequentially gathered. Fragmented and/or inferred knowledge of a movement, activity, or behavior can be gathered opportunistically and consolidated until a desired confidence threshold is reached.

Data Acquisition and Preprocessing

FIG. 1A is a flowchart of an example of a method to identify a person, according to an illustrative embodiment. The approach of FIG. 1A begins with a data acquisition step 105. In this step, a data set is created or loaded from storage. The data set contains sensor data acquired from measurements of a scene either actively (e.g., the sensor is engaged in acquiring data) or passively (e.g., the data are loaded from a file). The data set may originate from one or more sensors. The data may be acquired directly from a sensor (e.g., raw data) and/or data which has undergone additional processing. The acquired data set may comprise one or more frames, wherein each frame corresponds to a "snapshot" of one or more data streams comprising data acquired at a particular moment in time. The one or more frames may be taken by a single sensor at multiple points in time, taken by multiple sensors, or any combination or merging thereof. The data set may be acquired in substantially real-time (e.g., through a "live" data-feed), may be acquired in batched mode (store-and-serve), or may be acquired from data previously stored in a database. Step 105 may encompass a wide variety of measurements, attributes, and features calculated from depth data or other types of input data (e.g., bolometry, acoustic, or radio frequency).

Step 107 optionally discards types of data, such as color image data (photographs), that might be considered non-private, i.e., that might endanger the privacy of persons in an application of interest.

Steps 110-120 process the data set to calculate features. Step 110 filters, conditions, cleans, and otherwise preprocesses the data for subsequent analysis. Step 110 may encompass a wide variety of processing and mathematical operations, performed on raw data and/or on calculated features, and may optionally generate newly-derived data streams via mathematical operations such as (for example) image resizing, key point detection, thresholding, segmentation, histogram of oriented gradients (HOG), edge detection, and eigenimage decomposition. Step 115 optionally segments (isolates) person(s) within the data set, if any, from each other; from inanimate objects such as furniture; and from the surrounding environment. Step 120 performs measurements on the as-yet-unidentified persons, thereby calculating features. Step 125 uses those features to identify one or more persons in the scene. The output of Step 125 may be a rule-in identification ("this person is probably Bob") or a rule-out identification ("this person is probably not Bob") or an unknown ("there's not enough information to tell whether this person is or is not Bob"). The output of Step 125 may include a measure of probability, such as a confidence score between 0 and 1.

Figure 1B:
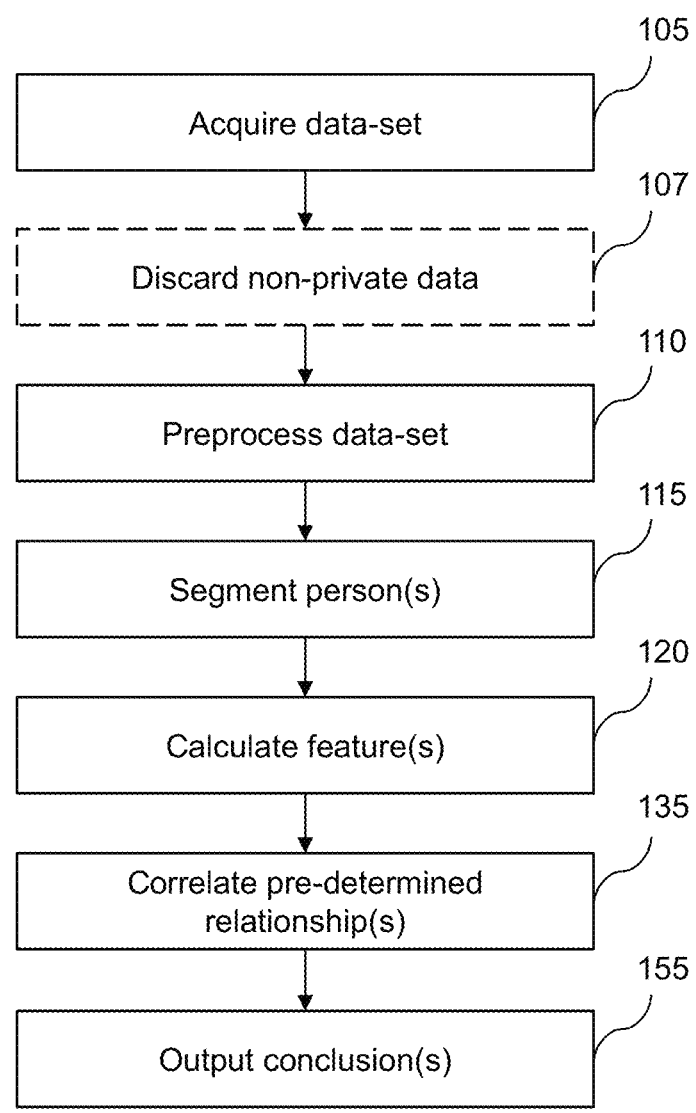
Figure 1C:
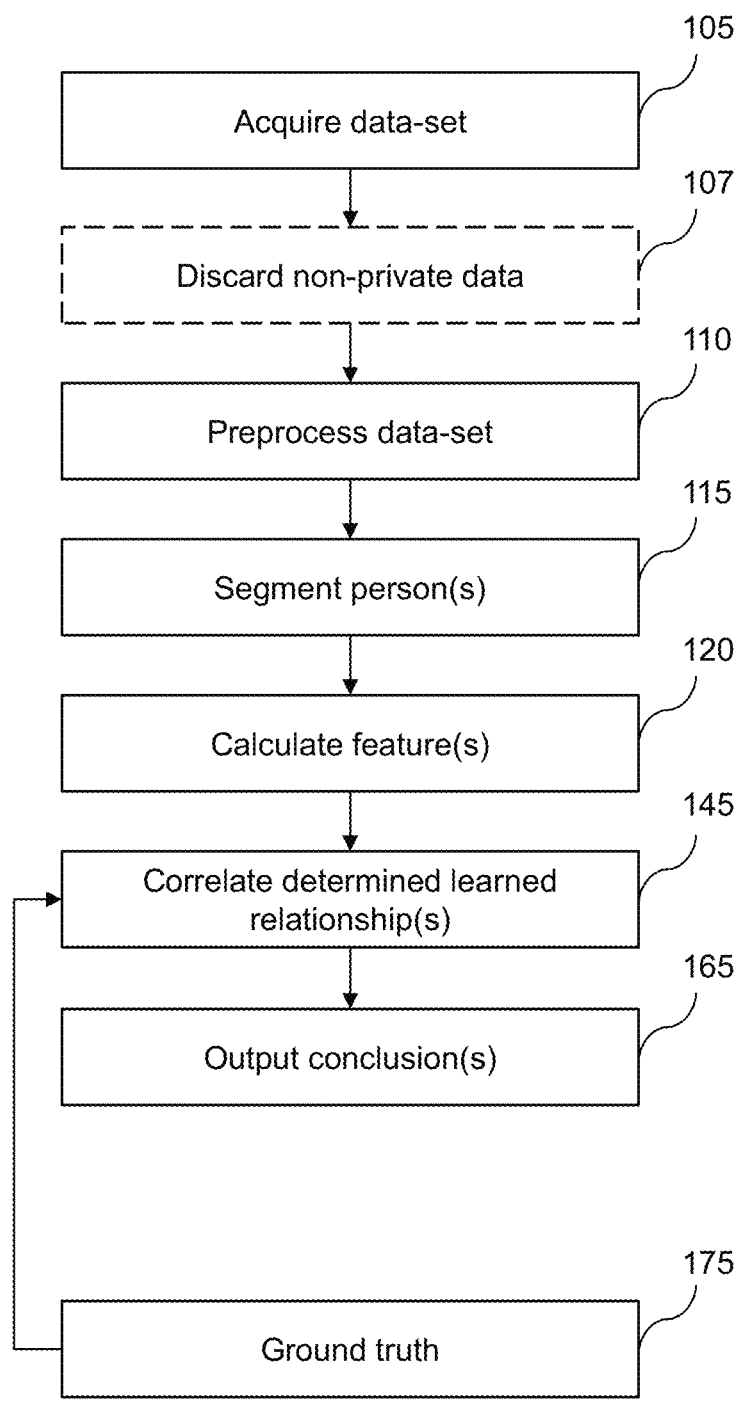

In some embodiments, as shown in FIGS. 1B and 1C, features calculated in Step 120 are used to output conclusions in Steps 155 and 165, respectively. In some embodiments, as shown in FIG. 1B, features are correlated with pre-determined relationships in Step 135 to output conclusions in Step 155. In some embodiments, as shown in FIG. 1C, features are correlated with learned relationships in Step 135 that are based on the ground truth 175 to output conclusions in Step 165.

Figure 1D:
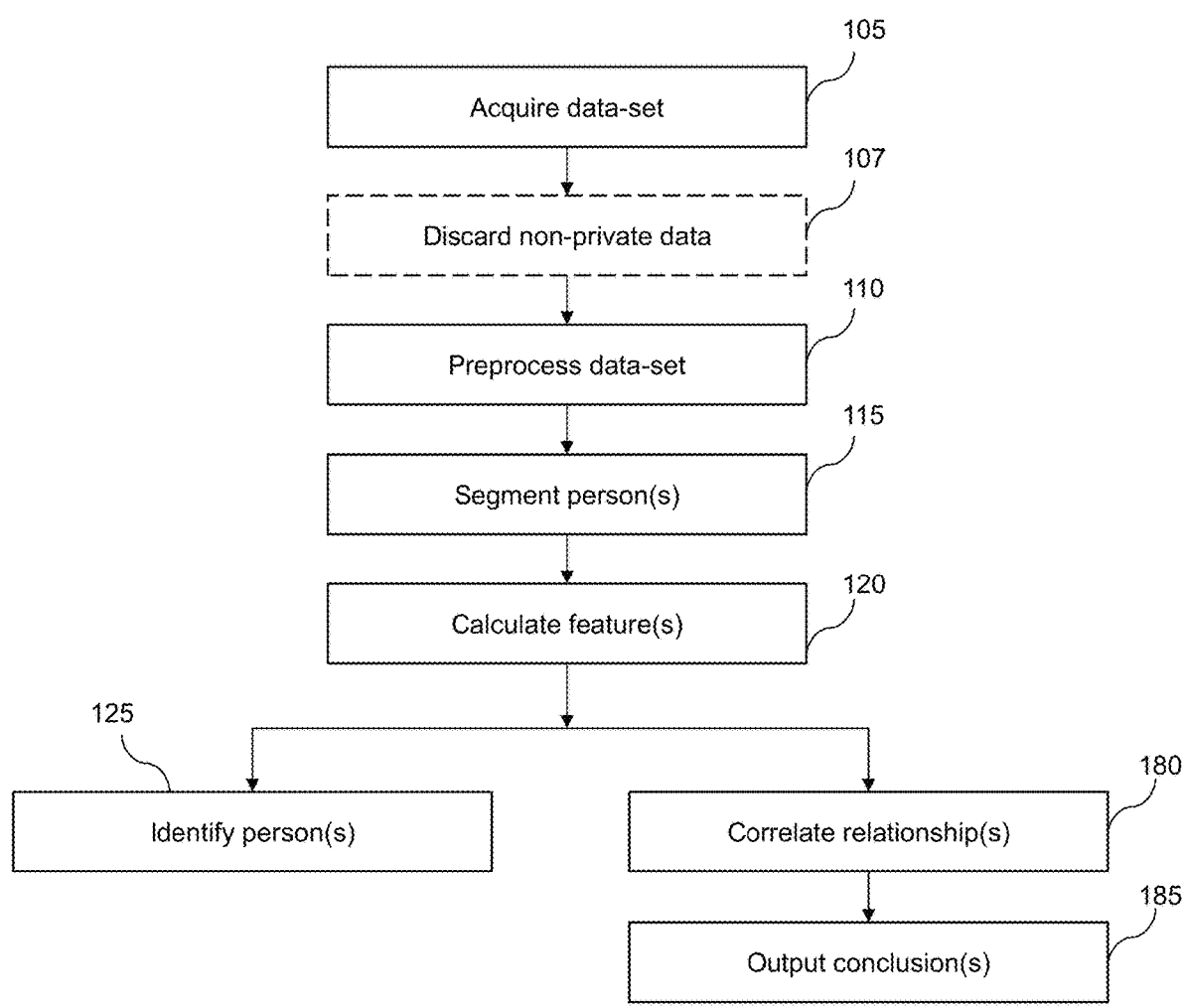

In some embodiments, as shown in FIG. 1D, features are used both to identify a person in Step 125 and to output conclusions in Step 180. In this example embodiment, calculated features from Step 120 are correlated with relationship(s), either pre-determined or learned, in Step 180 to output conclusions in Step 185.

Figure 2A:
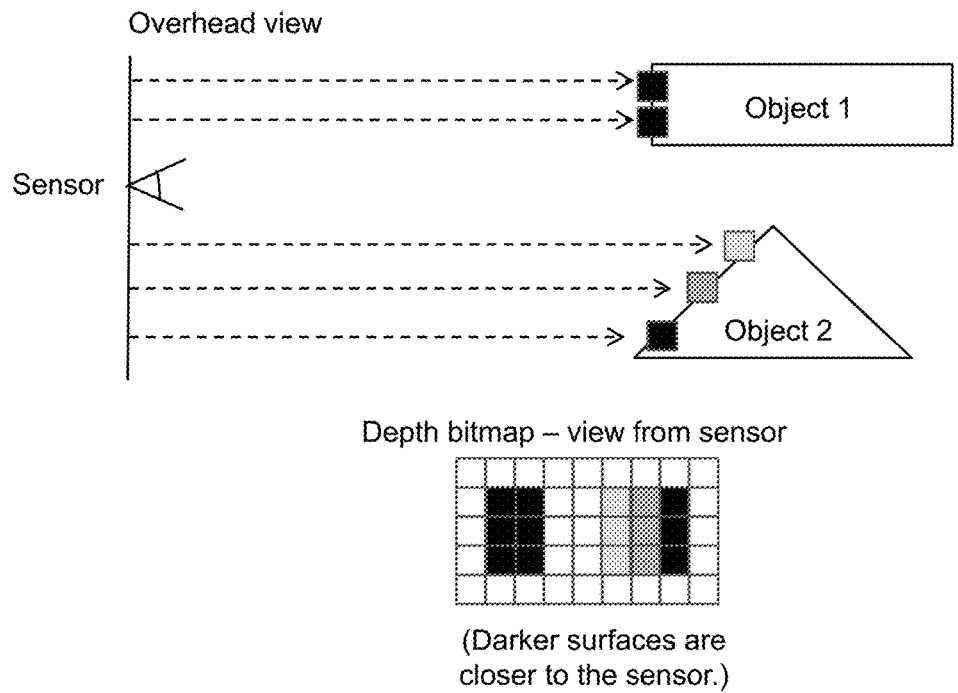
FIGS. 2A through 2C illustrate a schematic of an example sensor type based on infrared reflectance measurements and its use in measuring depth (spatial) data from a scene, according to illustrative embodiments.
Figure 2B:
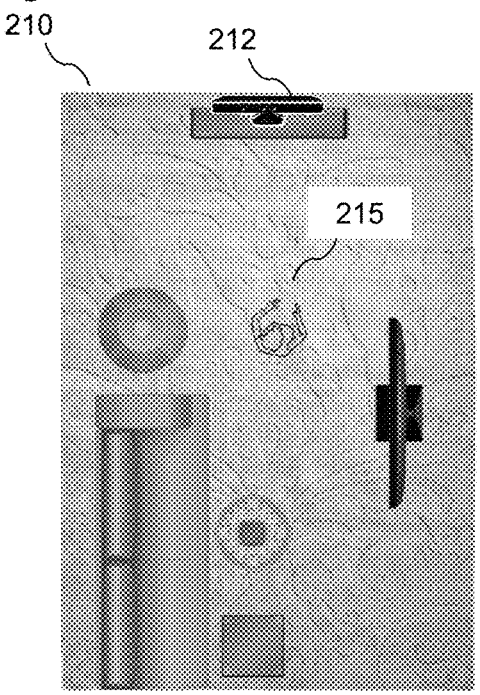
Figure 2C:
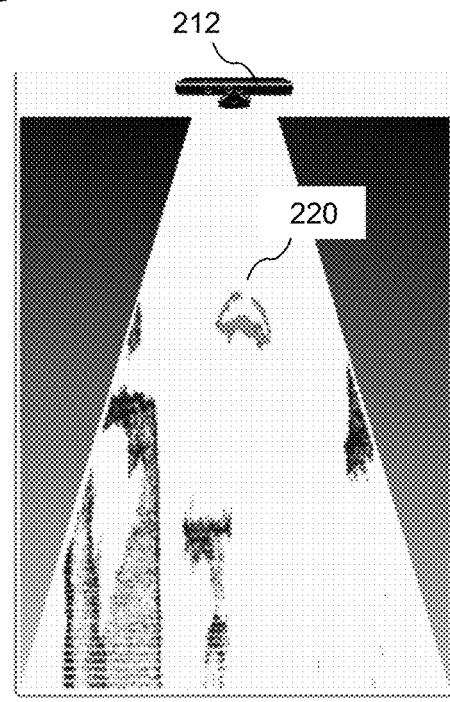

FIGS. 2A through 2C illustrate an example approach and sensor for measuring a scene and producing a representative data set.

In some embodiments, as shown in FIG. 2A, the frames contain at least depth data, wherein the depth data are represented as two-dimensional "depth maps" of pixels (i.e., matrices), with the two dimensions of each depth map corresponding to real-world spatial axes originating at the sensor and with the intensity value of each pixel corresponding to a projected distance from the sensor (that is, the horizontal distance between a first vertical plane passing through the sensor and a second vertical plane passing through an object in the scene). Multiple frames, with each frame corresponding to a measurement of the scene taken at a specific time, may be sequenced to form an evolution of depth data over time, similarly to the way photographic visual-light images are sequenced to form a video.

In some embodiments, as shown in FIG. 2B, a sensor is placed in a room—for example, the living room 210 in a person's home through which a person 215 is traversing—to acquire depth data of the person whenever the person happens to be near the sensor 212. As shown in FIG. 2C, the depth data obtained by the sensor 212 may be further processed to segment (isolate) a person 220 from other objects, such as furniture or pets.

Figure 3B:
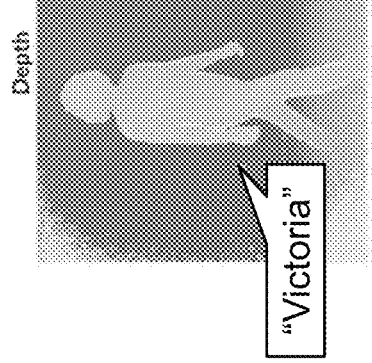
FIGS. 3A through 3M illustrate snapshots of a part of an example system demonstrating example raw sensor data streams (color, depth, and skeleton data); a derived feature (walking speed); the identification of representations of persons and a person-of-interest ("Tim") under a variety of conditions (e.g., orientations, postures, and occlusions of the persons), according to illustrative embodiments.
Figure 3A:
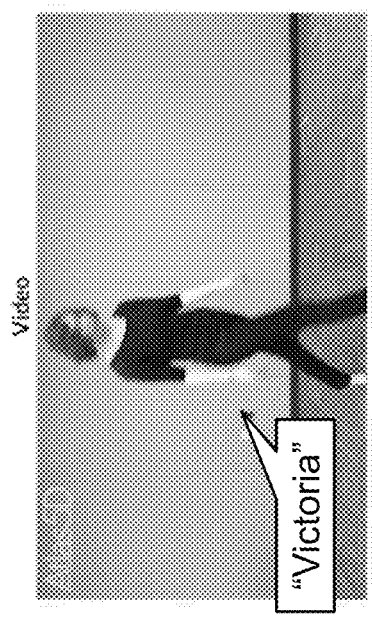
Figure 3D:
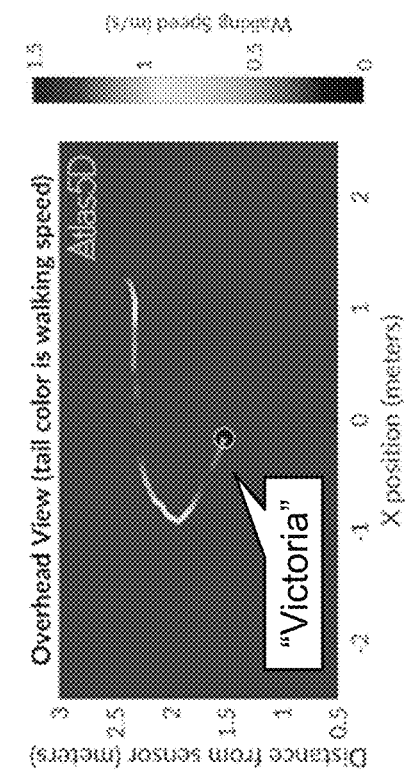
Figure 3C:
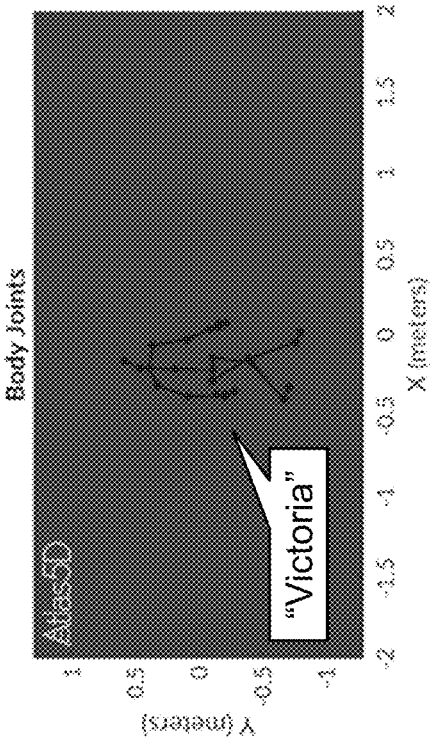

FIGS. 3A through 3M present an example of an output of a system for acquiring and processing depth data as described above. FIG. 3A shows a frame from conventional video for a field-of-view within which a person is walking about a room. FIG. 3B shows a frame of depth data for the same field-of-view and the same moment in time as FIG. 3A. The pixels in the depth data of FIG. 3B are color-coded to represent projected distance from the sensor as described previously, with darker pixels corresponding to positions closer to the sensor. In particular, FIG. 3B shows how depth data helps to preserve the privacy of a person: the overall silhouette of the person is clearly visible, but details such as an image of a face or of a logo printed on clothing, etc., are not. FIG. 3C shows a frame of so-called skeleton data, in which the joints of a person's skeleton are estimated, for the same field-of-view and for the same moment in time as FIGS. 3A and 3B. FIG. 3D shows a frame of so-called trajectory data, in which a person's location and instantaneous walking speed are plotted over time.

Figure 3E:
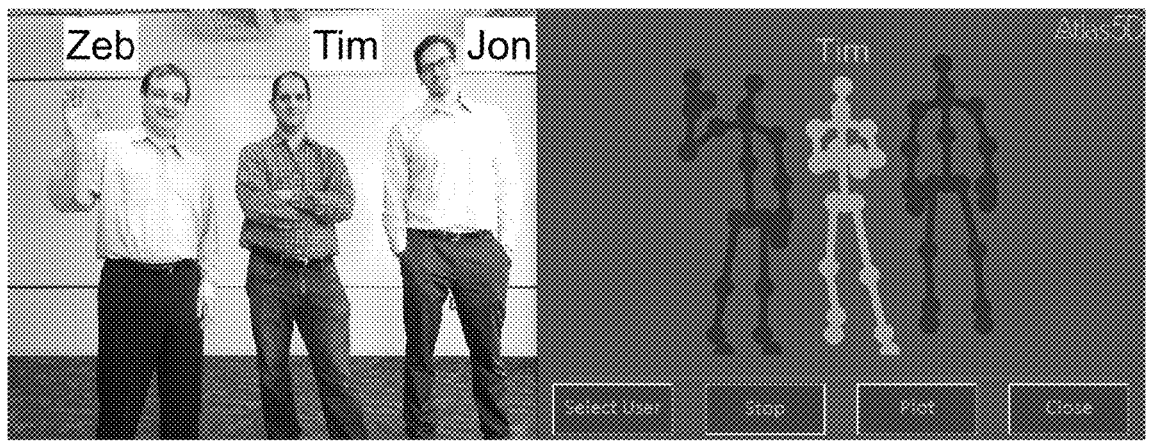
Figure 3F:
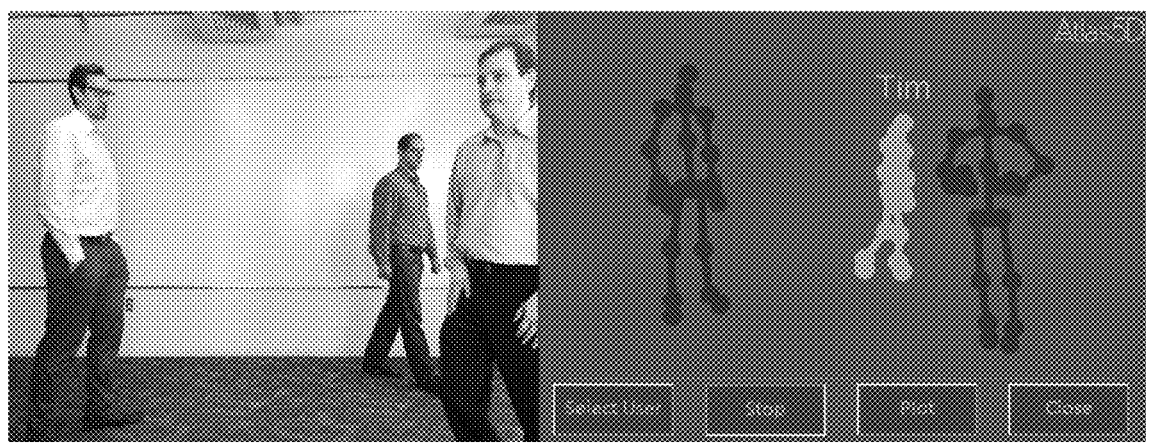
Figure 3G:
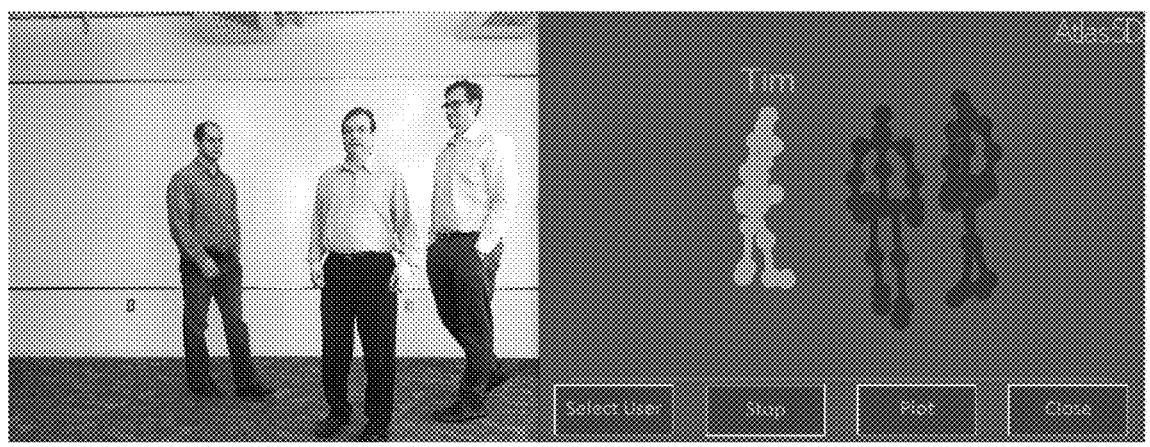
Figure 3H:
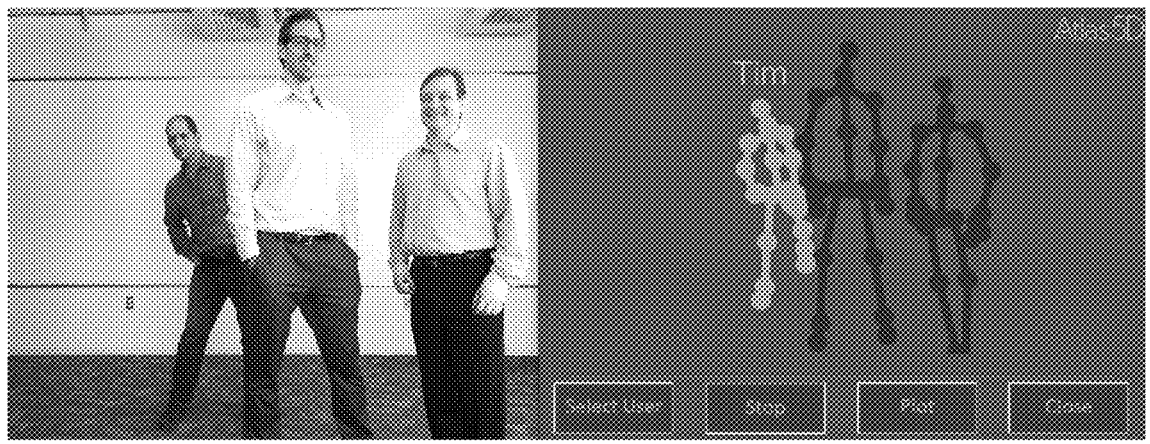
Figure 3I:
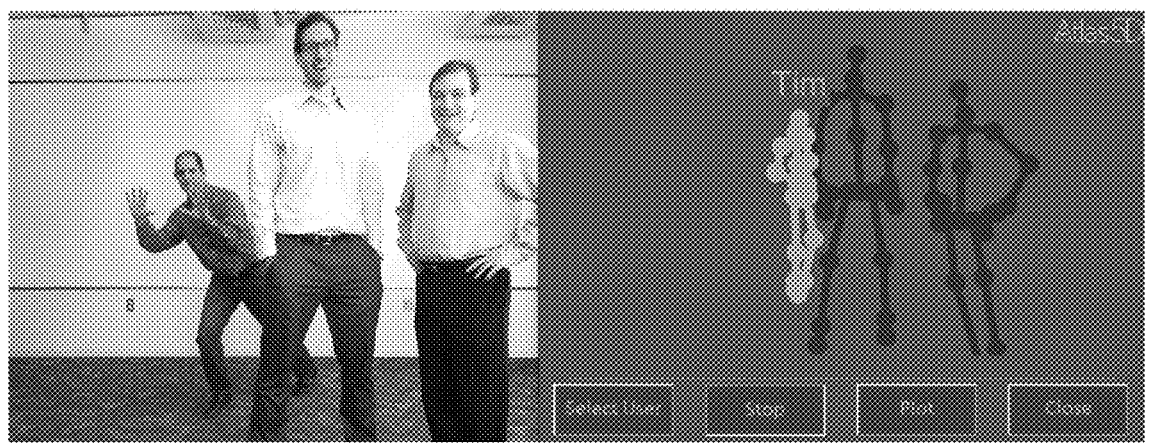
Figure 3J:
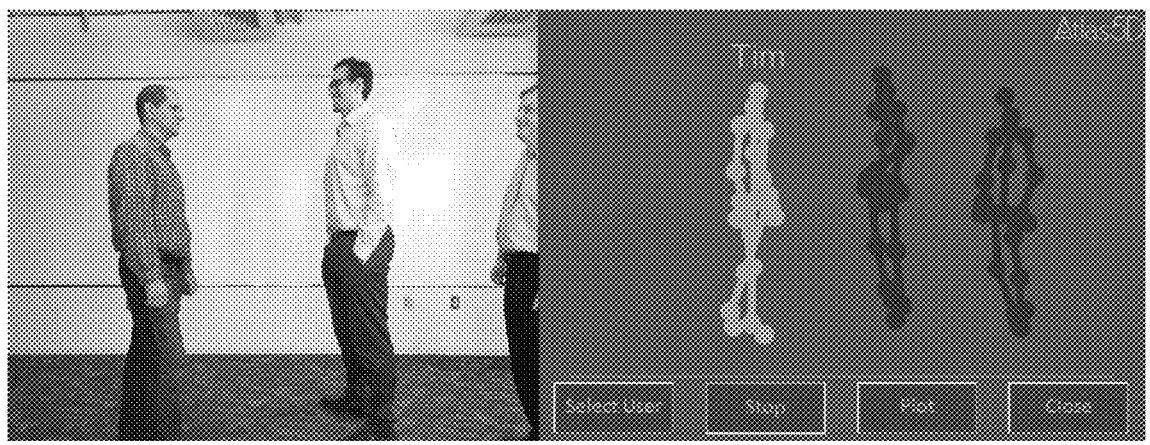
Figure 3K:
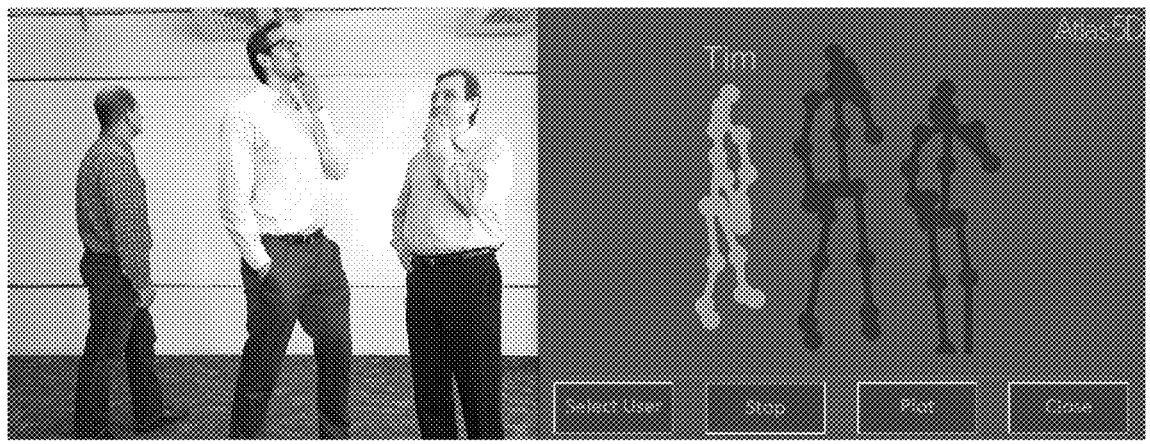
Figure 3L:
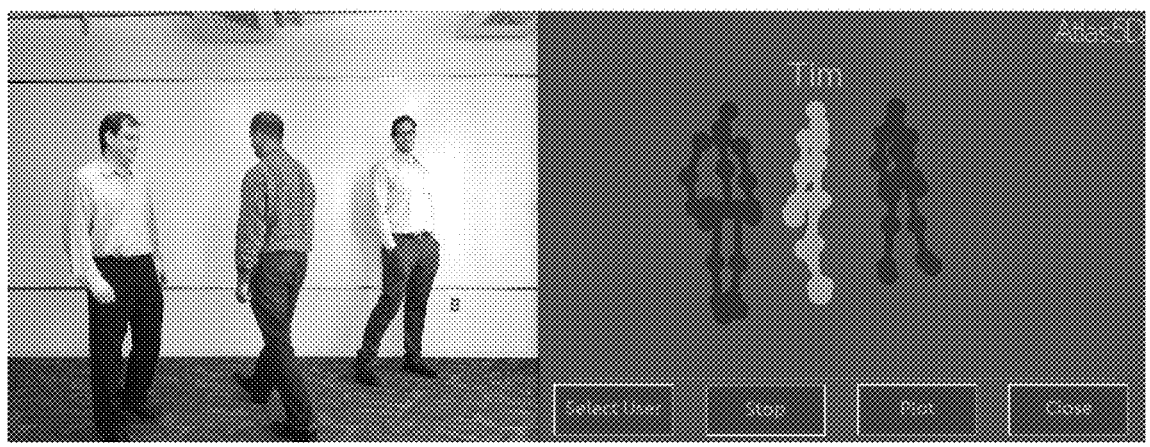
Figure 3M:
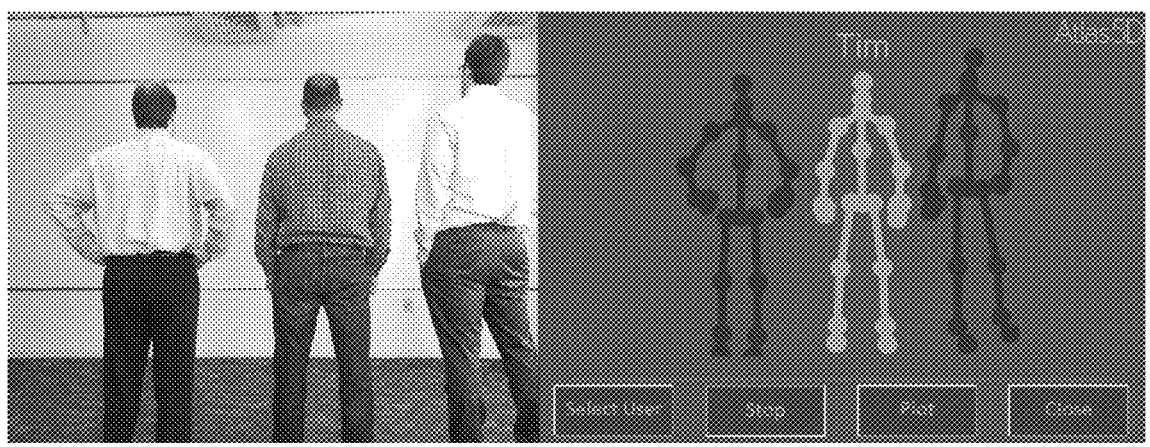

FIGS. 3E through 3M present screenshots of individuals within the field-of-view of the sensor of an embodiment of the present invention which is configured to identify (label) a single person-of-interest—"Tim"—from within a group of persons. In certain embodiments, person identification is performed using depth data only, for example, using an infrared time-of-flight sensor. As shown in FIGS. 3E through 3G, the system, in some embodiments, correctly identifies "Tim" at different distances from the sensor and at different relative orientations to the other persons in the field-of-view. As shown in FIGS. 3H through 3I, the system, in some embodiments, correctly identifies "Tim" when he is partially occluded from view by the sensor (FIG. 3H), or is adopting an unusual posture (FIG. 3I). As shown in FIGS. 3J through 3M, the system, in some embodiments, correctly identifies "Tim" at different orientations relative the sensor (e.g., when he is turned to the side or facing entirely away from the sensor).

In some embodiments, as shown in FIGS. 3E through 3M, the present invention is configured to identify "Tim." However, the system may identify one or more of the other persons ("Jon" and "Zeb"), or identify each of the persons simultaneously. Notably, present-day methods of person identification, such as facial recognition, cannot accurately identify persons under similar conditions (e.g., of distance from sensor, degree of occlusion from the field-of-view, and relative orientation to the sensor) to those demonstrated in FIGS. 3E through 3M.

In certain embodiments, an objective of methods and systems of the present invention is to correctly identify (label) a person in the field-of-view. In the example of FIGS. 3A through 3D, the person in the field-of-view is identified as "Victoria" at the conclusion of the flowchart shown in FIG. 1. In the example of FIGS. 3E through 3M, a single person-of-interest in the field-of-view is identified as "Tim" at the conclusion of the flowchart shown in FIG. 1.

Figure 13A:
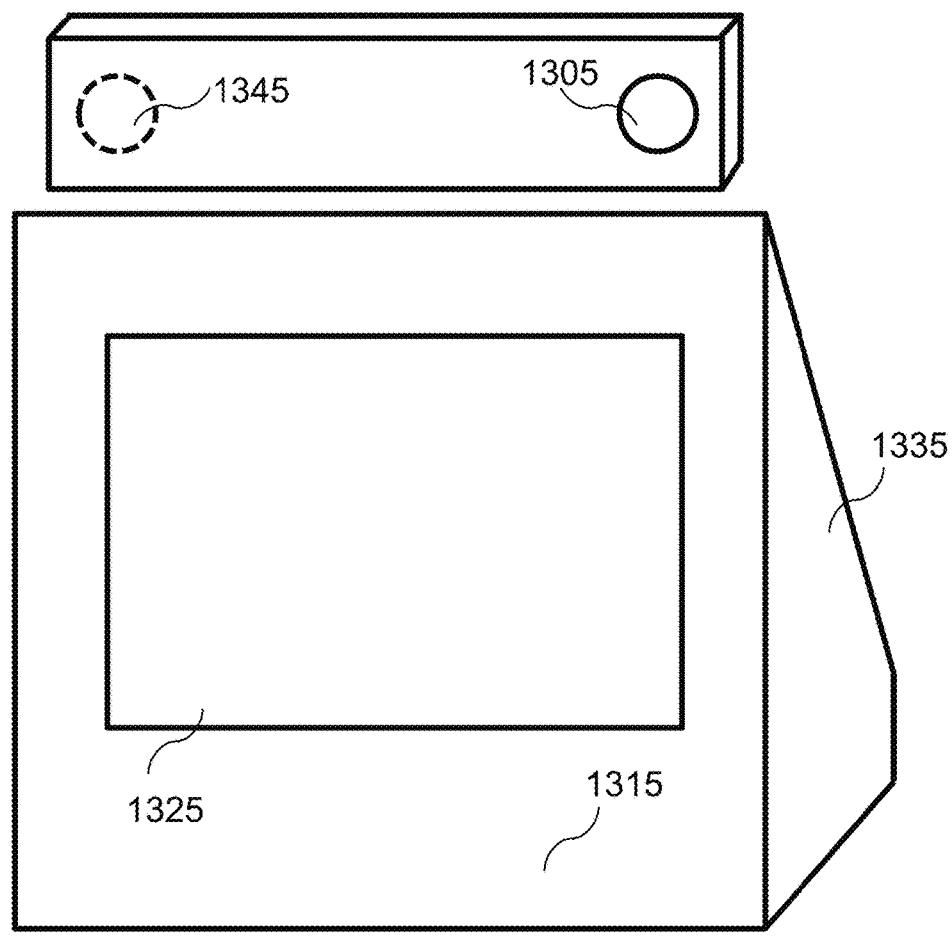
FIGS. 13A through 13D are a schematic and images of an example system for identifying a person and/or identifying and quantifying pain, fatigue, mood, or intent, in accordance with some embodiments of the present invention.

In some embodiments, as shown in FIG. 13A, a system for identifying a person and/or identifying and quantifying pain, fatigue, mood, or intent may contain an infrared time-of-flight sensor 1305 for acquiring depth data. In some embodiments, the system may contain a processor and memory 1315 for storing instructions and a housing 1335 for these components. In some embodiments, the system has a display 1325 for rendering graphical information related to person identity and/or the identity and/or quantity of a person's pain, fatigue, mood, or intent. In some embodiments, the display 1325 shows the representation of persons in the system's field-of-view (e.g., the representations of persons shown in FIGS. 3E through 3M). In some embodiments, the system shown in FIG. 13A may have a camera 1345 to acquire color images of persons (e.g., "Zeb", "Tim", and "Jon") in the field-of-view. In some embodiments, to protect user privacy, photographs of persons are not acquired. For example, the person identification demonstrated in FIGS. 3E through 3M was performed with depth data alone.

Figure 13B:
Figure 13C:
Figure 13D:

FIGS. 13B through 13D present images of an embodiment of the example system depicted schematically in FIG. 13A. For example, the device shown in FIGS. 13B through 13D performed the person identification and captured the screenshots shown in FIGS. 3E through 3M.

In some embodiments, the data acquired by one or more sensors may correspond to raw data direct from the sensor, such as the depth data shown in FIG. 3B; or to measurements derived from raw data, such as the skeleton data shown in FIGS. 3C and 3E through 3M; or to measurements derived from a variety of sources, such as the trajectory data shown in FIG. 3D.

While the embodiments described above provide representative examples, they are not exhaustive and should not be considered limiting. It should be clear to one of skill in the art that a variety of systems and methods for measuring and recording the features of persons and their environment are possible and may be incorporated into the approach described herein.

Person Segmentation

Following the data set acquisition of step 105 and the data set preprocessing of step 110, the ensuing data set may be optionally processed in step 115 in order to segment persons who will be subsequently identified in steps 120 and 125. In other words, in step 115, a collection of pixels in a depth map (or of components of another representation of data) are chosen that correspond to a single person who will be subsequently identified in steps 120 and 125. Segmentation may be performed using one, several, or all of the frames of a data set.

Zero, one, or more than one person may be segmented in each frame of data. In some embodiments, the system and method may use depth data, skeleton data, and/or pixel-label data to segment which pixels correspond to human beings, as distinct from animals, objects, or environment. One or more than one type of data may be utilized for segmentation, and may include in substitution of, or in addition to, depth, skeleton, and pixel-label data, such data types as bolometry, thermographic imaging, clothing texture, hair or skin color, and many other types.

A wide variety of methods can be used for segmentation of persons. In certain embodiments, depth data may be used to segment persons. For example, a collection of spatial objects whose shapes roughly correspond to a sphere (head) and paired cylinders (arms) is likely to be a single person. For example, two blob-like objects in a living room which are both moving, each with a vertical extent exceeding a given threshold above the floor, and each with a horizontal spacing exceeding a given threshold distance, are likely to be two different human beings. In another example, two objects exhibiting differences in radiated-heat signature or in observed clothing texture are likely to be two different human beings.

In certain embodiments, segmentation may be performed using a machine learning and/or pattern recognition technique (e.g., a Convolutional Neural Network, Random Forest, Support Vector Machine, naïve Bayesian machine, and/or clustering technique). For example, in some embodiments, a Convolutional Neural Network may generate an explicit segmentation, producing a boundary, or outline, of a person who will be subsequently identified in steps 120 and 125. Furthermore, in some embodiments, a Convolutional Neural Network can be used to generate an implicit segmentation who will be subsequently identified in steps 120 and 125, without an explicit outline of the person.

So-called mathematical "cascaded-difference" operations may be employed to isolate the approximate shape or silhouette of each person in a field-of-view. Examples are provided as follows. The changing centroid of a silhouette from frame-to-frame may be used to distinguish moving objects, such as people, from stationary inanimate objects. The changing outline of a silhouette from frame-to-frame may be used to distinguish the shape of a human being from that of an animal or inanimate object. The methods described above as well as many other methods may be utilized to segment zero, one, or more than one persons in one or more frames of data over time and/or space.

In the described embodiments, while multiple, distinct persons may be segmented in step 115, their identities are not yet determined. Each distinct (segmented) person may be arbitrarily labeled during step 115 in the interim as, e.g., "person 1", "person 2", "person 3", and so on. Step 120 then determines the feature measurements for each person, and step 125 identifies each person (so that an identity for the person is ruled-in, ruled-out, or established as unknown).

Feature Extraction & Calculation

Once the set of distinct (segmented) persons in a data set is determined by step 115, the data set is then processed in step 120 to extract and calculate features for each of those persons. Zero, one, or more than one person may have their features ascertained by step 120. For each person, zero, one, or more than one feature may be extracted. The same or different features may be calculated for different persons in the same scene or in the same frame; for example, persons of different orientation relative to a sensor, or persons of different heights, may be assigned different features to calculate. The features extracted by step 120 will be subsequently utilized within step 125 to conduct person identification.

In general, because the data analyzed by certain embodiments of methods and systems of the present invention may be incomplete or imprecise, or may be acquired over non-contiguous timeframes, an important task of step 120 is to decide which features can and should be calculated for each person in a frame. For example, if a person is facing away from the sensor(s) at all times in the data-collection period, then the person's facial topography (e.g., nose morphology) will be unavailable and person identification must rely on different feature(s) altogether; whereas if the person is sometimes facing away, and sometimes facing toward, then the availability and quality of potential facial-topography measurements will dictate their relative importance and subsequent incorporation in the person identification of step 125. For example, if a person is facing sideways relative to the sensor(s), and if it is known a priori that the quality of skeleton data generated by a particular sensor is degraded at such a person orientation, then that skeleton data may not be used in the person identification of step 125. In this way, the selection of which features to calculate—and therefore which features are ultimately used in person identification—may vary from person-to-person, and may vary for the same person from frame-to-frame.

In some embodiments, in determining whether or not to calculate a particular feature in step 120, the relative importance of the particular feature as compared to other features may first be determined through an ancillary procedure such as prioritization, ranking, or sub-classification. Further, determining which features can and should be calculated for each person in a frame can be accomplished using a library of features in conjunction with available sensor data that the user deems important for the particular application. For instance, if only 2D imagery is used, then 3D features cannot be used because there is no raw data available with that level of information. Likewise, skeleton features may not be able to be used if a depth camera is not present.

Figure 4:
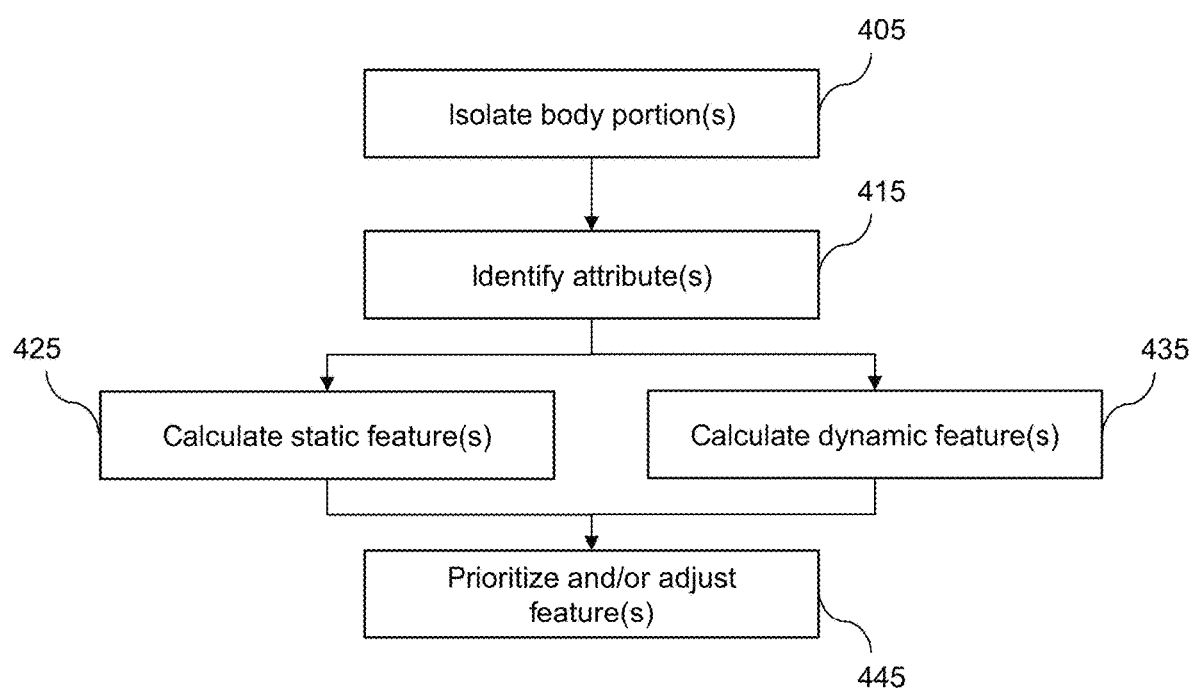
FIG. 4 is a high-level block diagram of an example method for calculating static and dynamic features, according to an illustrative embodiment.

The flowchart in FIG. 4 provides an exemplary method for calculating features for the different persons who were segmented in step 115.

Step 405 isolates portions of the body for each segmented person. Step 405 determines which portions to isolate based on such factors as the nature of the data set, the type of sensor, the amount of non-occluded (i.e., "visible") data available for the person, the library of features available for calculation, and the classification process selected in step 125. In some embodiments, body portions are isolated in step 405 using a machine learning and/or pattern recognition technique (e.g., a Convolutional Neural Network, Random Forest, Support Vector Machine, naïve Bayesian machine, and/or clustering technique). Which portions are isolated may differ from person-to-person, even in the same frame. For example, "person 1" in a frame may have legs isolated because they are visible to a sensor, whereas "person 2" in the same frame may have legs ignored because they are occluded from the sensor by a table.

For example, a data set comprised of depth data, such as shown in FIG. 3B that has been processed to produce a skeletal representation as shown in FIG. 3C may be partitioned into body portions demarcated by approximate joint positions in three-dimensional space, as shown by the line segments of FIG. 3C. Some examples of methods to demarcate body portions are described in U.S. Pat. No. 9,341,464, which is hereby incorporated by reference in its entirety.

As noted above, depending on the position, orientation, and movement of the person in the scene relative to the sensor and to other persons or objects, portions of the persons may be occasionally or entirely hidden from the view of the sensor. As a result, not all portions that together make up the segmented representation of the person may be available in all frames.

In some embodiments, the prioritization (in step 120) of which features to use for subsequent person identification (in step 125) depends on the availability of portions of a person. For example, if a head alone is present, then the shape of the torso may be unused for subsequent person identification. For example, if a head and part of a torso are present for a minimum threshold number of frames, their presence may be sufficient to estimate the rough outline of the remainder of the torso, so that that the shape of the torso is used for subsequent person identification. For example, if a head is present and oriented toward a sensor, then the ear-to-eye distance and the eye-to-eye distance may be used for subsequent person identification. In this way, availability of body portions helps to determine selection of features. In certain embodiments, methods and systems of the present invention may draw upon different availability of different body portions over time to calculate different features over time that all map to the same person and are all used for subsequent person identification.

Step 415 identifies real-world attributes to be measured for each body portion that was isolated in Step 405. The use of the word "identify" in step 415, referring to a generation of a list of attributes, is different from the use of the word "identify" in step 125, referring to a labeling of a person. Examples of attributes, as described above, include volume, circumference, length, spatial location, and mathematical calculations (e.g., calculations performed by a Convolutional Neural Network). Some examples of methods for identifying attributes are described further in U.S. Pat. No. 9,341,464, the content of which is hereby incorporated by reference in its entirety. Each body portion may include zero, one, or more than one attribute. In some embodiments, methods and systems of the present invention may autonomously determine which features to identify in step 415 using methods of machine learning, such as Random Forests, Support Vector Machines, and Convolutional Neural Networks.

Figure 5A:
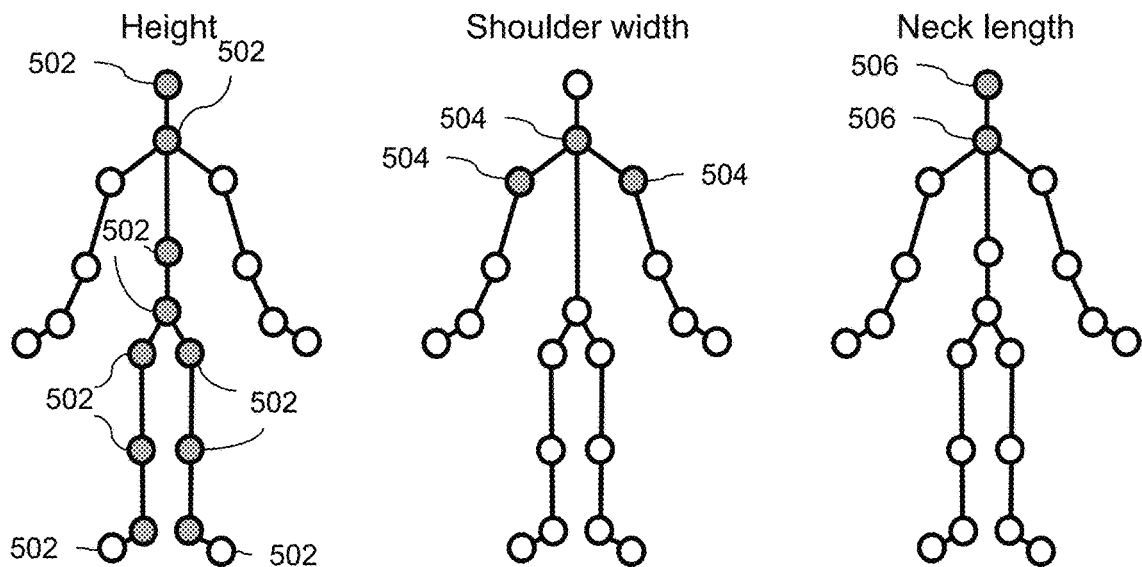

Step 425 calculates static features corresponding to the attributes of step 415. Examples of static features are shown in FIG. 5A. Each static feature may be calculated based on one or more than one frame. Each static feature may be calculated corresponding to: 1) the attributes of a single body portion, 2) the relationship between attributes of different body portions, or 3) the attributes of the environment and/or environmental relationships to one or more body portions. Examples of static features calculated based on the attributes of a single body portion include head size, torso length, torso tilt relative to horizontal (the ground), nose morphology, and eye-to-eye distance. Examples of static features calculated based on the relationship between attributes of different body portions include shoulder-to-elbow length and the ratio of shoulder-to-shoulder-length to hip-to-hip-length. Facial recognition (mathematical eigenface) is another example of a static feature; furthermore, in general, static features may include, incorporate, or otherwise draw upon any subsets of the data of Steps 105 and 110, including (but not limited to) two-dimensional images and/or three-dimensional morphologies of body portions. Note that the calculated measure of a static feature may vary from frame to frame due to, e.g., occlusion and data noise, even when the underlying attribute is constant in the real world.

Although static features may in general be calculated using just a single frame, in practice, often multiple frames are used to calculate static features in order to take advantage of mathematical operations that can account for noise and improve precision, e.g., moving average or median filter taken over a rolling buffer of one or more sequential (not necessarily consecutive) frames.

Figure 5B:
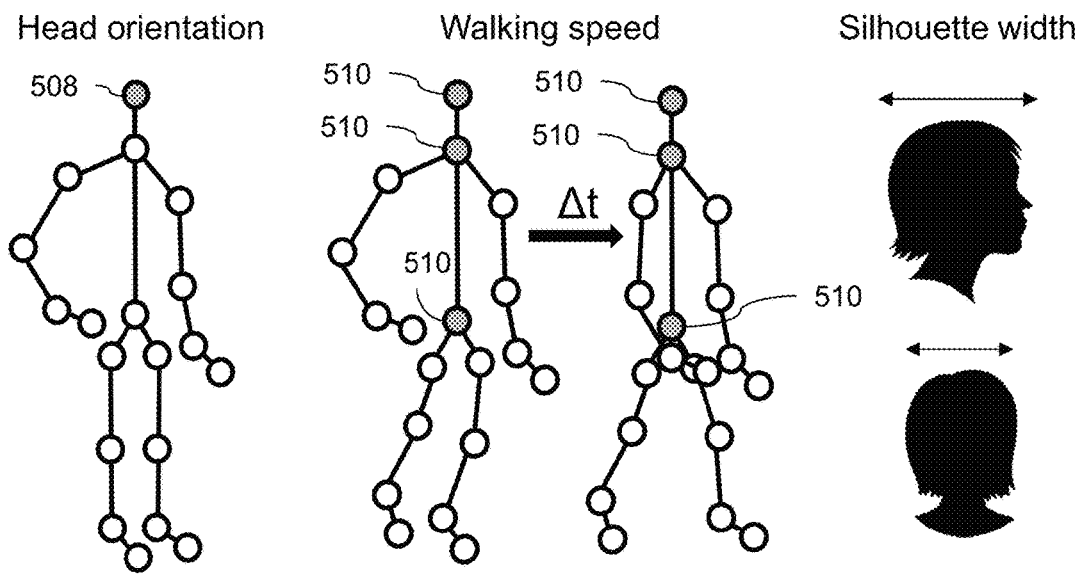

Step 435 calculates dynamic features corresponding to the attributes of step 415. Examples of dynamic features are shown in FIG. 5B. Each dynamic feature may be calculated based on one or more frames acquired at specific times. Each dynamic feature may be calculated based on 1) the variation of attributes of a single body portion over time, 2) the variation of the relationship between attributes of different body portions over time, or 3) the variation of the environment or its relationship to different body portions of the person (described as in #1 and #2) over time. Examples of #1 include head turn, hand raise, body temperature, shape or size of a body portion, and orientation of a body joint relative to the sensor. Examples of #2 include overall body orientation relative to the sensor. Examples of #3 include frequency of the person in proximity to a particular chair in the room, or distance of the person to the sensor. Some dynamic features enjoy multiple measurement pathways: for example, walking speed and stride length may each be calculated by measuring head translation over time (one body portion) or by measuring the position of the two feet relative to each other over time (two body portions).

In some embodiments, a dynamic feature can be calculated from a single frame. For example, instantaneous body orientation relative to a sensor can be estimated from just a single frame of depth data. However, many dynamic features, such as walking speed, require multiple measurements over time. For simplicity, dynamic features are assumed herein to require two or more frames at different times: recognizing, however, that analogous methods remain available for dynamic features that are dependent upon a single frame.

An example of a dynamic feature is walking speed. FIG. 3D shows an example of an embodiment in which the instantaneous walking speed of a person is measured over time. In this embodiment's simplest form, the instantaneous speed of a person is measured by dividing the horizontal translation in three-dimensional space of the person across two frames by the time elapsed between those frames. To improve precision, such calculations may be averaged across collections of multiple frames ("windows") or may use a variety of mathematical operations in order to compensate for noise in the data.

As with static features, some dynamic features may be unavailable for measurement in any or all frames. For example, so-called "heel strike", corresponding to footfall on the floor, might require an unobstructed view of a person's legs and/or feet for a minimum consecutive number of frames in order to measure consecutive footfalls.

Together, steps 425 and 435 extract a set of zero or more static features plus zero or more dynamic features, from a collection of zero or more attributes that were identified by step 415 from zero or more body portions that were generated by step 405 from one or more frames of data.

Step 445 prioritizes and/or adjusts the collection of static features and dynamic features, as described next.

The prioritization of a given feature means choosing whether or not a feature is available and is to be included in further processing steps. (As noted above, features may be aggregated across different sensors, times, and locations; may differ from person-to-person within the same scene or within the same frame; and/or may have different assignations from frame-to-frame, even for the same person.) In some embodiments, methods and systems of the present invention assign quality metrics in step 445 to the features generated by steps 425 and 435. For example, a quality metric might be based on the amount of occlusion of a relevant body portion, or on the mathematical variance (stability) that a feature demonstrates over time. Each quality metric assigned in 445 may also be used in other steps—including, but not limited to, steps 135, 145, and 180—to balance, or to otherwise weight, how a set of features are employed to generate an identification or a conclusion.

The adjustment of a given feature means correcting the feature in response to ambient or environmental conditions. For example, each feature may be so-called "offset-corrected" to ensure that all of the features in a set of features are temporally and/or spatially collocated, if necessary. For example, each feature may be corrected by a mathematical transformation, such as scaling, resizing, or rotating.

FIGS. 5A through 5D show examples of static and dynamic features. As shown in FIG. 5A, attributes 502, 504, and 506 can be used to determine height, shoulder width, and neck length, respectively. Similarly, as shown in FIG. 5B, head orientation can be determined using attribute 508, while walking speed can be determined based on changes in attributes 510 over time. Head-silhouette width can be determined based on measurements of the head. FIGS. 5C and 5D show more examples of static dynamic features, respectively. Categories of features (not exhaustive) include, for example, features which correspond to the body, or to a portion thereof (such as, e.g., the head, shoulder, arm, or leg). Within each category of features, the features can be static or dynamic. Further examples of features are shown in: U.S. Pat. No. 9,341,464, its accompanying text, and its FIGS. 4, 12, and 13 and PCT Application No. PCT/US2012/058534, its accompanying text, and its FIGS. 4 and 17; the contents of each of which are hereby incorporated by reference in their entireties.

FIG. 5E illustrates how features relate to bodyprints, and is described further below.

Figure 6:
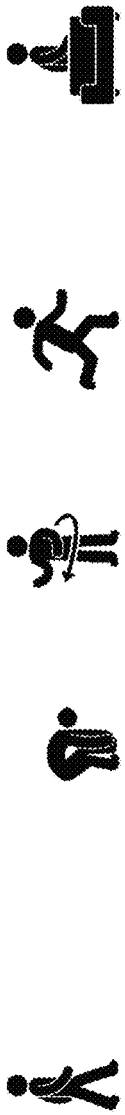
FIG. 6 is a schematic illustrating a series of movements, a set of example static and dynamic features captured in a series of frames, and the results of classification of persons according to an illustrative embodiment of the present invention.

FIG. 6 presents an example of calculating static features and dynamic features for a person moving within a scene. For simplicity, only one person is described in FIG. 6. However, in general, features for multiple persons may be extracted simultaneously. In the example of FIG. 6, the static features to be extracted are height, right leg length, and shoulder-to-shoulder width; and the dynamic features to be extracted are angle of gaze, walking speed, and head silhouette width.

Static features may be calculated based on one or more frames. In FIG. 6, the static features may be calculated from the single frame to which they correspond. In some embodiments, the static features are calculated based on a window of multiple contiguous frames (e.g., by averaging). In some embodiments, the static features are calculated based on any desired combination of one or more frames, which may be non-contiguous.

Dynamic features may be calculated based on two or more frames. In FIG. 6, the dynamic features may be calculated from the single frame to which they correspond when compared to the immediate next contiguous frame. In some embodiments, the dynamic features are calculated based on a window of multiple contiguous frames (e.g., by averaging). In some embodiments, the dynamic features are calculated based on any desired combination of two or more frames, which may be non-contiguous.

As illustrated in FIG. 6, static features tend to show lower variability than dynamic features. Static attributes such as height change only slowly in real life, and so their corresponding features exhibit relative stability when calculated from sensor data. But dynamic features such as walking speed or head-silhouette width (i.e., the head cross-section exposed to the sensor) change more rapidly. As a result, dynamic features generally exhibit greater variability when calculated from sensor data, especially during changes in posture or orientation. As described earlier, the amount of variability in a feature—whether dependent on time, space, velocity, pixel-count, angle, or some other unit of measurement—is dependent on the application and may vary from situation to situation.

As shown in FIG. 6, some features may be unavailable or non-computable in any given frame or series of frames. For example, in FIG. 6, when the person walks behind the couch, the person's legs become occluded from the view of the sensor, such that leg length becomes temporarily unavailable. For example, in FIG. 6, when the person stops to tie a shoe, the system is unable to ascertain within an adequate precision the anatomic landmarks that are needed to calculate walking speed, so that walking speed becomes temporarily non-computable. For example in FIG. 6, when the person walks behind the couch, walking speed continues to be calculated as a feature because walking speed may be determined from positional changes in the person's head even while the person's legs are out-of-view.

In general, some features may be calculated from other features, and there are often multiple different pathways available to calculate a given feature. For example, in FIG. 6, the feature of shoulder-to-shoulder width could be calculated from direct measurements of the location of each shoulder, or indirectly by summing two other features: left-shoulder-to-top-of-spine width and right-shoulder-to-top-of-spine width. For example, in FIG. 6, the walking speed could be calculated from the average change in spatial position for head alone; or from the average change in spatial position for a combination of head, neck, and spine; or from the spatial positions of sequential landing points of left and right feet on the floor. The average walking speed over a duration of time could be calculated directly from a collection of frames over that duration or indirectly from the instantaneous walking speeds calculated on a frame-by-frame basis (e.g., by taking their weighted moving average).

As shown in FIG. 6, once the desired features are calculated for one or more frames, the features are sent to the classifier in step 125 in order to perform person identification. The classifier may receive a set of features such as 630 corresponding to a single frame (a single column in FIG. 6), or a set of features corresponding to multiple frames (multiple columns in FIG. 6), or any subsets of features thereof. As described above, features may be adjusted (e.g., latency-corrected or spatially collocated) in order to adjust for timing delays or biases in the sensors or calculation methodologies.

Person Identification

The discriminatory ability of a particular feature to successfully identify a person depends on 1) the feature's fidelity (how well the feature can be measured), and 2) the feature's predictive power (how specific the feature is to that person).

The fidelity of a feature depends on the composition of the scene (i.e., the field-of-view and the objects within it), the type of sensor being utilized, and the type of data being acquired. For example, the fidelity of a person's height measurement will be better when the person is standing straight up and worse when the person is crouching or huddled. The fidelity of any feature will be worse whenever the relevant portions of the person are occluded by an object such as furniture.

The predictive power of a feature depends on the degree to which that feature differs among the persons who are to be identified. For example, the predictive power of height is poor for identical twins, but excellent for a pair of individuals whose height is significantly different.

Continuing this example: the feature of height, when used alone, may lack fidelity (fluctuating based on the person's posture, becoming unavailable when the person is occluded) and lack predictive power (because many people can be of similar height). In general, the power of a feature may change over time, becoming stronger at some instants (e.g., when the person is standing straight up) and weaker at others (e.g., when the person is tying a shoe).

In certain embodiments, methods and systems of the present invention overcome the weakness of relying on any fixed set of features through the mechanism of mixing-and-matching a combination of features, as determined by the available scene, sensor, data, and library of known and computable features. The combination of features provides a highly-specific "bodyprint" for each person to be identified in step 125.

FIG. 5E illustrates two examples of bodyprints. Bodyprint 580 describes that a person possessing measured height between 180 and 200 centimeters with a measured head circumference between 58 and 60 centimeters, walking at an average speed of between 0.5 and 1 meters/second, and wearing glasses may be identified as "Bob" with a numerical bodyprint-score (precision estimate) of 0.95. Bodyprint 590 describes that a person possessing measured height between 170 and 180 centimeters with a measured ear-to-eye distance between 14 and 16 centimeters and walking at an average speed of between 1 and 2 meters/second may be identified as "Clara" with a numerical bodyprint-score (precision estimate) of 0.80. The bodyprints of FIG. 5E are only illustrative examples. In practice, any number and combination of features may be incorporated into a bodyprint, and a bodyprint may include zero, one, or more than one bodyprint-score. Any bodyprint-score may be used, or alternately may be ignored, by classifier 700.

FIG. 6 shows simplified examples of two different bodyprints 610 and 620, each of which possesses a combination of features sufficient for subsequent step 125 to identify the person described in FIG. 6. As shown in FIG. 6, different bodyprints may be ascertained for the same person at different moments in time, in different frames, and in different collections (sets) of frames.

As described earlier, some or all of the features relevant to a bodyprint may result from mathematical operations that are not readily or intuitively grasped by the human brain. For example, a Convolutional Neural Network (CNN) repeatedly applies a set of mathematical operations onto input data, yielding architectural layers which represent a flotilla of unique features deriving from, or describing, the input data (such as colors, shapes, textures, and patterns). Few of these features convey easily recognizable significance to a human viewer, but they nonetheless can be used to generate a manifestly viable bodyprint, supplying the same utility and engendering the same handling as more-familiar features like walking speed and height.

The term bodyprint is employed to highlight that some or all of the features can be derived from the morphology or motion of the person's body; the person's bodyprint is viewed as a large-scale analogue to the person's small-scale fingerprint, in that both bodyprint and fingerprint are capable of identifying that person. The combination of features utilized (by certain embodiments of methods and systems of the present invention) as a bodyprint may vary over time, over space, and over person. For example, if a desired feature needed for one bodyprint becomes temporarily unavailable over a series of frames, thus preventing that specific bodyprint from being used, the present invention can substitute an alternate bodyprint—equivalently, an alternate combination of features—which are available for those same frames. In some embodiments, the set of producible bodyprints is deliberately constrained to exclude color image data (i.e., photographs) in order to better protect privacy.

The provision for bodyprints as described herein explains why dynamic features (such as walking speed) may be just as important as static features (such as height) for person identification: the manner in which a person's attributes change over time and/or space (e.g., the person's pattern of movement or behavior) may describe a highly-specific signature for that person and may remain available in complex or crowded environments where the complementary availability of static features is limited. For example, if two persons occupy a household, both of similar height and build, where one person is very old and one person is very young, then the average walking speed (dynamic feature) over a duration of a few seconds may prove sufficient to identify each of the two people even though height and build (static features) are not sufficient on their own.

The importance of having access to both static and dynamic features is emphasized whenever a person must be identified either: 1) passively, so that the person does not need to perform a prescribed or stereotyped action, or 2) at a distance, for example, located more than one meter from a sensor. In either of these two situations, often-used and/or single-source biometrics such as fingerprints become impossible to acquire.

Figure 7:
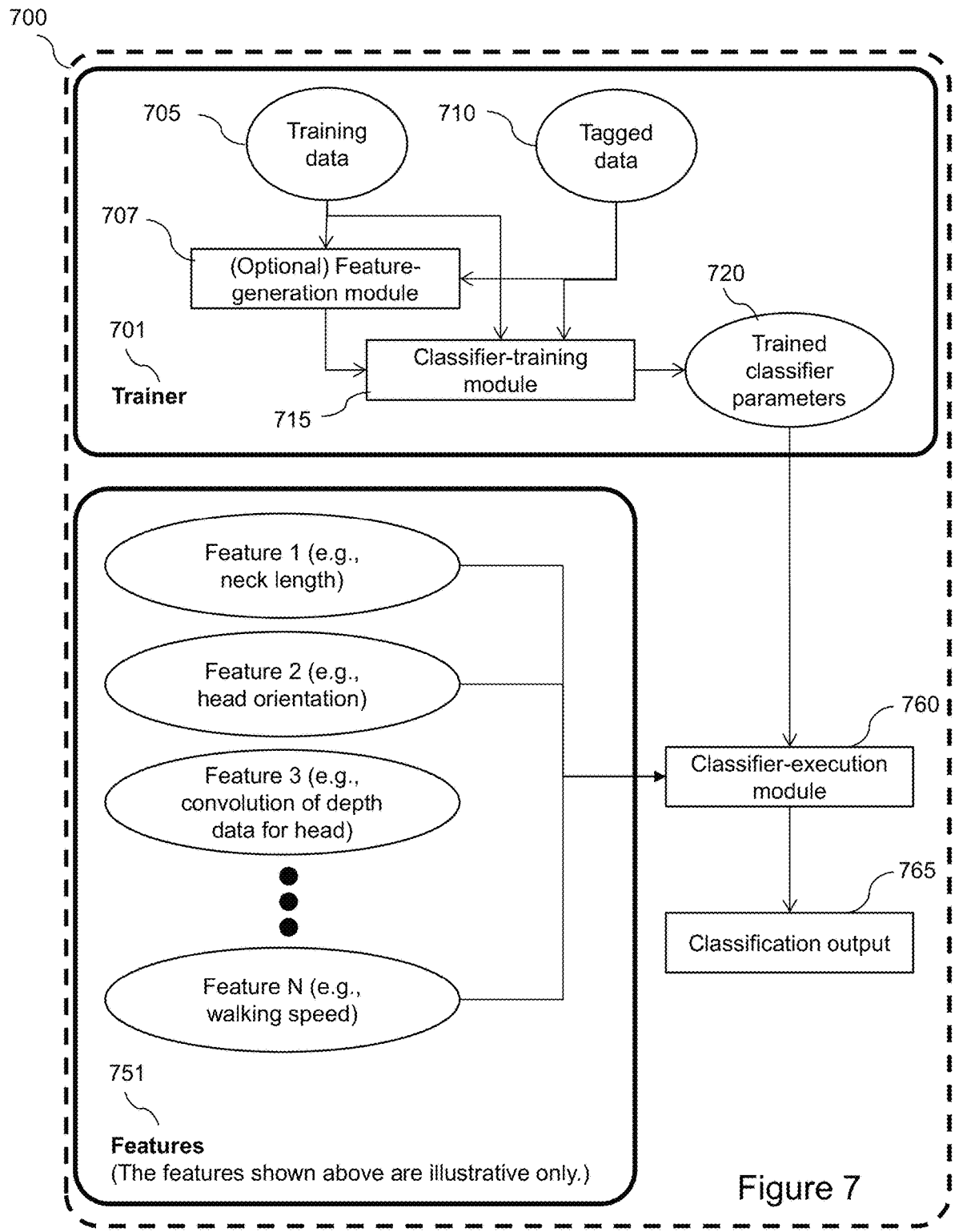
FIG. 7 is a high-level block diagram of an example method for training a classifier for person identification, according to an illustrative embodiment.

FIG. 7 shows a high-level block diagram of a classifier 700. In some embodiments, the classifier is a component of the operation of step 125. FIG. 7 shows one type of classifier 700, but many other types are available. The example of a classifier 700 shown in FIG. 7 is first trained (in advance) by the trainer 701 in order to recognize a specific person-of-interest (e.g., "Bob"). The training data 705 consists of pre-selected data frames, at least some of which contain a known representation of the person-of-interest. The tagged data 710 consists of pre-specified labels, or "tags", which are known to correctly identify the representation(s) of the person-of-interest within the training data 705. The optional feature-generation module 707 uses the training data 705 and the tagged data 710 to calculate features, as described earlier. The classifier-training module 715 receives as input a combination of: zero or more outputs of the feature-generation module 707; zero or more components of the training data 705; and zero or more components of the tagged data 710, and returns as output a set of trained classifier parameters 720 that correspond to the person-of-interest. The trainer 701 may use a wide variety of methods of computer vision, machine learning, and pattern recognition; examples include: Random Forests, Support Vector Machines, and Convolutional Neural Networks, as described earlier.

Subsequently, the classifier-execution module 760 is employed to identify the person-of-interest in de novo data. The classifier-execution module 760 receives as input the earlier set of trained classifier parameters 720, which were generated by the trainer 701, along with a new set of features 751, which are received from step 445 of FIG. 4, and returns as output a classification output 765 which identifies each person-of-interest. The classifier-execution module 760 may use a wide variety of methods of computer vision, machine learning, and pattern recognition: again, examples include Random Forests, Support Vector Machines, and Convolutional Neural Networks.

The classification output 765 proposes the identity of zero, one, or more than one persons who appear in zero, one, or more than one frames of data. Each person identification provided by the classification output 765 may be a rule-in identification (e.g., "this person is probably Bob"), a rule-out identification (e.g., "this person is probably not Bob"), or an unknown identification (e.g., "there's not enough information to tell whether this person is or is not Bob").

An important special case of rule-out identification is the identification of a person as "other", indicating that no identity match was found and it is likely that identity of the person is not contained within a set of known bodyprints. For example, a guest visiting a family household (for which the family's bodyprints, but not the guest's, may be known) could be identified as "other". Being able to identify a person as "other" may improve computational performance by signaling that no further features need to be calculated for that person, at least for so long as that person is within sensor range.

In another important special case, in some embodiments, the system only needs to distinguish a single person-of-interest from everyone else in the world ("other"). In these embodiments, the system seeks only to identify whether or not a person is, for example, "Bob". This may improve computational performance because the system is not trying to identify whether a person is "Bob" or "Clara" or "Sigi" or "Suse" or etc.; the system is only trying to identify "Bob" versus "not-Bob". The resulting reduction of computational overhead and search space may lead to improved precision and speed of the system in its task of person identification. For example, in a family household where the mother is affected by multiple sclerosis, which is a medical condition whose severity can be estimated by average walking speed, certain embodiments of methods and systems of the present invention may be employed to 1) identify whether each passerby is "mother" or "not-mother" and 2) if "mother", then measure and record her current walking speed, while foregoing measurements of anyone else (i.e., anyone who is "other").

In some embodiments, a confidence score is assigned to each person identification. The confidence score is a probabilistic measure of how likely the machine learning method "believes" that it has correctly identified the person. For example, a Support Vector Machine, Convolutional Neural Network, or Random Forest may divide the number of positive "votes" by the number of branch paths encountered during execution, producing a numeric confidence score between zero and one. The confidence score, if any, of each person identification may vary from person-to-person, or may vary from frame-to-frame or across collections (sets) of frames even for the same person. The determination of a confidence score, if any, that is assigned to an individual person identification may optionally include calculations that are based on zero, one, or more than one bodyprint-scores assigned to zero or more bodyprints.

Figure 8:
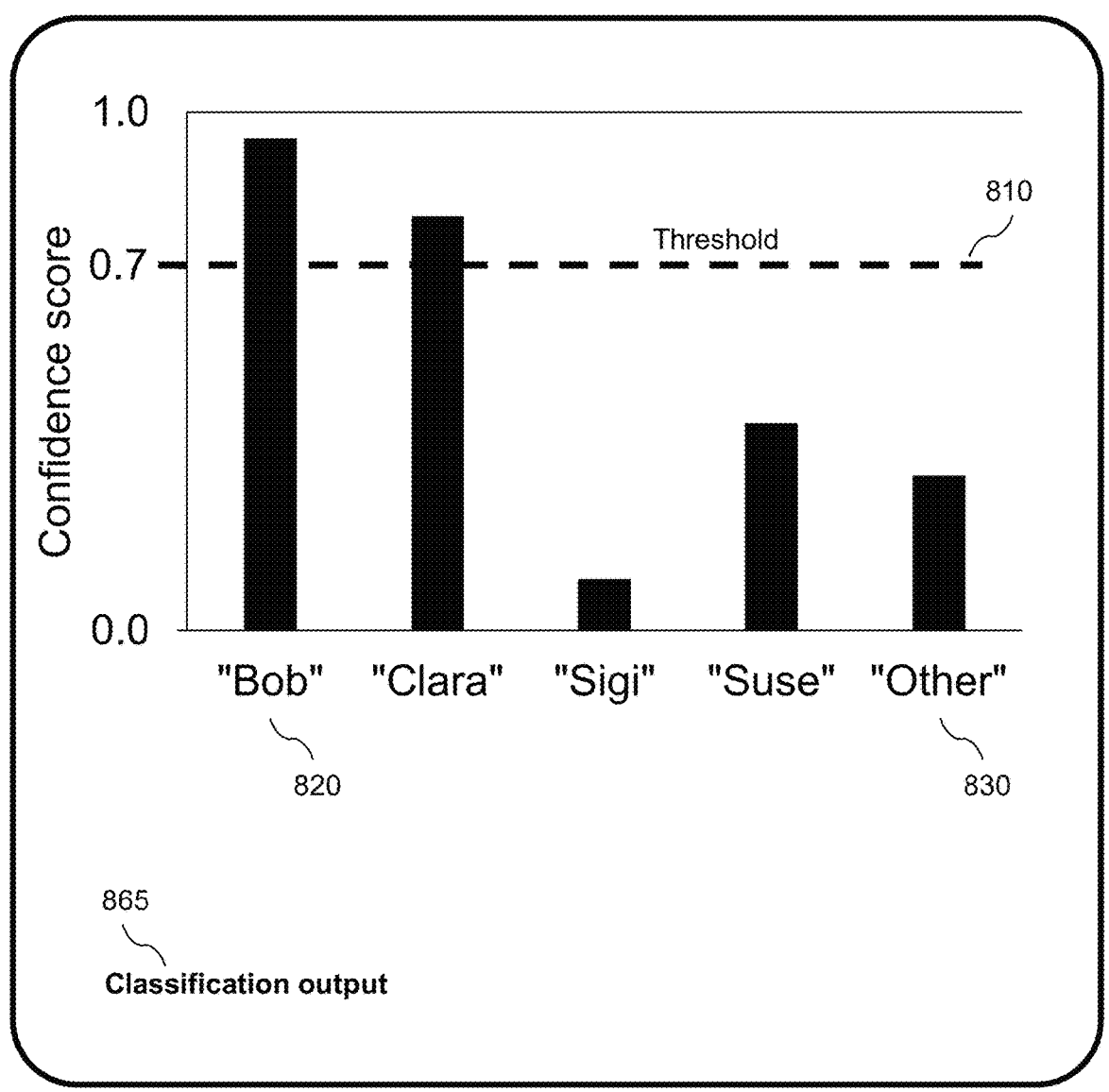
FIG. 8 is a schematic illustrating an example output of a classifier for person identification, according to an illustrative embodiment.

FIG. 8 illustrates an example of confidence scores which could be provided by the classification output 865 (which is the same as like-numbered 765). In FIG. 8, an exemplary method is attempting to identify whether a person is "Bob", "Clara", "Sigi", "Suse", or "Other". In each case, the method generates a confidence score between 0 and 1. For example, a confidence score 820 of 0.95 for "Bob" means that the classifier is 95% confident that the person-of-interest is "Bob" and 5% confident that the person-of-interest is "not Bob". The various confidence scores in FIG. 8 are independent of each other and thus do not sum to 1. In FIG. 8, a threshold score 810 of 0.7 means that person(s)-of-interest with confidence score(s) above 0.7 are retained, while those with confidence scores below 0.7 are discarded. In FIG. 8, the example person-of-interest could be only "Bob" or "Clara" (not "Sigi," "Suse," or "Other"), because both of their corresponding confidence scores are above 0.7. The person-of-interest is also more likely to be "Bob" than "Clara", because the confidence score for "Bob" is higher than the confidence score for "Clara".

In the example of FIG. 8, there are two candidate names that each exceed the threshold for identification: "Bob" and "Clara". In some embodiments, "Bob" is returned as the person's identification, because the confidence level of "Bob" is higher than "Clara". On the other hand, in some embodiments, "unknown" is returned as the person's identification, because "Bob" and "Clara" are considered too close in confidence to make a call. In general, in some embodiments, the handling of situations where multiple confidence scores exceed the threshold is determined by system configuration or operator preference.

In certain embodiments, a confidence score is not readily assigned. For example, methods such as scaling and thresholding or methods involving coordinate transforms or linear (or nonlinear) mapping techniques do not generally produce a consistent confidence score. However, such methods may be augmented to produce a derived confidence score.

Optionally, the classifier may not compute or utilize a confidence score within classification output 765, or the classifier may not require or utilize training data 705. Instead, the classifier may use heuristic methods, cutoff thresholds, and/or other means of categorization. In these and similar cases, the classifier may be more appropriately termed a "categorizer". For example, a set of features obtained when Bob walks through the field-of-view may be compared to known bodyprints "Bob", "Clara", "Sigi", and "Suse" by using Euclidean distance (the mathematical dot-product). Subsequently, Bob might be identified as "Bob" by choosing the smallest Euclidean distance as a heuristic. For example, a set of features obtained when the sole child of a household walks through the field-of-view may be compared to known bodyprints "mom", "dad", and "child" by using a cutoff threshold (e.g., for height), and subsequently the child is identified as "child" by selecting the sole bodyprint possessing height lower than the cutoff threshold (for height). Each of these examples is better-described by the term "categorization" than by the term "classification". Herein, for brevity, we use the word "classification" as a catchall term that encompasses both "classification" and "categorization".

Person Registration

In some embodiments, it may be desirable to provide certain embodiments of methods and systems of the present invention with known features and/or bodyprints of expected persons-of-interest, so that the classifier 700 and its trainer 701 will have a priori knowledge with which to operate. For example, if such an embodiment is placed in the aforementioned family household where the mother is affected by multiple sclerosis, it may be desirable to provide known features and/or bodyprints of all the household inhabitants to the system in advance. Through this approach, the system will more precisely identify the mother and screen out other family members. The procedure wherein one or more known features and/or bodyprints are provided to a system or method is called registration, and a person thus entered into the system is said to have been registered.

In some embodiments, the system may only need to register a small number of people, such as, say, four to six members of a family household, or even just a single person-of-interest. As described above, constraining the number of bodyprints to such a small extent can increase system performance because now the system only needs to identify those few household members versus "other."

Procedures through which a classifier may be trained with registration data are well known to those skilled in the art. In brief, registration data may be obtained automatically (by having a person of known identity prospectively undergo measurement), manually (by having a human operator retrospectively leaf through data sets and manually label the people represented within), or by a combination thereof. For example, instructions may be displayed on a computer screen instructing a particular person-of-interest to perform a series of known or prescribed movements in front of a sensor. These movements are then translated into a bodyprint. A person-of-interest may temporarily wear a bracelet that broadcasts the person's identification, such that whenever the person-of-interest traverses a sensor's field-of-view (while wearing the bracelet), the system acquires registration data for that person.

The specific method by which registration occurs may be dependent on the mechanisms of the underlying classifier 700. In some embodiments, registration is performed on one, some, or all available features of interest. In some embodiments, registration and/or training continue indefinitely, even during regular everyday operation, so as to accommodate ongoing changes in a person's bodyprint (e.g., haircut, weight change, wearing a bulky jacket). In some embodiments, registration and/or training are repeated at predefined intervals, such as monthly or yearly. In some embodiments, registration and/or training are repeated upon ad hoc or arbitrary events, such as a change in the appearance of a person-of-interest, or a desire to switch identification from one person-of-interest to another, or a performance improvement made to the classifier 700. In some embodiments, a person-of-interest him/herself is asked to verify the tagging (labeling) of his/her representation within a data set by a registration procedure and to make corrections where the tags are wrong or missing.

In some embodiments, during registration, the person to be registered stands, sits, turns, or rotates in view of the sensor, with or without some body portions occluded. In some embodiments, during registration, the person to be registered carries out a pre-defined set of movements (e.g., walking around to cover the entire field-of-view, or standing in a variety of orientations relative to the sensor). In some embodiments, a pre-defined set of movements includes walking along: a line, a rectangle, a circle, or a figure-eight. In some embodiments, the registration procedure is unsupervised: that is, the person to be registered is given instructions as to how to move, and subsequent adherence to the instructions is the responsibility of the person. In some embodiments, the registration procedure is supervised: that is, the disclosed technology tracks the person in real-time during the registration, and provides corrective instructions or feedback if the person deviates too far from the desired registration movements. In some embodiments, the disclosed technology ascertains the quantity and quality of registration data in real-time as the data are obtained, and informs the person when to: continue the current movement, switch to a different movement, or end the registration procedure. In some embodiments, the disclosed technology is able to detect a paucity of a specific type of registration data, and upon doing so, to instruct the person to go to a specific location or to adopt a specific movement in order to "fill in" the missing data.

In some embodiments, a system or method acquires data and performs steps 105-120 (but not step 125) for some period of time without identifying any persons-of-interest, up until it receives registration data, at which point the system or method retrospectively performs step 125 using all the previously-gathered data. As noted above, registration and classification may each be performed in a manual, semi-autonomous, or fully autonomous manner, and different registration and classifications may employ the same or different data, features, and/or bodyprints. Semi-autonomous and fully autonomous methods of registration may include, for example, machine learning and pattern recognition.

As noted above, registration is not required for a system or method to perform identification. For example, as noted above, the system may instead use heuristic methods, cutoff thresholds, and/or other means of categorization.

In some embodiments, the data, features, and/or bodyprints employed in a method or system are chosen such that visual image data, such as photographs and videos and facial recognition, are excluded in order to protect privacy. In some embodiments, the need for privacy may be less prominent, so that the data, features, and/or bodyprints employed may include visual image data, such as photographs and videos and facial recognition. In certain embodiments, an important advantage of a system or method is that it can offer different levels of privacy protection that can be tailored for different applications.

Relationships Between Features and Mental Perception(s) and/or Intent(s)

Use of a Pre-Determined Relationship

FIG. 1B is a flowchart of an example of a method to characterize a movement, behavior, or activity—and thereby a mental perception (e.g., of pain, fatigue, or mood) or intent—according to an illustrative embodiment. In FIG. 1B, a conclusion is determined from a pre-determined relationship.

With the exception of steps 135 and 155, all of the steps of FIG. 1B are identical to their like-named counterparts in FIG. 1A.

The calculation of features in step 120 may employ techniques from signal processing, computer vision, and/or machine learning. For example, a side effect of person segmentation in step 115 may be to locate the spatial positions of the person's anatomic joints; the relative positions and movements of these joints then become features in step 120. For example, the posture of a person may be used as a feature: if the posture degrades slowly throughout the day, then it may be inferred that the person is becoming fatigued. For example, a Random Forest construct from machine learning may receive as inputs the positions of a plurality of joints of a person ("skeleton data"), and produce as output a confidence level that the person feels psychologically depressed. For example, a Convolutional Neural Network construct from artificial intelligence may receive as input a three-dimensional shape of a person's body ("depth data"), and produce as output a confidence level that the person intends to commit a malicious act. For example, the Fourier analysis of the verbal utterances of a person may be used as a feature: if, suddenly, the voice's volume becomes louder and pitch becomes higher, then it may be inferred that the person is becoming agitated.

Step 135 correlates the features generated by step 120, which identify and quantify a person's movement, activity, and behavior, against a pre-determined relationship to determine a conclusion about pain, fatigue, mood or intent. Examples of pre-determined relationships and conclusions are given herein above.

Step 155 outputs the conclusion(s) generated by step 135. Examples of conclusions, according to illustrative embodiments, are shown in FIG. 10.

Use of a Learned Relationship

FIG. 1C is a flowchart of an example of a method to characterize a movement, behavior, or activity—and thereby a mental perception (e.g., of pain, fatigue, or mood) or intent—according to an illustrative embodiment. In FIG. 1C, a conclusion is determined from a learned relationship.

With the exception of steps 145, 165, and 175, all of the steps of FIG. 1C are identical to their like-named counterparts in FIGS. 1A and 1B.

Step 145 compares the features generated in step 120 against known exogenously supplied attribute(s) or data, called the "ground truth" 175. The output of step 175 is a correlation between features and a learned relationship, wherein the learned relationship is established using features and any ground truths supplied in step 175. In this way, the learned relationship may be modified or updated during the method of FIG. 1C using the calculated features. The process of generating, modifying, or updating a correlation, association, or learned relationship is called "training" and is accomplished via techniques of computer vision and machine learning. Examples of such techniques include: Support Vector Machine, naïve Bayes classifier, Random Forest, decision tree, and neural network (including Convolutional Neural Network).

For example, a learned relationship generated by step 145 might consist of a threshold: "if a person's walking speed is over 0.5 meters per second, then the level of fatigue is minimal". For example, a learned relationship generated by step 145 might consist of an algebraic equation: "a person's change in fatigue from last week is the percent change in walking speed plus the percent change in posture over the same period of time". For example, a learned relationship generated by step 145 might comprise a multitude of numerical weights embedded within a neural network construct, such as a Convolutional Neural Network.

Correlating Features with Relationships

Figure 9A:
FIGS. 9A through 9D illustrate examples of correlating features to relationships to determine conclusions, according to illustrative embodiments.

In FIGS. 1B and 1C, Steps 135 and 145 correlate features to relationships in order to determine conclusions. The pre-determined relationships of step 135 can be constructed from analytical methods such as heuristics, rulesets, and statistical methods. For example, using biomechanical reasoning, one can determine that a person's stride length can be measured by looking at the position of the head over time. The head's acceleration is at a minimum during each footfall. By calculating the distance between head locations at sequential acceleration minima, it is possible to indirectly measure the person's stride length—thus defining a pre-determined relationship, as illustrated in FIG. 9A.

The learned relationships of step 145 can be generated by machine-learning methods such as (for example) Support Vector Machines and Convolutional Neural Networks. The ground truth 175 may be provided, for example, by scientific literature; by human input; or by other machinery or computations. For example, a ground truth for fatigue could be data from a survey administered to a person every few days with questions pertinent to self-reported fatigue level. Those survey responses could be used to train a machine-learning algorithm, e.g., a naïve Bayes classifier, in step 145 to maximize correlation between an input set of features 120 and the ground truth 175 (self-reported fatigue level), such that the output conclusion 165 also correlates with the ground truth 175 (self-reported fatigue level).

Relationships may be determined before or after data collection, depending on the application at hand. Relationships may be represented as, for example, rules or values in a look-up table; equations; neural networks, such as Convolutional Neural Networks; a wide variety of other machine-learning or pattern-recognition constructs, such as Random Forests; or algorithmic steps. For example, a relationship could specify that fatigue level is determined based on an average change in walking speed, amount of time spent moving, and spine angle from vertical, over the course of 24 hours.

Relationships may be assigned prerequisite thresholds or constraints. For example, data acquisition for a minimum of at least three full steps could be required before a conclusion based on walking speed would be reported.

Determining Conclusions

FIGS. 9A through 9D illustrate examples of how features may be correlated with relationships to determine conclusions.

FIG. 9A represents an example of quantifying a movement; here, concluding that a person is walking at a calculated stride length. In this example, the person walks to the right (relative to the sensor) and passes behind a couch, which occludes the lower body. In order to assess gait while denied visualization of the person's lower body, the present embodiment must rely on features of the upper body instead of the lower body. In this example, two upper-body features 910 are calculated: head acceleration (rate of change of head velocity from the prior frame) and head translation (distance traversed by the head from the prior frame). In this example, three pre-determined relationships 920 are known to the present embodiment, as listed in FIG. 9A. From the features 910 and the pre-determined relationships 920, the present embodiment is able to supply conclusions 930 that the person is actively walking (not, say, sitting or reclining) with a calculated stride length.

Figure 9B:

FIG. 9B represents an example of identifying an activity; here, concluding that a person is eating a meal. In this example, the person is seated and eating a meal, such that the person's hand is moving periodically between plate and mouth. In this example, two features 940 are calculated: whether the person has been determined to be seated and stationary (which may, in turn, be calculated from other features [not shown], such as head position) and the instantaneous distance between the right hand and the head. In this example, three pre-determined relationships 950 are known to the present embodiment, as listed in FIG. 9B. From the features 940 and the pre-determined relationships 950, the present embodiment is able to supply conclusion 960 that the person is eating a meal.

Figure 9C:

FIG. 9C represents an example of identifying a mental perception; here, concluding that a person is feeling fatigue. In this example, the person walks to the right (relative to the sensor). In this example, two features 970 are calculated: walking speed (which may, in turn, be calculated from other features [not shown], such as head position) and the instantaneous spine angle relative to vertical. In this example, three pre-determined relationships 980 are known to the present embodiment, as listed in FIG. 9C. From the features 970 and the pre-determined relationships 980, the present embodiment is able to supply conclusions 990 that there is an 80% chance that the person has become fatigued over time.

Figure 9D:
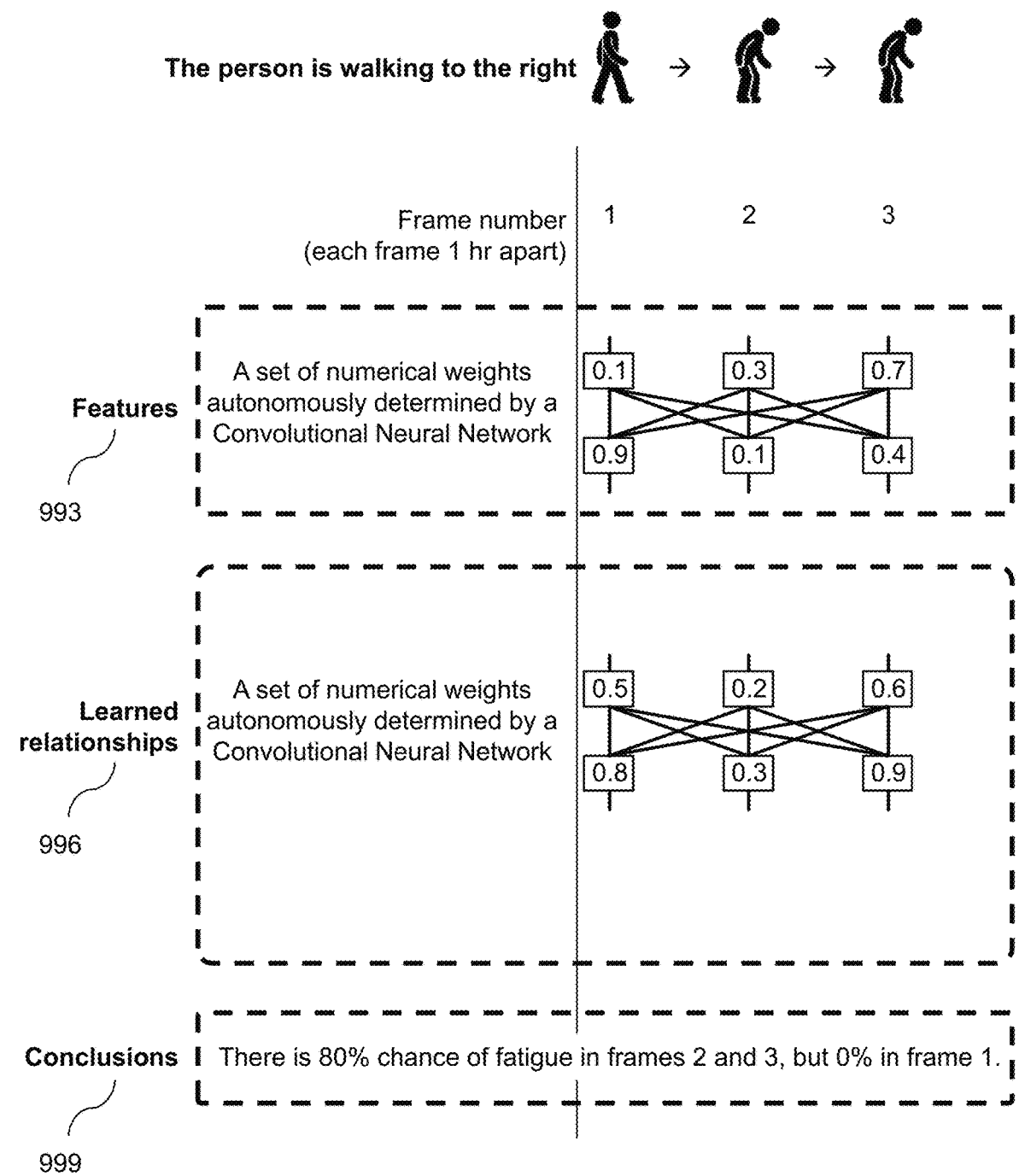

FIG. 9D represents the same example of identifying a mental perception that is shown in FIG. 9C. However, in FIG. 9D, the features 993 are autonomously determined by a Convolutional Neural Network (CNN). Furthermore, in FIG. 9D, the relationships 996 between the features 993 and the conclusions 999 are learned—not pre-determined—and are again autonomously determined, either by the same CNN or by a different CNN. The features and learned relationships generated by CNNs are encapsulated by myriad mathematical operations executed upon the input data.

The conclusions generated by steps 155, 165, and 185 may be optionally accompanied by a confidence value, or have probabilities ascribed to them. The "confidence value" is distinct from the "confidence score" calculated as a measure of the likelihood of correct person identification described herein above. For example, a confidence value could be associated with the degree to which independently-calculated features agree on, say, the presence of a footfall. For example, a confidence value could correspond to the goodness-of-fit calculation by a linear regression. There are many other ways to ascribe a confidence value to one or more sets of measurements, as is known in the art.

The conclusions generated by steps 155, 165, and 185 may be optionally quantified; for example, the conclusion 990 or 999 of FIG. 9C or FIG. 9D could include a quantified measure of the person's level of fatigue (beyond simply whether or not fatigue is present). For example, a level of fatigue could be calculated from the contemporaneous measures of walking speed and spine angle from vertical (i.e., the features 970 in FIG. 9C) or from the numerical weights of a CNN (i.e., the features 993 in FIG. 9D).

Examples (not exhaustive) of applying techniques of machine learning, artificial intelligence, or pattern recognition to the generation of conclusions follow. For example, principal component analysis (PCA) upon the Fourier transform of the location of a body portion over time, such as the head, may comprise features significant of gait; those features may be autonomously processed by a naïve Bayes classifier to produce learned relationships, thereby associating the features with the conclusion that a person has a gait abnormality. For example, the spatial locations of joints (skeleton data) over time may comprise features significant of fall risk; those features may by autonomously processed by a Random Forest to produce learned relationships, thereby associating the features with the conclusion that a person is at elevated risk of a fall. For example, the evolving three-dimensional shape of a person's body over time may comprise features significant of the action of eating; those features may be autonomously processed by a CNN to produce learned relationships, thereby associating the features with the conclusion that a person is eating.

FIG. 10 shows examples of types of features that may be correlated (i.e., associated) with relationships to determine conclusions. Conclusions can correspond to the identification (detection) and/or quantification of a movement, activity, and/or behavior (e.g., walking, dining, sleeping) or to the pain, fatigue, mood, and intent of a person. For example, if the walk speed and spine angle (features) of a person are below given thresholds (relationships), the person is determined to be fatigued (conclusion). For example, if the walk speed and spine angle of a person decrease compared to historical averages, that person's fatigue level is quantified, e.g., at a fatigue level of 4 out of 10.

Real-World Setup

A non-limiting example of a physical embodiment of the present invention is a depth sensor, connected to a computer with a network connection, placed in a person's home to measure health status. The present embodiment opportunistically samples the person's movements whenever the person happens to pass within the field-of-view. Acquired data may be analyzed in real-time; or stored for end-of-day processing; or transmitted periodically to a remote processing station, such as a cloud computer. Examples of conclusions include changes in walking speed, posture, or overall activity. Conclusions can be displayed on a website or sent to a clinician by email. Conclusions can be sent as an urgent pager or text-message alert, for example, if a quantity suddenly decreases past a threshold.

Another example of a physical embodiment is a depth sensor, connected to a computer with a network connection, placed in a retail setting to identify theft. The present embodiment calculates features for store customers, such as walking speed, changes in walking direction, direction of eye gaze, and posture. A conclusion is determined as to whether a person may have an intent to steal, accompanied by a confidence value; if the confidence value exceeds a threshold, then store personnel are alerted. The present embodiment may be trained (i.e., learn relationships) by observing operators who imitate thief-like behavior.

Another example of a physical embodiment is a depth sensor, connected to a computer with a network connection, placed in an industrial setting to identify safety issues. The present embodiment calculates features for employees, such as sudden head movement, or transition from walking to running, or walking speed that differs by some threshold from the average across all employees in that location. A conclusion is determined as to whether something may be unsafe in the environment; for example, heralded by an employee's physical reaction to a warning smell or sound.

Another example of a physical embodiment is a depth sensor, connected to a computer with a network connection, placed in a military setting to identify security threats. The present embodiment calculates features for passersby, such as walking speed, and the dropping of an object. A conclusion is determined as to whether a person may have an intent to cause harm.

Network and Computing Implementation

Figure 11:
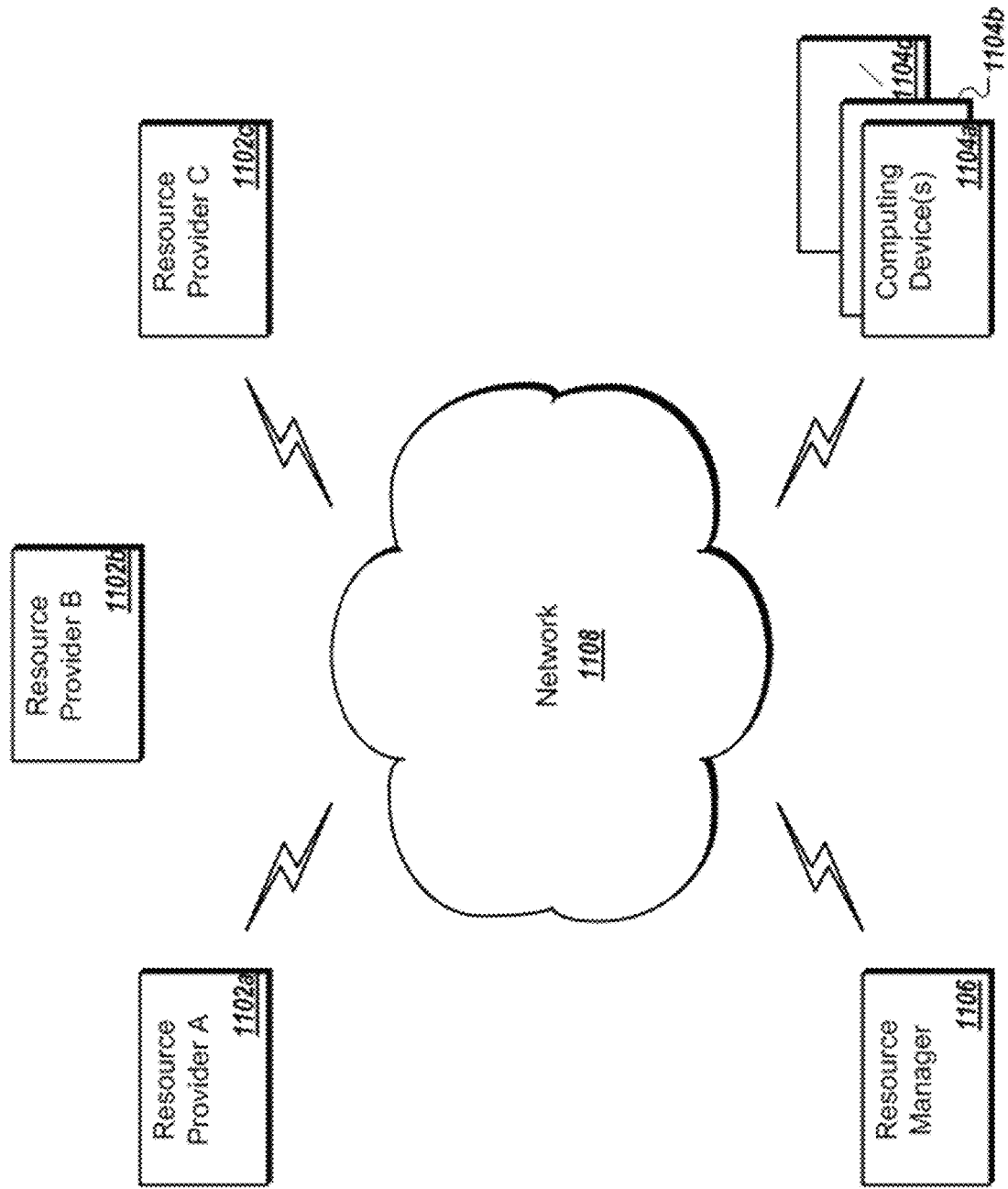
FIG. 11 is a block diagram of an example network environment for use in the methods and systems for identifying persons and objects using static and dynamic features, according to an illustrative embodiment.

As shown in FIG. 11, an implementation of a network environment 1100 for use providing a system for identifying persons with protection of privacy is shown and described. In brief overview, referring now to FIG. 11, a block diagram of an exemplary cloud computing environment 1100 is shown and described. The cloud computing environment 1100 may include one or more resource providers 1102a, 1102b, 1102c (collectively, 1102). Each resource provider 1102 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1102 may be connected to any other resource provider 1102 in the cloud computing environment 1100. In some implementations, the resource providers 1102 may be connected over a computer network 1108. Each resource provider 1102 may be connected to one or more computing device 1104a, 1104b, 1104c (collectively, 1104), over the computer network 1108.

The cloud computing environment 1100 may include a resource manager 1106. The resource manager 1106 may be connected to the resource providers 1102 and the computing devices 1104 over the computer network 1108. In some implementations, the resource manager 1106 may facilitate the provision of computing resources by one or more resource providers 1102 to one or more computing devices 1104. The resource manager 1106 may receive a request for a computing resource from a particular computing device 1104. The resource manager 1106 may identify one or more resource providers 1102 capable of providing the computing resource requested by the computing device 1104. The resource manager 1106 may select a resource provider 1102 to provide the computing resource. The resource manager 1106 may facilitate a connection between the resource provider 1102 and a particular computing device 1104. In some implementations, the resource manager 1106 may establish a connection between a particular resource provider 1102 and a particular computing device 1104. In some implementations, the resource manager 1106 may redirect a particular computing device 1104 to a particular resource provider 1102 with the requested computing resource.

Figure 12:
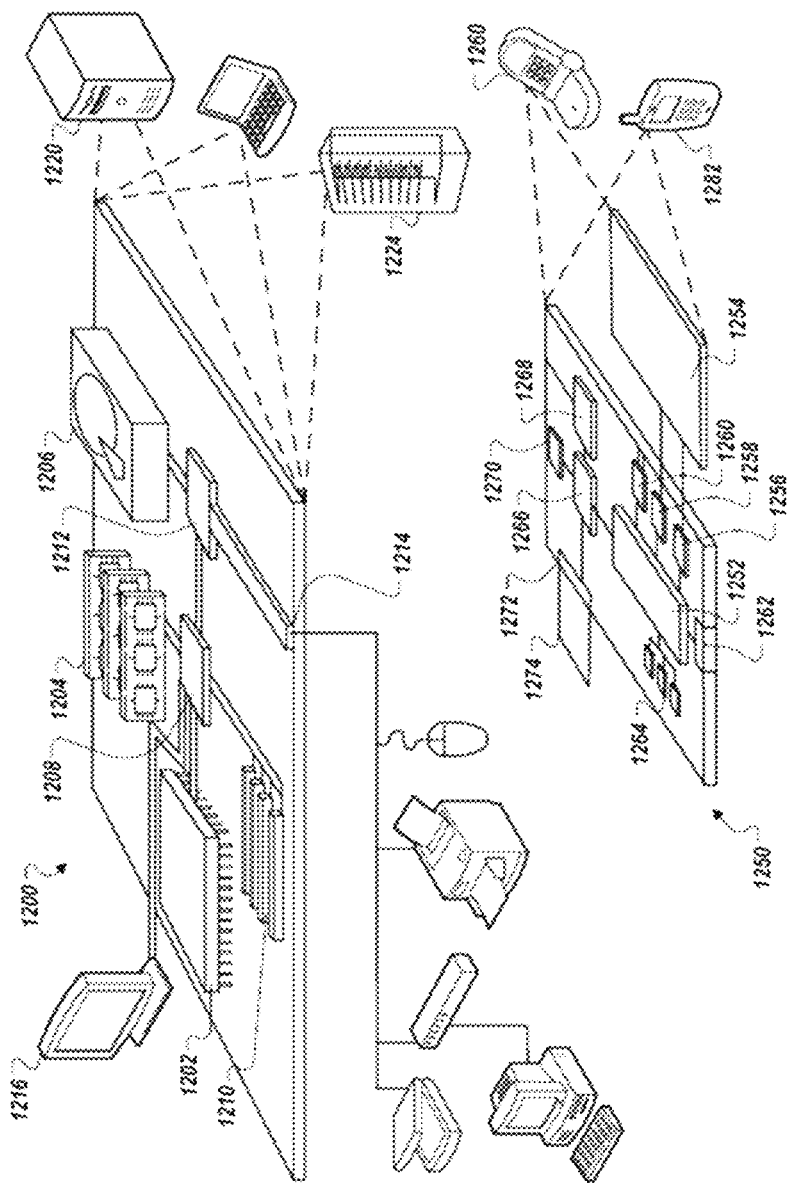
FIG. 12 is a block diagram of an example computing device and an example mobile computing device, for use in illustrative embodiments of the systems and methods presented herein.

FIG. 12 shows an example of a computing device 1200 and a mobile computing device 1250 that can be used to implement the techniques described in this disclosure. The computing device 1200 is intended to represent various forms of digital computers, such as laptops, desktops, workstations, personal digital assistants, servers, blade servers, mainframes, and other appropriate computers. The mobile computing device 1250 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1200 includes a processor 1202, a memory 1204, a storage device 1206, a high-speed interface 1208 connecting to the memory 1204 and multiple high-speed expansion ports 1210, and a low-speed interface 1212 connecting to a low-speed expansion port 1214 and the storage device 1206. Each of the processor 1202, the memory 1204, the storage device 1206, the high-speed interface 1208, the high-speed expansion ports 1210, and the low-speed interface 1212, are interconnected using various busses, and may be mounted on a common motherboard or in other manners as appropriate. The processor 1202 can process instructions for execution within the computing device 1200, including instructions stored in the memory 1204 or on the storage device 1206 to display graphical information for a GUI on an external input/output device, such as a display 1216 coupled to the high-speed interface 1208. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1204 stores information within the computing device 1200. In some implementations, the memory 1204 is a volatile memory unit or units. In some implementations, the memory 1204 is a non-volatile memory unit or units. The memory 1204 may also be another form of computer-readable medium, such as a magnetic or optical disk.

The storage device 1206 is capable of providing mass storage for the computing device 1200. In some implementations, the storage device 1206 may be or contain a computer-readable medium, such as a floppy disk device, a hard disk device, an optical disk device, or a tape device; a flash memory or other similar solid state memory device; or an array of devices, including devices in a storage area network or other configurations. Instructions can be stored in an information carrier. The instructions, when executed by one or more processing devices (for example, processor 1202), perform one or more methods, such as those described above. The instructions can also be stored by one or more storage devices such as computer- or machine-readable mediums (for example, the memory 1204, the storage device 1206, or memory on the processor 1202).

The high-speed interface 1208 manages bandwidth-intensive operations for the computing device 1200, while the low-speed interface 1212 manages lower bandwidth-intensive operations. Such allocation of functions is an example only. In some implementations, the high-speed interface 1208 is coupled to the memory 1204, the display 1216 (e.g., through a graphics processor or accelerator), and to the high-speed expansion ports 1210, which may accept various expansion cards (not shown). In the implementation, the low-speed interface 1212 is coupled to the storage device 1206 and the low-speed expansion port 1214. The low-speed expansion port 1214, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1200 may be implemented in a number of different forms, as shown in the figure. For example, it may be implemented as a standard server 1220, or multiple times in a group of such servers. In addition, it may be implemented in a personal computer such as a laptop computer 1222. It may also be implemented as part of a rack server system 1224. Alternatively, components from the computing device 1200 may be combined with other components in a mobile device (not shown), such as a mobile computing device 1250. Each of such devices may contain one or more of the computing device 1200 and the mobile computing device 1250, and an entire system may be made up of multiple computing devices communicating with each other.

The mobile computing device 1250 includes a processor 1252, a memory 1264, an input/output device such as a display 1254, a communication interface 1266, and a transceiver 1268, among other components. The mobile computing device 1250 may also be provided with a storage device, such as a micro-drive or other device, to provide additional storage. Each of the processor 1252, the memory 1264, the display 1254, the communication interface 1266, and the transceiver 1268 is interconnected using various buses, and several of the components may be mounted on a common motherboard or in other manners as appropriate.

The processor 1252 can execute instructions within the mobile computing device 1250, including instructions stored in the memory 1264. The processor 1252 may be implemented as a chipset of chips that include separate and multiple analog and digital processors. The processor 1252 may provide, for example, for coordination of the other components of the mobile computing device 1250, such as control of user interfaces, applications run by the mobile computing device 1250, and wireless communication by the mobile computing device 1250.

The processor 1252 may communicate with a user through a control interface 1258 and a display interface 1256 coupled to the display 1254. The display 1254 may be, for example, a TFT (Thin-Film-Transistor Liquid Crystal Display) display or an OLED (Organic Light Emitting Diode) display, or other appropriate display technology. The display interface 1256 may comprise appropriate circuitry for driving the display 1254 to present graphical and other information to a user. The control interface 1258 may receive commands from a user and convert them for submission to the processor 1252. In addition, an external interface 1262 may provide communication with the processor 1252, so as to enable near area communication of the mobile computing device 1250 with other devices. The external interface 1262 may provide, for example, for wired communication in some implementations or for wireless communication in other implementations, and multiple interfaces may also be used.

The memory 1264 stores information within the mobile computing device 1250. The memory 1264 can be implemented as one or more of a computer-readable medium or media, a volatile memory unit or units, or a non-volatile memory unit or units. An expansion memory 1274 may also be provided and connected to the mobile computing device 1250 through an expansion interface 1272, which may include, for example, a SIMM (Single In Line Memory Module) card interface. The expansion memory 1274 may provide extra storage space for the mobile computing device 1250, or may also store applications or other information for the mobile computing device 1250. Specifically, the expansion memory 1274 may include instructions to carry out or supplement the processes described above and may include secure information also. Thus, for example, the expansion memory 1274 may be provided as a security module for the mobile computing device 1250 and may be programmed with instructions that permit secure use of the mobile computing device 1250. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier such that the instructions, when executed by one or more processing devices (for example, processor 1252), perform one or more methods, such as those described above. The instructions can also be stored by one or more storage devices, such as one or more computer- or machine-readable mediums (for example, the memory 1264, the expansion memory 1274, or memory on the processor 1252). In some implementations, the instructions can be received in a propagated signal, for example, over the transceiver 1268 or the external interface 1262.

The mobile computing device 1250 may communicate wirelessly through the communication interface 1266, which may include digital signal processing circuitry where necessary. The communication interface 1266 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1268 using a radio-frequency. In addition, short-range communication may occur, such as using a Bluetooth®, Wi-Fi™, or other such transceiver (not shown). In addition, a GPS (Global Positioning System) receiver module 1270 may provide additional navigation- and location-related wireless data to the mobile computing device 1250, which may be used as appropriate by applications running on the mobile computing device 1250.

The mobile computing device 1250 may also communicate audibly using an audio codec 1260, which may receive spoken information from a user and convert it to usable digital information. The audio codec 1260 may likewise generate audible sound for a user, such as through a speaker, e.g., in a handset of the mobile computing device 1250. Such sound may include sound from voice telephone calls, may include recorded sound (e.g., voice messages, music files, etc.), and may also include sound generated by applications operating on the mobile computing device 1250.

The mobile computing device 1250 may be implemented in a number of different forms, as shown in the figure. For example, it may be implemented as a cellular telephone 1280. It may also be implemented as part of a smart-phone 1282, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back-end component (e.g., as a data server), or that includes a middleware component (e.g., an application server), or that includes a front-end component (e.g., a client computer having a graphical user interface or a Web browser through which a user can interact with an implementation of the systems and techniques described here), or any combination of such back-end, middleware, or front-end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Having described certain implementations of systems and methods for identifying persons and/or identifying and quantifying pain, fatigue, mood, and intent with protection of privacy, it will now become apparent to one of skill in the art that other implementations incorporating the concepts of the disclosure may be used. Therefore, the disclosure should not be limited to certain implementations, but rather should be limited only by the spirit and scope of the following claims.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of identifying and/or quantifying at least one of pain, fatigue, mood, and intent of a person via physical measurements of the person, the method comprising:
receiving, by a processor of a computing device, a data set comprising sensor data acquired by a sensor;
characterizing, by the processor, at least one member selected from the group consisting of movement, activity, and behavior of the person based on the data set, wherein said characterizing comprises:
segmenting one or more persons represented within the data set, from each other and from environmental objects represented within the data set,
calculating at least one feature of at least one of the one or more segmented persons, and
determining a conclusion based on correlating the at least one feature with a relationship;
outputting, by the processor, the conclusion; and
suspending calculating the at least one feature based on at least one of availability of specific features and relevance for the output conclusion.

2. The method of claim 1, wherein segmenting the one or more persons represented within the data set comprises performing a machine learning and/or pattern recognition technique.

3. The method of claim 1, wherein the relationship is a learned relationship.

4. The method of claim 3, wherein the learned relationship is based on a ground truth.

5. The method of claim 1, wherein the at least one feature comprises physical measurements that are direct measurements.

6. The method of claim 1, wherein the at least one feature comprises physical measurements that are indirect measurements.

7. The method of claim 1, wherein the conclusion is based on incomplete measurements.

8. The method of claim 1, wherein the at least one feature is based on measurements in the data set that are at least one of non-contiguous, non-adjacent, incomplete, inconsistent, non-sequential.

9. The method of claim 1, wherein the conclusion is based on the consolidation of several different types and combinations of features.

10. The method of claim 1, wherein the sensor data in the data set are acquired directly from a sensor and/or have undergone additional processing.

11. The method of claim 1, wherein the data set comprises one or more frames.

12. The method of claim 11, wherein each frame of the one or more frames corresponds to a snapshot of one or more data streams, comprising data acquired either preceding, or at, a particular moment in time.

13. The method of claim 11, wherein the one or more frames are captured by a single sensor at multiple points in time and/or captured by multiple sensors.

14. The method of claim 1, wherein the data set is acquired in substantially real-time, is acquired in batched mode, or is acquired from data previously stored in a database.

15. The method of claim 1, comprising pre-processing, by the processor, the data set for subsequent analysis, wherein pre-processing comprises one or more steps selected from the group consisting of filtering, conditioning, cleaning, and normalizing the data set.

16. The method of claim 1, comprising pre-processing, by the processor, the data set for subsequent analysis, wherein pre-processing is performed on raw data from the data set or calculated features.

17. The method of claim 1, wherein segmenting is performed without any information as to the identity of the segmented person.

18. The method of claim 1, comprising, after segmenting, determining a label for each of the one or more persons segmented in order to associate calculated features with a specific individual.

19. The method of claim 1, wherein the at least one feature comprises at least one member selected from the group consisting of: limb length, foot size, head shape, height, body proportion, body volume, voice frequency spectrum, voice volume, stride length, location within a field-of-view, and speed of arm raise.

20. The method of claim 1, comprising automatically calculating, by the processor, the at least one feature using a machine learning and/or pattern recognition technique.

21. The method of claim 1, wherein determining, by the processor, the desired characteristic of movement, activity, or behavior based on the data set comprises, before segmenting, pre-processing, by the processor, the data set for subsequent analysis.

22. The method of claim 1, wherein the relationship is pre-determined.

23. A system for identifying and/or quantifying at least one of pain, fatigue, mood, and intent of a person via physical measurements of the person, the system comprising:

an infrared time-of-flight sensor for acquiring sensor data comprising data corresponding to the person;
a processor; and
a memory having instructions stored thereon, wherein the instructions, when executed by the processor, cause the processor to:
receive a data set comprising the sensor data acquired by the sensor;
characterize at least one of movement, activity, and behavior of the person based on the data set, by:
segmenting one or more persons represented within the data set, from each other and from environmental objects represented within the data set,
calculating at least one feature of at least one of the one or more segmented persons, and
determining a conclusion of the person based on correlating the at least one feature with a relationship; and
output the conclusion.

24. The system of claim 23, wherein segmenting the one or more persons represented within the data set comprises performing a machine learning and/or pattern recognition technique.

25. The system of claim 23, further comprising a display and a housing for the processor and memory.

26. A method of identifying and/or quantifying at least one of pain, fatigue, mood, and intent of a person via physical measurements of the person, the method comprising:
receiving, by a processor of a computing device, a data set comprising sensor data acquired by a sensor;
discarding types of data determined to be non-private;
characterizing, by the processor, at least one member selected from the group consisting of movement, activity, and behavior of the person based on the data set, wherein said characterizing comprises:
segmenting one or more persons represented within the data set, from each other and from environmental objects represented within the data set,
calculating at least one feature of at least one of the one or more segmented persons, and
determining a conclusion based on correlating the at least one feature with a relationship; and
outputting, by the processor, the conclusion.

* * * * *